(12) United States Patent
Zundel et al.

(10) Patent No.: US 7,524,813 B2
(45) Date of Patent: Apr. 28, 2009

(54) SELECTIVELY CONJUGATED PEPTIDES AND METHODS OF MAKING THE SAME

(75) Inventors: Magali A. Zundel, Søborg (DK); Bernd Peschke, Maalov (DK); Florencio Zaragoza Dörwald, Ballerup (DK); Niels Peter Fiil, Frederiksberg (DK); Nils Langeland Johansen, Copenhagen Ø (DK); Henning Ralf Stennicke, Kokkedal (DK)

(73) Assignee: Novo Nordisk Health Care AG, Zurich (CH)

( * ) Notice: Subject to any disclaimer, the term of this patent is extended or adjusted under 35 U.S.C. 154(b) by 0 days.

(21) Appl. No.: 11/395,784

(22) Filed: Mar. 31, 2006

(65) Prior Publication Data

US 2007/0111926 A1     May 17, 2007

Related U.S. Application Data

(63) Continuation of application No. PCT/DK2004/000685, filed on Oct. 8, 2004.

(60) Provisional application No. 60/510,892, filed on Oct. 14, 2003.

(30) Foreign Application Priority Data

Oct. 10, 2003   (DK)  ........................ 2003 01496

(51) Int. Cl.
| | |
|---|---|
| *A61K 38/00* | (2006.01) |
| *A61K 38/16* | (2006.01) |
| *A61K 38/26* | (2006.01) |
| *A61K 38/27* | (2006.01) |
| *A61K 38/28* | (2006.01) |
| *C07C 251/00* | (2006.01) |
| *C07C 251/32* | (2006.01) |
| *C07C 251/72* | (2006.01) |
| *C07C 281/00* | (2006.01) |
| *C07K 14/605* | (2006.01) |
| *C07K 14/61* | (2006.01) |
| *C07K 14/62* | (2006.01) |

(52) U.S. Cl. ................. 514/3; 514/2; 514/12; 530/300; 530/303; 530/308; 530/324; 570/113

(58) Field of Classification Search ........................ None
See application file for complete search history.

(56) References Cited

U.S. PATENT DOCUMENTS

| | | | |
|---|---|---|---|
| 4,179,337 | A | 12/1979 | Davis et al. |
| 5,739,208 | A | 4/1988 | Harris |
| 2007/0105770 | A1 * | 5/2007 | Johansen et al. ............. 514/12 |

FOREIGN PATENT DOCUMENTS

| | | |
|---|---|---|
| EP | 243929 | 4/1986 |
| EP | 458064 | 5/1990 |
| WO | 92/05271 | 4/1992 |
| WO | 98/38285 | 9/1998 |
| WO | 03/044056 | 5/2003 |

OTHER PUBLICATIONS

Stennicke, H.R. et al., Anal Biochem., vol. 248, pp. 141-148 (1997).
Sato, H. et al., Bioconjug Chem., vol. 11, pp. 502-509 (2000).

* cited by examiner

*Primary Examiner*—Anish Gupta
*Assistant Examiner*—Julie Ha
(74) *Attorney, Agent, or Firm*—Shelby J. Walker

(57) ABSTRACT

Methods for the selective conjugation of peptides which comprises an enzymatic incorporation of a functional group at the C-terminal end of a peptide followed by reaction with a second compound comprising the moiety to be conjugated to the peptide, wherein said second compound comprises a functional group which selectively reacts with the incorporated functional group.

3 Claims, No Drawings

SELECTIVELY CONJUGATED PEPTIDES AND METHODS OF MAKING THE SAME

FIELD OF THE INVENTION

The present invention relates to a novel method for post-translational conjugation of peptides. Said conjugated peptides have altered characteristics and may thus be of use in therapeutic applications or they may ease the analysis or isolation and purification of said peptides.

BACKGROUND OF THE INVENTION

It is well-known to modify the properties and characteristics of peptides by conjugating groups to the peptide which duly changes the properties of the peptide. Such conjugation generally requires some functional group in the peptide to react with another functional group in a conjugating group. Typically, amino groups, such as the N-terminal amino group or the ε-amino group in lysines, have been used in combination with a suitable acylating reagent. It is often desired or even required to be able to control the conjugation reaction, i.e. to control where the conjugating compounds are attached and to control how many conjugating groups are attached. This is often referred to as specificity.

It is an object of the present invention to provide a method by which peptides may be conjugated with a high degree of specificity. In general terms, the method exploits an enzyme capable of incorporating a compound comprising a suitable functional group into the C-terminal end of a peptide, where said functional group is subsequently used as a point where to conjugate.

The use of carboxypeptidases to modify the C-terminal of peptides has been described earlier. WO 92/05271 discloses the use of carboxypeptidases and nucleophilic compounds to amidate the C-terminal carboxy group, and WO 98/38285 discloses variants of carboxypeptidase Y particular apt for this purpose.

The grafting of PEG or PEG based chains have been amply describes in the literature. By way of example, U.S. Pat. No. 5,739,208 discloses the use of a PEG with a sulfone group which reacts with thioles present in the peptide.

EP 605 963 discloses the grafting of aqueous polymers which form an oxime linkage with an aldehyde group on a protein. None of the natural amino acid comprises an aldehyde, so a hydroxyl group thus has to be oxidized as a first step in the conjugating process.

EP 243 929 discloses the use of carboxypeptidase to incorporate polypeptides, reporter groups or cytotoxic agents into the C-terminal of proteins or polypeptides.

SUMMARY OF THE INVENTION

The present inventors have surprisingly found that enzymes, e.g. carboxypeptidases may be used to incorporate into the C-terminal of peptides a first compound comprising one or more functional groups, which are not accessible in the peptide, to form a transacylated compound, and that this transacylated compound may subsequently be reacted with another compound comprising one or more functional groups which react with the functional group of the first compound but not with other functional groups accessible in the peptide. Such method provides a high degree of specificity in that the enzyme is chosen so that it only catalyses the incorporation at the C-terminal, and the two functional groups are selected so that they only react with each other, not with other functional groups accessible in the peptide. In this way, the conjugating group is only attached at one locus, and by selecting the functional groups, the number of conjugated groups can be controlled.

Accordingly, in one embodiment, the present invention provides a method for conjugating peptides, said method comprising the steps of
i) reacting in one or more steps a peptide with a first compound bearing one or more functional groups, which are not accessible in any of the amino acids constituting said peptide, in the presence of an enzyme capable of catalysing the incorporation of said first compound into the C-terminal of said peptide to form a transacylated peptide, and
ii) reacting in one or more steps said transacylated peptide with a second compound comprising one or more functional groups, wherein said functional group(s) do not react with functional groups accessible in the amino acid residues constituting said peptide, and wherein said functional group(s) in said second compound is capable of reacting with said functional group(s) in said first compound so that a covalent bond between said transacylated peptide and said second compound is formed.

It is also an objective of the present invention to provide peptides conjugated by the method of the present invention.

It is a further objective of the present invention to provide peptides which are modified in a way to make them better suited for the method of the present invention.

It is a still further objective of the present invention to provide reagents and enzymes suitable for use in the methods of the present invention.

In a still further embodiment, the present invention provides the use of peptides conjugated by methods of the present invention in therapy.

It is a still further objective of the present invention to provide compositions, e.g. pharmaceutical compositions comprising peptides conjugated by methods of the present invention.

It is a still further objective of the present invention to provide therapeutic methods for the treatment of diseases comprising the administration of conjugated peptides prepared according to the methods of the present invention.

It is a still further objective of the present invention to provide a use of conjugated peptides prepared according to the methods of the present invention in the manufacture of medicaments.

It is a still further objective of the present invention to provide a method for improving the properties of a peptide by conjugation said peptide according to the methods of the present invention.

Definitions

In the present context, the term "transacylation" is intended to indicate a reaction in which a leaving group is exchanged for a nucleophile, wherein a nucleophile is understood to be an electron-rich reagent that tends to attack the nucleus of carbons. Transpeptidation is one example of a transacylation.

In the present context, the term "not accessible" is intended to indicate that something is absent or de facto absent in the sense that it cannot be reached. When it is stated that functional groups are not accessible in a peptide to be conjugated it is intended to indicate that said functional group is absent from the peptide or, if present, in some way prevented from taking part in reactions. By way of example, said functional group could be buried deep in the structure of the peptide so that it is shielded from participating in the reaction. It is recognised that whether or not a functional group is accessible depends on the reaction conditions. It may be envisaged that in the presence of denaturing agents or at elevated temperatures the peptide may unfold to expose otherwise not accessible functional groups. It is to be understood that "not accessible" means "not accessible at the reaction condition chosen for the particular reaction of interest".

In the present context, the term "oxime bond" is intended to indicate a moiety of the formula —C=N—O—.

In the present context, the term "hydrazone bond" is intended to indicate a moiety of the formula —C=N—N—.

In the present context, the term "phenylhydrazone bond" is intended to indicate a moiety of the formula

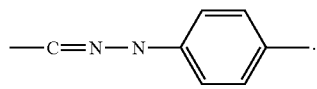

In the present context, the term "semicarbazone bond" is intended to indicate a moiety of the formula —C=N—N—C(O)—N—.

The term "alkane" is intended to indicate a saturated, linear, branched and/or cyclic hydrocarbon. Unless specified with another number of carbon atoms, the term is intended to indicate hydrocarbons with from 1 to 30 (both included) carbon atoms, such as 1 to 20 (both included), such as from 1 to 10 (both included), e.g. from 1 to 5 (both included). The terms alkyl and alkylene refer to the corresponding radical and bi-radical, respectively.

The term "alkene" is intended to indicate linear, branched and/or cyclic hydrocarbons comprising at least one carbon-carbon double bond. Unless specified with another number of carbon atoms, the term is intended to indicate hydrocarbons with from 2 to 30 (both included) carbon atoms, such as 2 to 20 (both included), such as from 2 to 10 (both included), e.g. from 2 to 5 (both included). The terms alkenyl and alkenylene refer to the corresponding radical and biradical, respectively.

The term "alkyne" is intended to indicate linear, branched and/or cyclic hydrocarbons comprising at least one carbon-carbon triple bond, and it may optionally comprise one or more carbon-carbon double bonds. Unless specified with another number of carbon atoms, the term is intended to indicate hydrocarbons with from 2 to 30 (both included) carbon atoms, such as from 2 to 20 (both included), such as from 2 to 10 (both included), e.g. from 2 to 5 (both included). The terms alkynyl and alkynylene refer to the corresponding radical and bi-radical, respectively.

The term "homocyclic aromatic compound" is intended to indicate aromatic hydrocarbons, such as benzene and naphthalene.

The term "heterocyclic compound" is intended to indicate a cyclic compound comprising 5, 6 or 7 ring atoms from which 1, 2, 3 or 4 are hetero atoms selected from N, O and/or S. Examples include heterocyclic aromatic compounds, such as thiophene, furan, pyran, pyrrole, imidazole, pyrazole, isothiazole, isooxazole, pyridine, pyrazine, pyrimidine, pyridazine, as well as their partly or fully hydrogenated equivalents, such as piperidine, pirazolidine, pyrrolidine, pyroline, imidazolidine, imidazoline, piperazine and morpholine.

The terms "hetero alkane", "hetero alkene" and "hetero alkyne" is intended to indicate alkanes, alkenes and alkynes as defined above, in which one or more hetero atom or group have been inserted into the structure of said moieties. Examples of hetero groups and atoms include —O—, —S—, —S(O)—, —S(O)$_2$—, —C(O)— —C(S)— and —N(R*)—, wherein R* represents hydrogen or $C_1$-$C_6$-alkyl. Examples of heteroalkanes include.

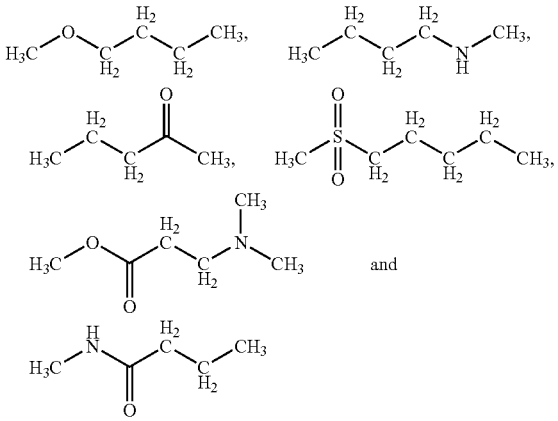

and

The term "radical" or "biradical" is intended to indicate a compound from which one or two, respectively, hydrogen atoms have been removed. When specifically stated, a radical may also indicate the moiety formed by the formal removal of a larger group of atoms, e.g. hydroxyl, from a compound.

The term "halogen" is intended to indicate members of the seventh main group of the periodic table, i.e. F, Cl, Br and I.

The term "PEG" is intended to indicate polyethylene glycol of a molecular weight between 500 and 150,000 Da, including analogues thereof, wherein for instance the terminal OH-group has been replaced by a methoxy group (referred to as mPEG).

In the present context, the words "peptide" and "protein" are used interchangeably and are intended to indicate the same. The term "peptide" is intended to indicate a compound with two or more amino acid residues linked by a peptide bond. The amino acids may be natural or unnatural. The term is also intended to include said compounds substituted with other peptides, saccharides, lipids, or other organic compound, as well as compounds wherein one or more amino acid residue have been chemically modified and peptides comprising a prosthetic group.

In the present context, the term "aryl" is intended to indicate a carbocyclic aromatic ring radical or a fused aromatic ring system radical wherein at least one of the rings are aromatic. Typical aryl groups include phenyl, biphenylyl, naphthyl, and the like.

The term "heteroaryl", as used herein, alone or in combination, refers to an aromatic ring radical with for instance 5 to 7 member atoms, or to a fused aromatic ring system radical with for instance from 7 to 18 member atoms, wherein at least one ring is aromatic, containing one or more heteroatoms as ring atoms selected from nitrogen, oxygen, or sulfur heteroatoms, wherein N-oxides and sulfur monoxides and sulfur dioxides are permissible heteroaromatic substitutions. Examples include furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl, and the like.

The term "conjugate" as a noun is intended to indicate a modified peptide, i.e. a peptide with a moiety bonded to it to modify the properties of said peptide. As a verb, the term is intended to indicate the process of bonding a moiety to a peptide to modify the properties of said peptide.

As used herein, the term "prodrug" indicates biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

As used herein, the term "biohydrolyzable ester" is an ester of a drug substance (in casu, a compound according to the invention) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is, for example increased solubility or that the biohydrolyzable ester is orally absorbed from the gut and is transformed to a compound according to the present invention in plasma. Many examples of such are known in the art and include by way of example lower alkyl esters (e.g., $C_1$-$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in casu, a compound according to the present invention) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is, for example increased solubility or that the biohydrolyzable amide is orally absorbed from the gut and is transformed to a compound according to the present invention in plasma. Many examples of such are known in the art and include by way of example lower alkyl amides, α-amino acid amides, alkoxyacyl amides, and alkylaminoalkylcarbonyl amides.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

A "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal, in particular a human being, but it may also include animals, such as dogs, cats, cows, sheep and pigs.

DESCRIPTION OF THE INVENTION

In principle, any enzyme capable of catalysing the incorporation of a compound into a peptide is useful in the methods of the present invention. By way of example, useful enzymes include carboxypeptidases, which constitute a group of peptide hydrolases belonging to the classification groups E.C. 3.4.16, 3.4.17 and 3.4.18. The in vivo reaction catalysed by said enzymes is the hydrolysis of the C-terminal amino acid residue. Various carboxypeptidases are known and they differ in what terminal amino acid residue they are capable of cleaving off. During the catalytic cycle an enzyme-substrate complex is formed which under normal in vivo conditions is subjected to a nucleophilic attack by a water molecule, which eventually leads to the hydrolysis of the peptide bond. In the methods of the present invention, however, a nucleophilic reagent is added, which can out compete water as a nucleophile. Moreover, the water activity may be reduced by running the reaction in solvents or in aqueous solvents. In the methods of the present invention, said nucleophile attacks the enzyme-substrate complex eventually forming a transacylated compound. On top of being a nucleophile, said reagent also has to comprise one or more functional groups, which are not accessible in the peptide to be conjugated.

Other enzymes which could be applied in the methods of the present invention include trypsin.

The reaction of the peptide and the nucleophile affords a transacylated peptide wherein the C-terminal amino acid residue has been exchanged with the nucleophilic compound, which comprises one or more functional groups which are not accessible in the peptide to be conjugated. The overall result of this reaction (or this series of reactions) is an incorporation of one or more functional groups into the peptide which are present at only one locus in the peptide. A subsequent reaction (or series of reactions) of this transacylated peptide with a compound comprising the moiety to be conjugated to the peptide and one or more functional groups, which only react with the functional groups added to the peptide in the transacylation reaction, effects a selective conjugation of the peptide to be conjugated.

Compared to other conjugation methods which take advantage of functional groups already present in the peptide, e.g. N-terminal amino groups or ε-amino groups of lysines, the method of the present invention offers the advantage of improved selectivity. The incorporation of one or more functional groups not accessible in the peptide ensures that the conjugation takes place at only specified loci.

As mentioned earlier, any enzyme capable of catalysing the incorporation of a compound into a peptide may be used in the methods of the present invention, and in particular carboxypeptidases are useful. Examples of particular useful carboxypeptideas are serine-type carboxypeptidases, such as lysosomalPro-X carboxypeptidase (also known as proline carboxypeptidase, angiotensinase C, lysosomal carboxypeptidase C and prolylcarboxypeptidase), serine-type D-Ala-D-Ala carboxypeptidase (also known as D-alanyl-D-alanine carboxypeptidase, DD-peptidase and DD-transpeptidase), carboxypeptidase C (also known as Serine-type carboxypeptidase 1, cathepsin A, carboxypeptidase Y and lysosomal protective protein) and carboxypeptidase D (also known as carboxypeptidase KEX1 and carboxypeptidase Si); metallocarboxypeptidases, such as carboxypeptidase A, carboxypeptidase B (also known as protaminase), lysine(arginine) carboxypeptidase (also known as carboxypeptidase N), and Gly-X carboxypeptidase (also known as carboxypeptidase S); and cysteine-type carboxypeptidase (also known as lysosomal carboxypeptidase B, cathepsin B2, Cathepsin Iv and acid carboxypeptidase). It is also well-known that amino acid residues may be changed, added or deleted in the sequence of carboxypeptidases to modify the catalytic properties of the enzyme. Such modified carboxypeptidases are disclosed in, e.g. WO 98/38285, which is incorporated herein by reference. Particular mentioning is made of carboxypeptidase Y as a useful enzyme.

Many nucleophilic compounds are known which could be incorporated into peptides according to the methods of the present invention, and α-amino acids is one such type of nucleophilic compounds. For the purpose of the present invention, it is, however, preferred to select the nucleophilic compound so that the transacylated compound formed is not itself a substrate for the enzyme applied. Stated differently, it is preferred to apply a nucleophilic compound which effectively blocks any further reaction of the enzyme. One example of such compounds is amides of α-amino acids as carboxy amidated peptides are not substrates for carboxypeptidases.

It is recognised that whether or not a compound is a substrate for a given enzyme in principle depends on the conditions, e.g. the time frame, under which the reaction takes place. Given sufficient time, many compounds are, in fact, substrates for an enzyme although they are not under normal conditions regarded as such. When it is stated above that the transacylated compound itself should not be a substrate of the enzyme it is intended to indicate that the tranacylated compound itself is not a substrate for the enzyme to an extent where the following reactions in the method of the present invention are disturbed. If the transacylated compound is, in fact, a substrate for the enzyme, the enzyme may be removed or inactivated, e.g. by enzyme inhibitors, following the transacylation reaction.

In one embodiment, the invention relates to a method of conjugating peptides, wherein a peptide P is reacted in one or more steps with a first compound, which is an α-amino acid amide represented by the formula

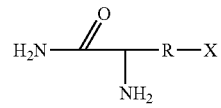

in the presence of carboxypeptidase to form a transacylated peptide of the formula

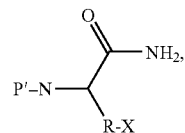

said transacylated peptide being further reacted in one or more steps with a second compound of the formula

to form a conjugated peptide of the formula

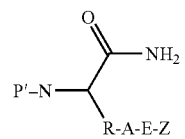

wherein R represents a linker or a bond;

wherein P' represents the peptide obtained when the C-terminal amino acid is removed from the peptide P;

X represents a radical comprising a functional group not accessible in the amino acid residues constituting the peptide P';

Y represents a radical comprising one or more functional groups which groups react with functional groups present in X, and which functional groups do not react with functional groups accessible in the peptide P';

E represents a linker or a bond;

A represents the moiety formed by the reaction between the functional groups comprised in X and Y; and Z is the moiety to be conjugated to the peptide, wherein said moiety decreases the clearance of the compound of formula [a] in comparison with the clearance of P.

In a further embodiment, the invention relates to methods of conjugating peptides as disclosed above, which further comprises the step of formulating the resulting conjugated peptide in a pharmaceutical composition.

Following the conjugation, the conjugated peptide may be isolated and purified by techniques well-known in the art. The conjugated peptide may also be converted into a pharmaceutically acceptable salt or prodrug, if relevant.

The moiety, A, formed in the reaction between the functional groups of X and Y may in principle be of any kind depending on what properties of the final conjugated peptide is desired. In some situation it may be desirable to have a labile bond which can be cleaved at some later stage, e.g. by some enzymatic action or by photolysis. In other situations, it may be desirable to have a stable bond, so that a stable conjugated peptide is obtained. Particular mentioning is made of the type of moieties formed by reactions between amine derivatives and carbonyl groups, such as oxime, hydrazone, phenylhydrazone and semicarbazone moieties.

In one embodiment the functional groups of X and Y are selected from amongst carbonyl groups, such as keto and aldehyde groups, and amino derivatives, such as

| | |
|---|---|
| hydrazine derivatives | —NH—NH$_2$, |
| hydrazine carboxylate derivatives | —O—C(O)—NH—NH$_2$, |
| semicarbazide derivatives | —NH—C(O)—NH—NH$_2$, |
| thiosemicarbazide derivatives | —NH—C(S)—NH—NH$_2$, |
| carbonic acid dihydrazide derivatives | —NHC(O)—NH—NH—C(O)—NH—NH$_2$, |
| carbazide derivatives | —NH—NH—C(O)—NH—NH$_2$, |
| thiocarbazide derivatives | —NH—NH—C(S)—NH—NH$_2$, |
| aryl hydrazine derivatives | —NH—C(O)—C$_6$H$_4$—NH—NH$_2$, and |
| hydrazide derivatives | —C(O)—NH—NH$_2$; | oxylamine derivatives, such as —O—NH$_2$, —C(O)—O—NH$_2$, —NH—C(O)—O—NH$_2$ and —NH—C(S)—O—NH$_2$.

It is to be understood, that if the functional group comprised in X is a carbonyl group, then the functional group comprised in Y is an amine derivative, and vice versa. Due to the presence of —NH$_2$ groups in most peptides, a better selectivity is believed to be obtained if X comprises a keto- or an aldehyde-functionality.

Another example of a suitable pair of X and Y is azide derivatives (—N$_3$) and alkynes which react to form a triazole moiety.

Another example of a suitable pair of X and Y is alkyne and nitril-oxide, which reacts to form a isooxazolidine moiety.

In particular, the group to be transacylated,

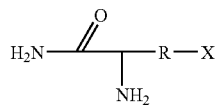

may be selected from amongst 2-amino-3-oxo-butyramide, 2-amino-6-(4-oxo-pentanoylamino)-hexanoic acid amide, 2-amino-3-(2-oxo-2-phenyl-ethylsulfanyl)-propionamide, 2-amino-5-oxo-hexanoic acid amide, 2-amino-3-oxo-propionamide, 2-amino-6-(4-acetylbenzoylamino)hexanoic acid amide, 2-amino-3-oxopropionic acid amide, (2S)-Amino-3-[4-(2-oxopropoxy)phenyl]propionamide, (2S)-Amino-3-[4-(2-oxobutoxy)phenyl]propionamide, (2S)-Amino-3-[4-(2-oxopentoxy)phenyl]propionamide, (2S)-Amino-3-[4-(4-oxopentoxy)phenyl]propionamide, (2S)-2-Amino-6-(4-oxo-4-phenylbutyrylamino)hexanoic acid amide, 4-Acetyl-N-((5S)-5-amino-5-carbamoylpentyl)benzamide, (2S)-2-Amino-6-(4-oxo-4-(4-chlorophenylbutyrylamino)hexanoic acid amide, 3-Acetyl-N-((5S)-5-amino-5-carbamoylpentyl)benzamide, 2-Acetyl-N-((5S)-5-amino-5-carbamoylpentyl)benzamide, (2S)-2-amino-3-(4-(prop-2-ynyloxy)phenyl)propionamide, (S)-2-aminopent-4-ynoicacid amide and S-phenylacylcysteine amide.

Both the compound to be transacylated and the compound to be reacted with the transacylated peptide comprises a linker, R and E, respectively. These linkers, which are independent of each other, may be absent or selected from amongst alkane, alkene or alkyne diradicals and hetero alkane, hetero alkene and hetero alkyne diradicals, wherein one or more optionally substituted aromatic homocyclic biradical or biradical of a heterocyclic compound, e.g. phenylene or piperidine biradical may be inserted into the aforementioned biradicals. It is to be understood that said linkers may also comprise substitutions by groups selected from amongst hydroxyl, halogen, nitro, cyano, carboxyl, aryl, alkyl and heteroaryl.

Both E and R represent bonds or linkers, and in the present context the term "linker" is intended to indicate a moiety functioning as a means to separate Y from Z and X from NH$_2$—C(O)—C(NH$_2$)—, respectively. One function of the linkers E and R may be to provide adequate flexibility in the linkage between the peptide and the conjugated moiety Z. Typical examples of E and R include bi-radicals of straight, branched and/or cyclic C$_{1-10}$alkane, C$_{2-10}$alkene, C$_{2-10}$alkyne; C$_{1-10}$heteroalkane, C$_{2-10}$heteroalkene, C$_{2-10}$heteroalkyne, wherein one or more homocyclic aromatic compound biradical or heterocyclic compound biradical may be inserted. Particular examples of E and R include

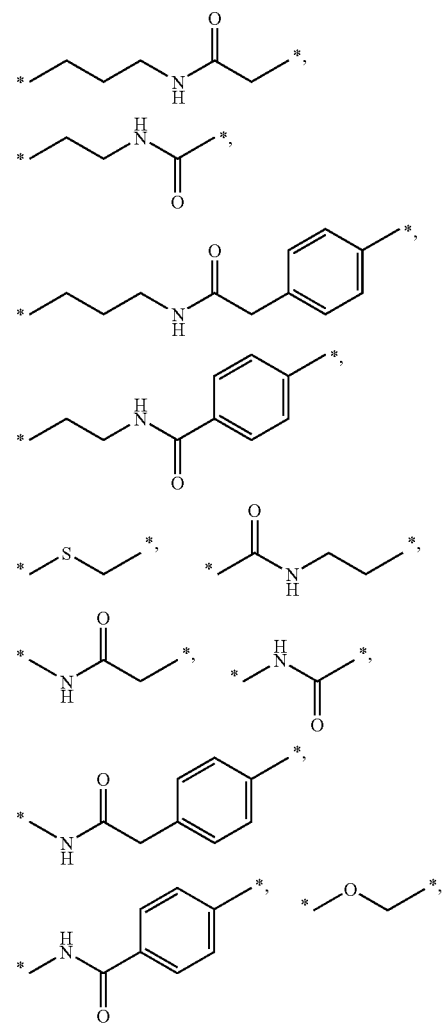

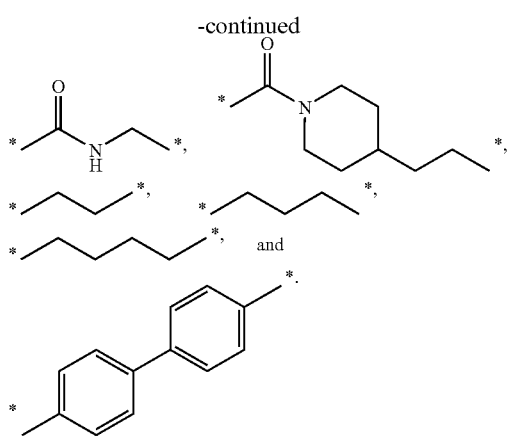

A need for modifying peptides may arise for any number of reasons, and this is also reflected in the kind of compounds that may be conjugated to peptides according to the methods of the present invention. It may be desirable to conjugate peptides to alter the physicochemical properties of the peptide, such as e.g. to increase (or to decrease) solubility to modify the bioavailability of therapeutic peptides. In another embodiment, it may be desirable to modify the clearance rate in the body, e.g. by conjugating compounds to the peptide which binds to plasma proteins, such as e.g. albumin, or which increase the size of the peptide to prevent or delay discharge through the kidneys. In another embodiment, it may be desirable to conjugate a label to facilitate analysis of the peptide. Examples of such label include radioactive isotopes, fluorescent markers and enzyme substrates. In still another embodiment, a compound is conjugated to a peptide to facilitate isolation of the peptide. For example, a compound with a specific affinity to a particular column material may be conjugated to the peptide. It may also be desirable to modify the immunogenecity of a peptide, e.g. by conjugating a peptide so as to hide, mask or eclipse one or more immunogenic epitopes at the peptide.

In particular, the methods of the present invention may be used to decrease the clearance in order to increase the plasma half-life of the modified peptide compared to the corresponding un-modified peptide. The term "plasma half-life" is used in its ordinary meaning, i.e. the time at which 50% of the biological activity of the peptide is present in the plasma prior to being cleared. Alternative terms include serum half-life, circulating half-life, circulatory half-life, serum clearance, plasma clearance, and clearance half-life.

The term "increased" used in connection with plasma half-life is used to indicate that the half-life of the conjugated peptide is significantly increased relative to the half-life of the corresponding un-modified peptide. For instance, the half-life may be increased by at least 25%, at least 50%, at least 100%, at least 150%, at least 200% or even at least 500%.

In one embodiment, the present invention relates to methods of conjugating peptides as disclosed above, which further comprises the step of measuring whether an increase in the plasma half-life has been effected.

Particular examples of Z which gives rise to a decrease in clearance of compounds of formula [a] in comparison with the clearance of P include organic moieties, such as PEG or mPEG radicals and amino derivatives thereof; straight, branched and/or cyclic $C_{1-22}$alkyl, $C_{2-22}$alkenyl, $C_{2-22}$alkynyl, $C_{1-22}$heteroalkyl, $C_{2-22}$heteroalkenyl, $C_{2-22}$heteroalkynyl, wherein one or more homocyclic aromatic compound biradical or heterocyclic compound biradical may be inserted, and wherein said $C_1$-$C_{22}$ or $C_2$-$C_{22}$ radicals may optionally be substituted with one or more substituents selected from hydroxyl, halogen, carboxyl, heteroaryl and aryl, wherein said aryl or heteroaryl may optionally be further substituted by one or more substituents selected from hydroxyl, halogen, and carboxyl; steroid radicals; lipid radicals; polysaccharide radicals, e.g. dextrans; polyamide radicals e.g. polyamino acid radicals; PVP radicals; PVA radicals; poly(1-3-dioxalane); poly(1,3,6-trioxane); ethylene/maleic anhydride polymer; Cibacron dye stuffs, such as Cibacron Blue 3GA, and polyamide chains of specified length, as disclosed in WO 00/12587, which is incorporated herein by reference.

Particular mentioning is made of $C_{10-20}$alkyl, such as $C_{15}$ and $C_{17}$, and benzophenone derivatives of the formula

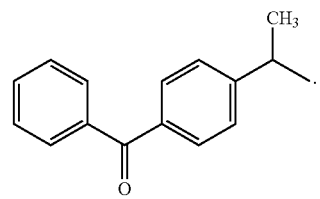

The PEG conjugated to a peptide according to the present invention may be of any molecular weight. In particular the molecular weight may be between 500 and 100,000 Da, such as between 500 and 60,000 Da, such as between 1000 and 40,000 Da, such as between 5000 and 40,000 Da. In particular, PEG with molecular weights of 10000 Da, 20000 Da, 30000 Da or 40000 Da may be used in the present invention.

In one embodiment, Z comprises one or more moieties that are known to bind to plasma proteins, such as e.g. albumin. The ability of a compound to bind to albumin may be determined as described in *J. Med. Chem,* 43, 2000, 1986-1992, which is incorporated herein by reference. In the present context, a compound is defined as binding to albumin if Ru/Da is above 0.05, such as above 0.10, such as above 0.12 or even above 0.15.

In another embodiment of the invention the albumin binding moiety is a peptide, such as a peptide comprising less than 40 amino acid residues. A number of small peptides which are albumin binding moieties are disclosed in *J. Biol. Chem.* 277, 38 (2002) 35035-35043, which is incorporated herein by reference.

Z may be branched so that Z comprises more than one of the above mentioned labels or radicals.

Particular examples of compounds of the formula Y-E-Z include

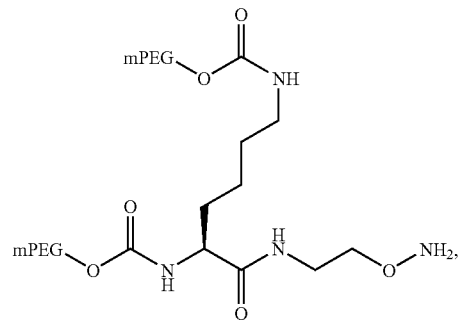

wherein mPEG has a molecular weight of 20 kDa,

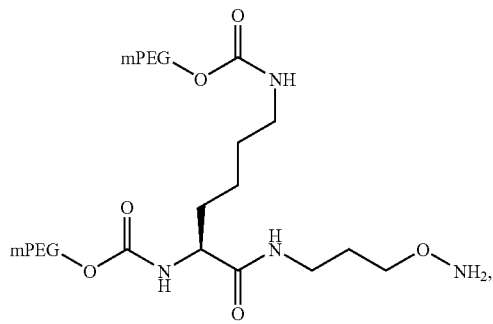

wherein mPEG has a molecular weight of 20 kDa,

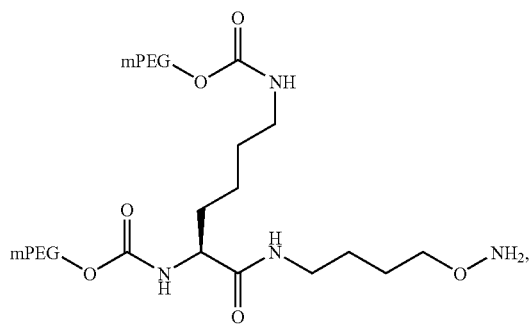

wherein mPEG has a molecular weight of 20 kDa,

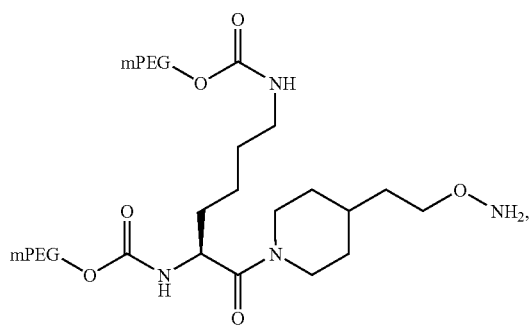

wherein mPEG has a molecular weight of 20 kDa,

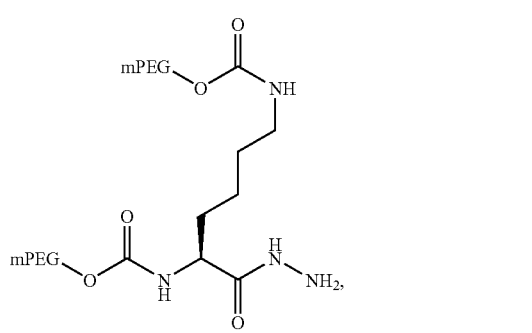

wherein mPEG has a molecular weight of 20 kDa,

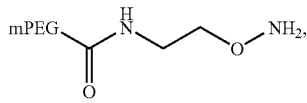

wherein mPEG has a molecular weight of 20 kDa,

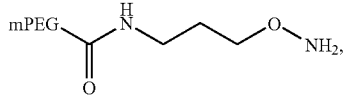

wherein mPEG has a molecular weight of 20 kDa,

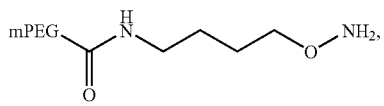

wherein mPEG has a molecular weight of 20 kDa,

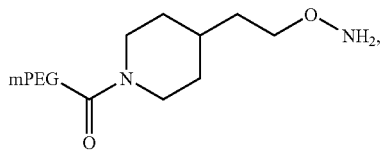

wherein mPEG has a molecular weight of 20 kDa,

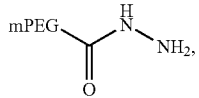

wherein mPEG has a molecular weight of 20 kDa,

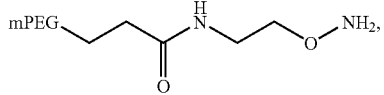

wherein mPEG has a molecular weight of 20 kDa,

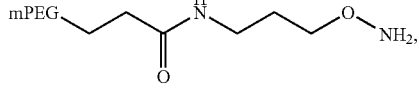

wherein mPEG has a molecular weight of 20 kDa,

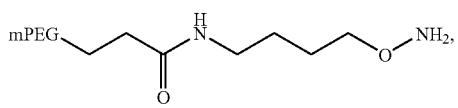

wherein mPEG has a molecular weight of 20 kDa,

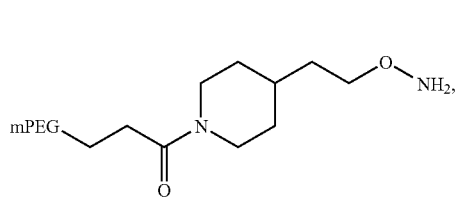

wherein mPEG has a molecular weight of 20 kDa,

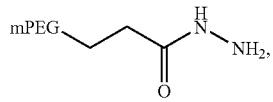

wherein mPEG has a molecular weight of 20 kDa,

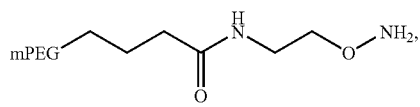

wherein mPEG has a molecular weight of 20 kDa,

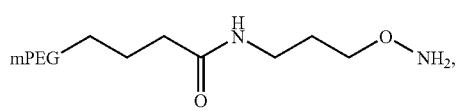

wherein mPEG has a molecular weight of 20 kDa,

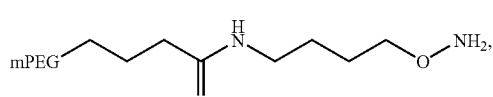

wherein mPEG has a molecular weight of 20 kDa,

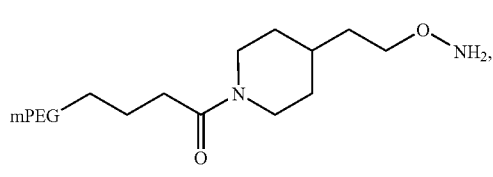

wherein mPEG has a molecular weight of 20 kDa,

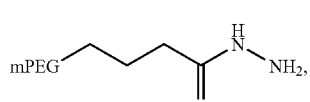

wherein mPEG has a molecular weight of 20 kDa,

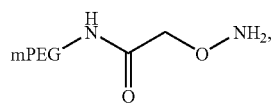

wherein mPEG has a molecular weight of 20 kDa,

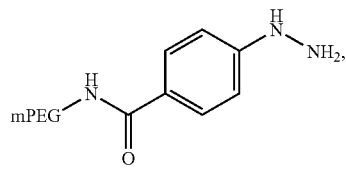

wherein mPEG has a molecular weight of 20 kDa,

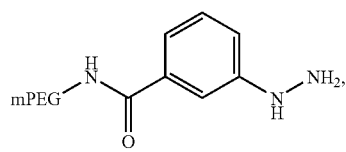

wherein mPEG has a molecular weight of 20 kDa,

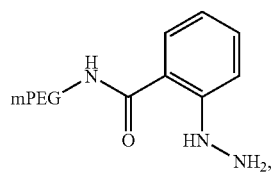

wherein mPEG has a molecular weight of 20 kDa,

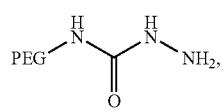

wherein mPEG has a molecular weight of 20 kDa,

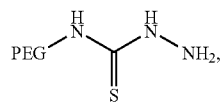

wherein mPEG has a molecular weight of 20 kDa,

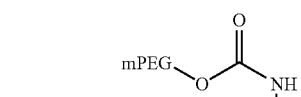

wherein mPEG has a molecular weight of 20 kDa,

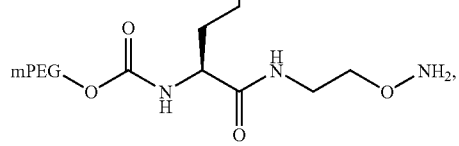

wherein mPEG has a molecular weight of 10 kDa,

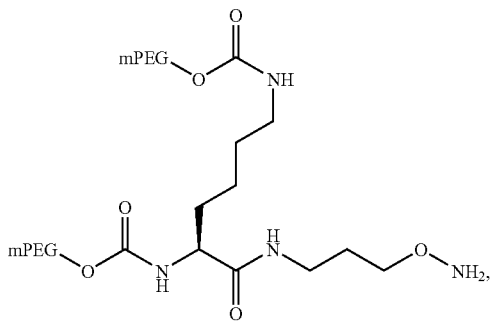

wherein mPEG has a molecular weight of 10 kDa,

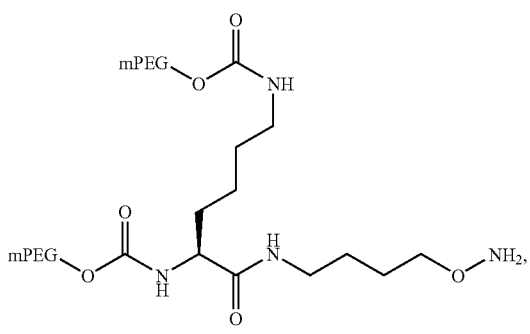

wherein mPEG has a molecular weight of 10 kDa,

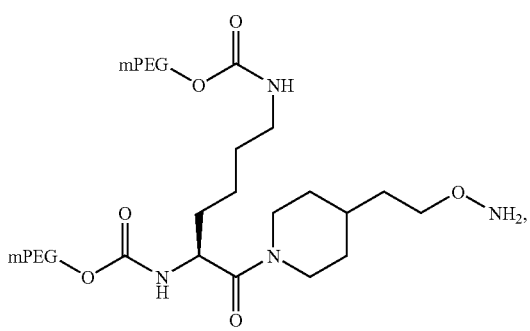

wherein mPEG has a molecular weight of 10 kDa,

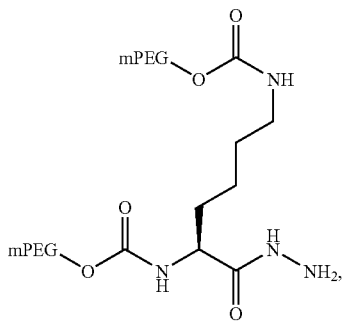

wherein mPEG has a molecular weight of 10 kDa,

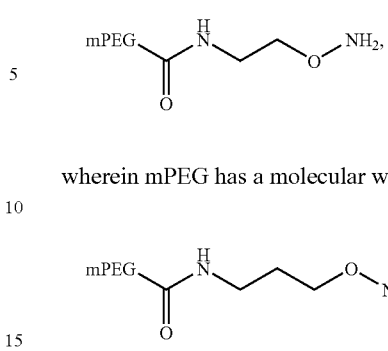

wherein mPEG has a molecular weight of 10 kDa,

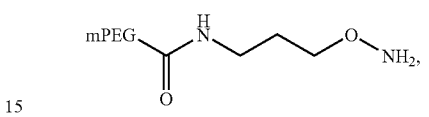

wherein mPEG has a molecular weight of 10 kDa,

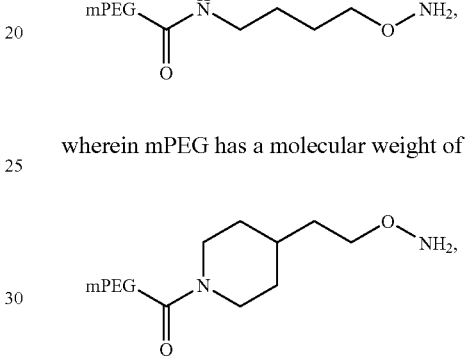

wherein mPEG has a molecular weight of 10 kDa,

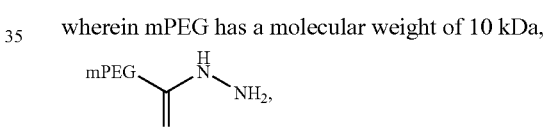

wherein mPEG has a molecular weight of 10 kDa,

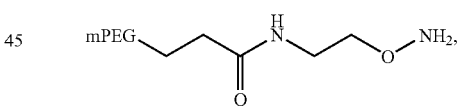

wherein mPEG has a molecular weight of 10 kDa,

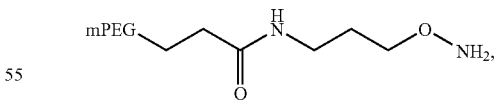

wherein mPEG has a molecular weight of 10 kDa,

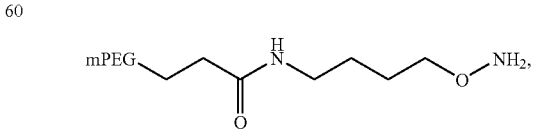

wherein mPEG has a molecular weight of 10 kDa,

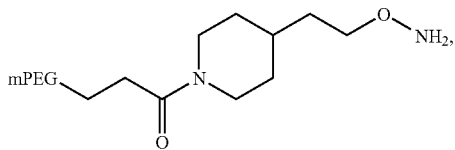

wherein mPEG has a molecular weight of 10 kDa,

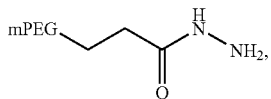

wherein mPEG has a molecular weight of 10 kDa,

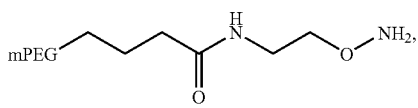

wherein mPEG has a molecular weight of 10 kDa,

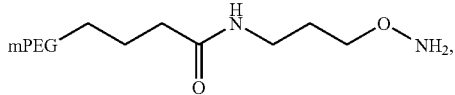

wherein mPEG has a molecular weight of 10 kDa,

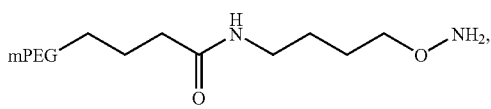

wherein mPEG has a molecular weight of 10 kDa,

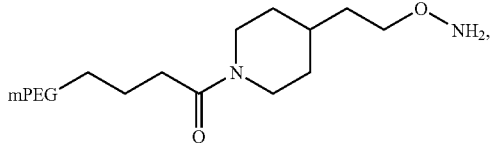

wherein mPEG has a molecular weight of 10 kDa,

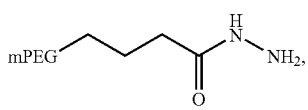

wherein mPEG has a molecular weight of 10 kDa,

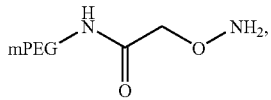

wherein mPEG has a molecular weight of 10 kDa,

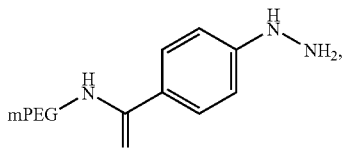

wherein mPEG has a molecular weight of 10 kDa,

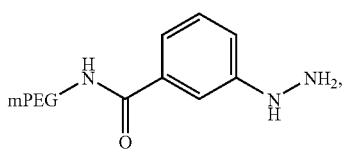

wherein mPEG has a molecular weight of 10 kDa,

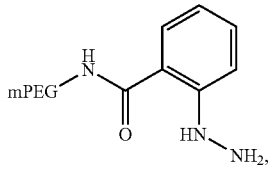

wherein mPEG has a molecular weight of 10 kDa,

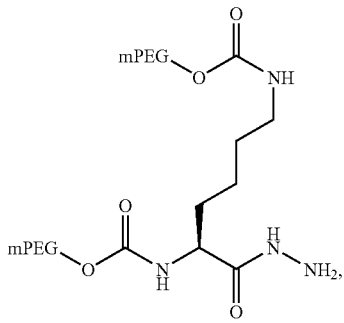

wherein mPEG has a molecular weight of 10 kDa,

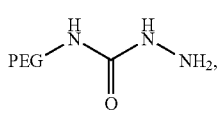

wherein mPEG has a molecular weight of 10 kDa,

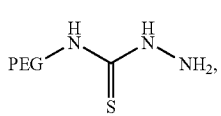

wherein mPEG has a molecular weight of 10 kDa,

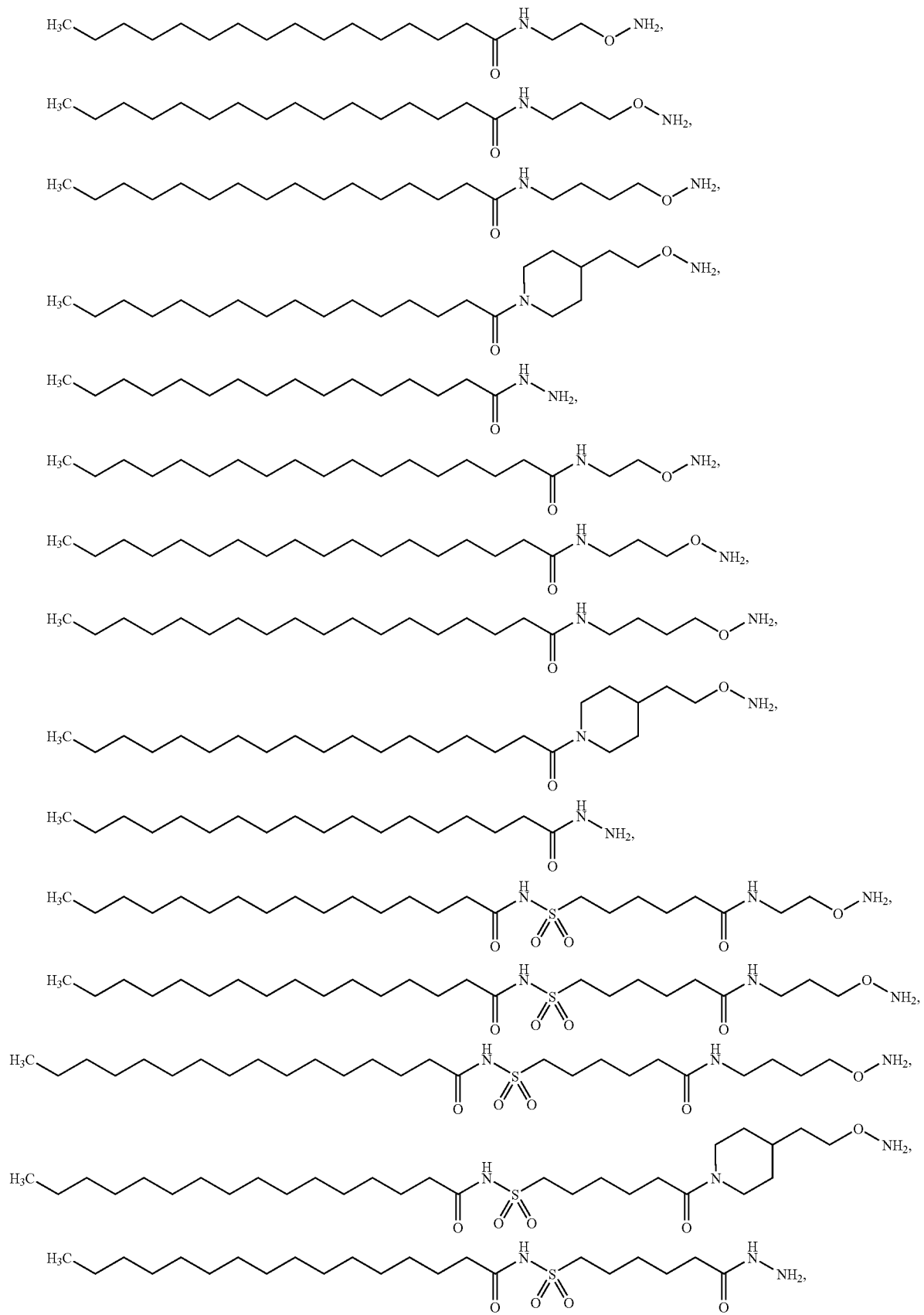

-continued
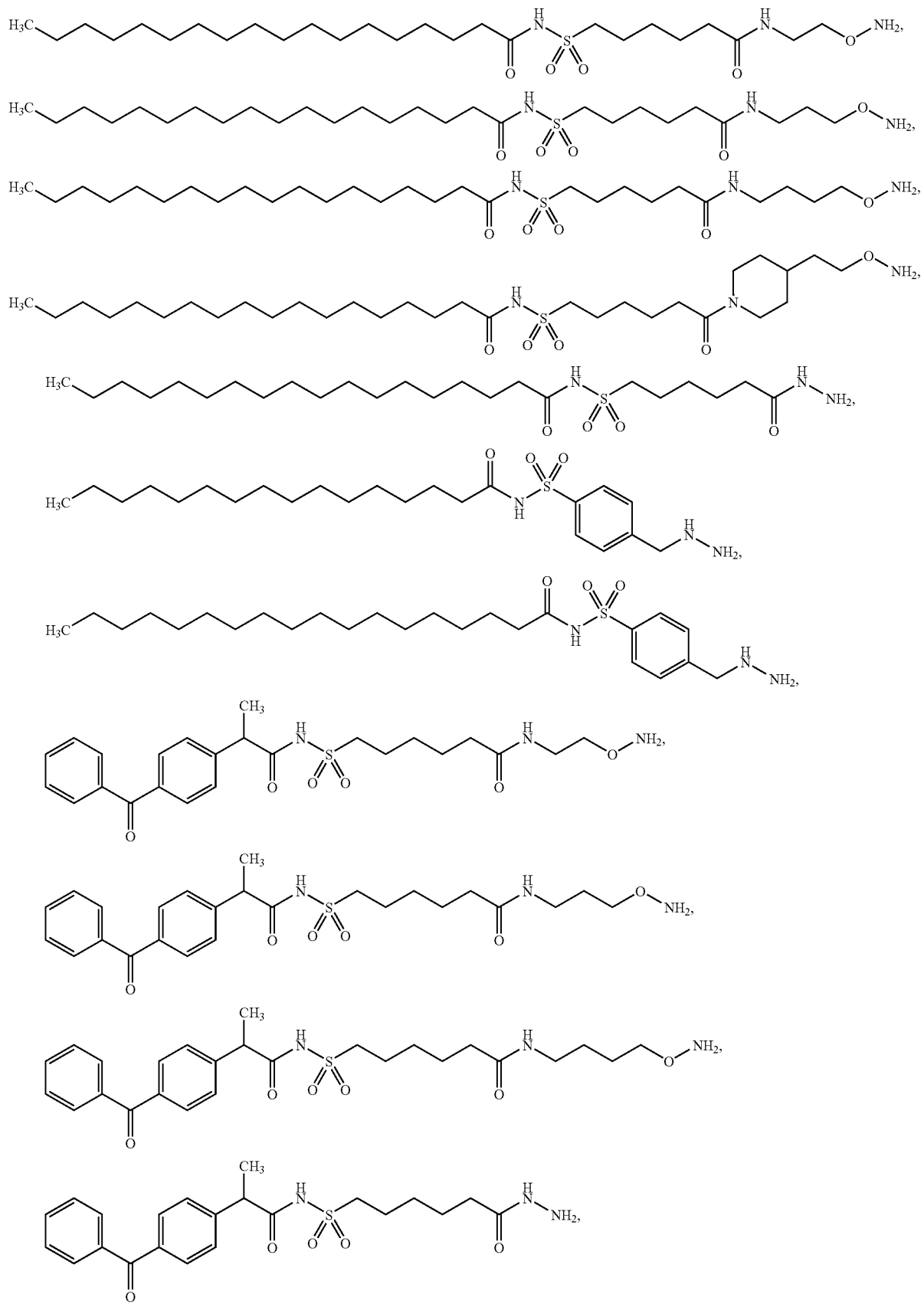

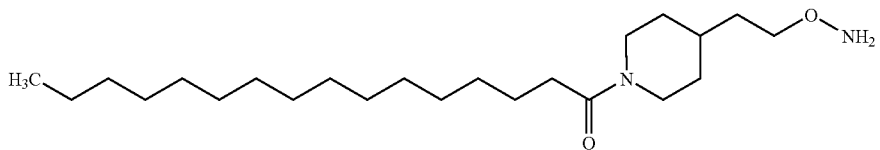
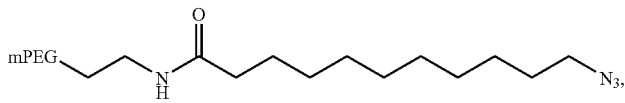
wherein mPEG has a molecular weight of 20 kDa,
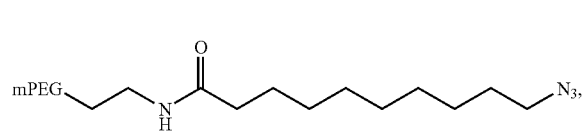
wherein mPEG has a molecular weight of 20 kDa,
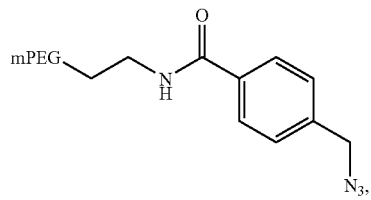
wherein mPEG has a molecular weight of 20 kDa,
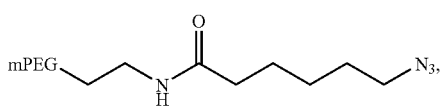
wherein mPEG has a molecular weight of 20 kDa,
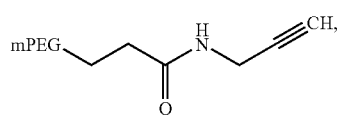
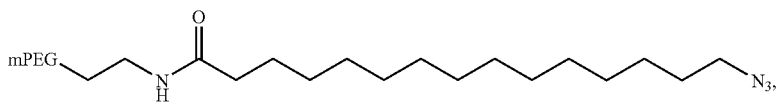
wherein mPEG has a molecular weight of 20 kDa,
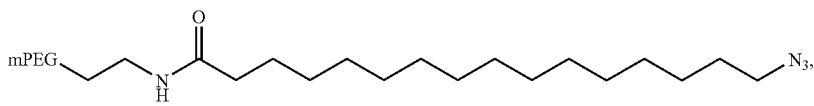
wherein mPEG has a molecular weight of 20 kDa,
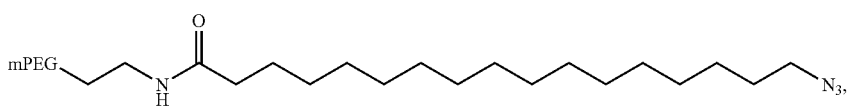

27 wherein mPEG has a molecular weight of 20 kDa,

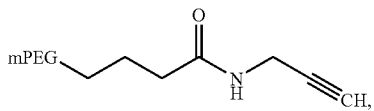

wherein mPEG has a molecular weight of 20 kDa,

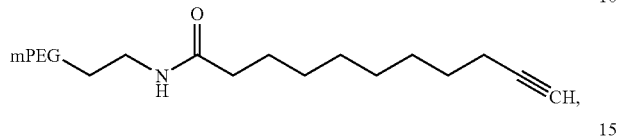

wherein mPEG has a molecular weight of 20 kDa,

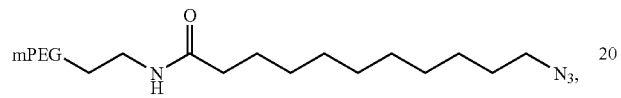

wherein mPEG has a molecular weight of 30 kDa,

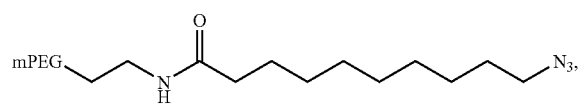

wherein mPEG has a molecular weight of 30 kDa,

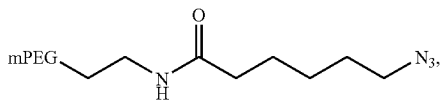

wherein mPEG has a molecular weight of 30 kDa,

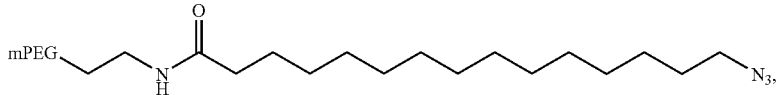

wherein mPEG has a molecular weight of 30 kDa,

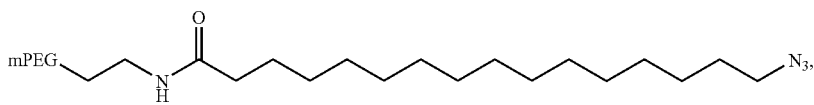

wherein mPEG has a molecular weight of 30 kDa,

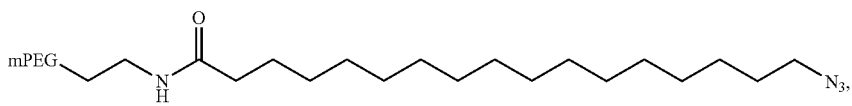

28 wherein mPEG has a molecular weight of 30 kDa,

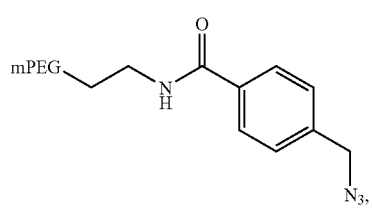

wherein mPEG has a molecular weight of 30 kDa,

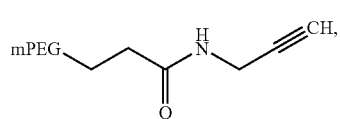

wherein mPEG has a molecular weight of 30 kDa,

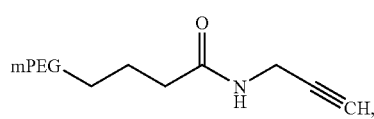

wherein mPEG has a molecular weight of 30 kDa,

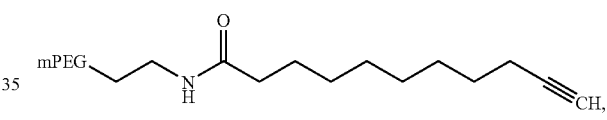

wherein mPEG has a molecular weight of 30 kDa,

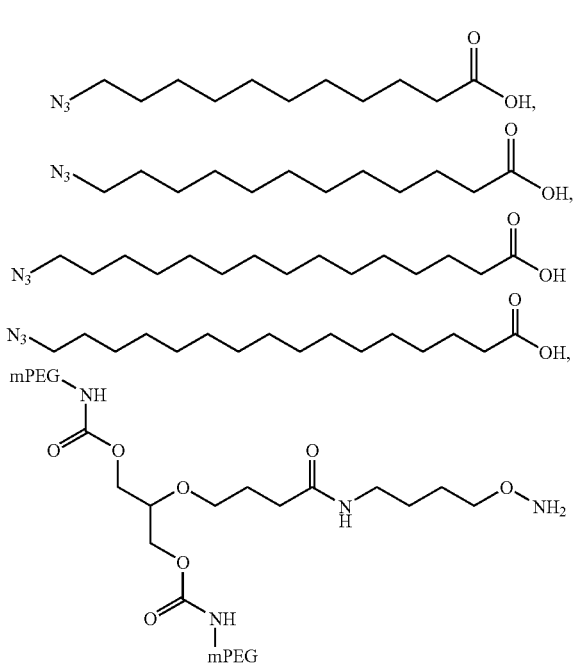

wherein mPEG has a molecular weight of 20 kDa,

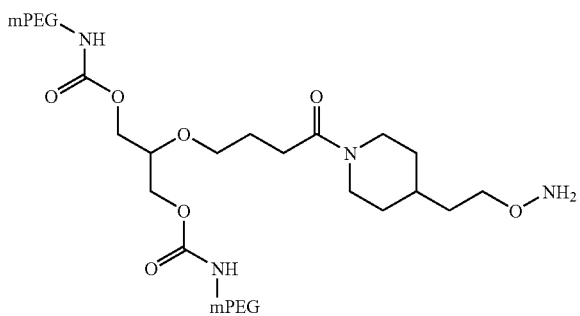

wherein mPEG has a molecular weight of 20 kDa, and

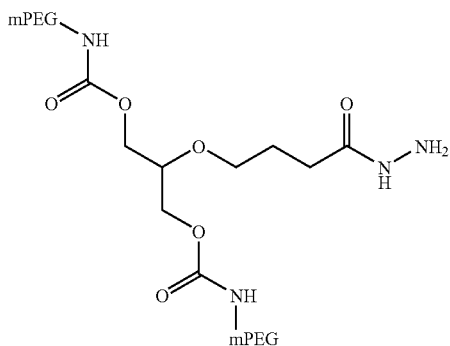

wherein mPEG has a molecular weight of 20 kDa.

As explained above, the catalytic action of carboxypeptidases causes the C-terminal amino acid residue to be exchanged with, e.g. the compound of the formula

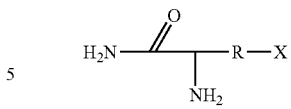

If it is desired to maintain the entire sequence of the peptide to be conjugated it is thus necessary to elongate the sequence of the peptide with one amino acid residue. Means for doing so are well-known to persons skilled in the art, e.g. by recombinant techniques or by protein synthetic methods. Another reason for wanting to elongate the sequence of the peptide could be to make the peptide a substrate for the particular carboxypeptidase at hand. As explained earlier, the difference between carboxypeptidases mainly resides with the kind of amino acid residue they are able to cleave off. It may thus be necessary to add one or more amino acid residue to make a given peptide a substrate for a given carboxypeptidase. The added amino acid residues may either be natural or unnatural.

It is recognised that some peptides, e.g. insulin and Factor VII, comprise more than one chain, which in turn means that they have more than one C-terminal. In some cases it might be possible to distinguish between the C-terminals by a proper selection of the carboxypeptidase used. In other cases it might be necessary to introduce a difference between the C-terminals, e.g. by adding or deleting one or more amino acid residues from one of the C-terminals to effect a conjugation at only a limited number of the C-terminals present. In still other cases it might be useful to conjugate the peptide at all C-terminals.

Any peptide can be conjugated by the methods of the present invention, such as e.g. enzymes, peptide hormones, growth factors, antibodies, cytokines, receptors, lymphokines and vaccine antigenes, and particular mentioning is made of therapeutic peptides, such as insulin, glucagon like-peptide 1 (GLP-1), glucagon like-peptide 2 (GLP-2), growth hormone, cytokines, trefoil factor peptides (TFF), peptide melanocortin receptor modifiers and factor VII compounds.

Particular applicable insulin is human insulin. In the present context the term "human insulin" refers to naturally produced insulin or recombinantly produced insulin. Recombinant human insulin may be produced in any suitable host cell, for example the host cells may be bacterial, fungal (including yeast), insect, animal or plant cells. Many insulin compounds have been disclosed in the literature, and they too are particular useful in the methods of the present invention. By "insulin compound" (and related expressions) is meant human insulin in which one or more amino acids have been deleted and/or replaced by other amino acids, including non-codeable amino acids, and/or human insulin comprising additional amino acids, i.e. more than 51 amino acids, and/or human insulin in which at least one organic substituent is bound to one or more of the amino acids.

The following patent documents are mentioned as disclosures of insulin compounds particular applicable in the methods provided by the present invention.

WO 97/31022 (Novo Nordisk), which is incorporated herein by reference, discloses insulin compounds with a protracted activity profile wherein the amino group of the N-terminal amino acid of the B-chain and/or the ε-amino group of $Lys^{B29}$ has a carboxylic acid containing lipophilic substituent. Particular mentioning is made of $N^{\epsilon B29}$—(CO—$(CH_2)_{14}$—COOH) human insulin; $N^{\epsilon B29}$—(CO—$(CH_2)_{16}$—COOH) human insulin; $N^{\epsilon B29}$—(CO—$(CH_2)_{18}$—COOH) human insulin; $N^{\epsilon B29}$—(CO—$(CH_2)_{20}$—COOH); $N^{\epsilon B29}$—(CO—

$(CH_2)_{22}$—COOH) human insulin; $N^{\epsilon B29}$—(CO—$(CH_2)_{14}$—COOH) Asp$^{B28}$-human insulin; $N^{\epsilon B29}$—(CO—$(CH_2)_{16}$—COOH) Asp$^{B28}$-human insulin; $N^{\epsilon B29}$—(CO—$(CH_2)_{18}$—COOH) Asp$^{B28}$-human insulin; $N^{\epsilon B29}$—(CO—$(CH_2)_{20}$—COOH) Asp$^{B28}$-human insulin; $N^{\epsilon B29}$—(CO—$(CH_2)_{22}$—COOH) Asp$^{B28}$-human insulin; $N^{\epsilon B30}$—(CO—$(CH_2)_{14}$—COOH) Thr$^{B29}$Lys$^{B30}$-human insulin; $N^{\epsilon B30}$—(CO—$(CH_2)_{16}$—COOH) Thr$^{B29}$Lys$^{B30}$-human insulin; $N^{\epsilon B30}$—(CO—$(CH_2)_{18}$—COOH) Thr$^{B29}$Lys$^{B30}$-human insulin; $N^{\epsilon B30}$—(CO—$(CH_2)_{20}$—COOH) Thr$^{B29}$Lys$^{B30}$-human insulin; $N^{\epsilon B30}$—(CO—$(CH_2)_{22}$—COOH) Thr$^{B29}$Lys$^{B30}$-human insulin;

$N^{\epsilon B28}$—(CO—$(CH_2)_{14}$—COOH) Lys$^{B28}$Pro$^{B29}$-human insulin; $N^{\epsilon B28}$—(CO—$(CH_2)_{16}$—COOH) Lys$^{B28}$Pro$^{B29}$-human insulin; $N^{\epsilon B28}$—(CO—$(CH_2)_{18}$—COOH) Lys$^{B28}$Pro$^{B29}$-human insulin; $N^{\epsilon B28}$—(CO—$(CH_2)_{20}$—COOH) Lys$^{B28}$Pro$^{B29}$-human insulin; $N^{\epsilon B28}$—(CO—$(CH_2)_{22}$—COOH) Lys$^{B28}$Pro$^{B29}$-human insulin; $N^{\epsilon B29}$—(CO—$(CH_2)_{14}$—COOH) desB30 human insulin; $N^{\epsilon B29}$—(CO—$(CH_2)_{16}$—COOH) desB30 human insulin; $N^{\epsilon B29}$—(CO—$(CH_2)_{18}$—COOH) desB30 human insulin; $N^{\epsilon B29}$—(CO—$(CH_2)_{20}$—COOH) desB30 human insulin; and $N^{\epsilon B29}$—(CO—$(CH_2)_{22}$COOH) desB30 human insulin.

WO 96/29344 (Novo Nordisk), which is incorporated herein by reference, discloses insulin compounds with a protracted activity profile wherein either the amino group of the N-terminal amino acid of the B-chain has a lipophilic substituent comprising from 12 to 40 carbon atoms attached, or wherein the carboxylic acid group of the C-terminal amino acid of the B-chain has a lipophilic substituent comprising from 12 to 40 carbon atoms attached.

WO 95/07931 (Novo Nordisk), which is incorporated herein by reference, discloses insulin compounds with a protracted activity profile, wherein the $\epsilon$-amino group of Lys$^{B29}$ has a lipophilic substituent. Particular mentioning is made of $N^{\epsilon B29}$-tridecanoyl des(B30) human insulin; $N^{\epsilon B29}$-tetraderanoyl des(B30) human insulin, $N^{\epsilon B29}$-decanoyl des(B30) human insulin, $N^{\epsilon B29}$-dodecanoyl des(B30) human insulin, $N^{\epsilon B29}$-tridecanoyl Gly$^{A21}$ des(B30) human insulin, $N^{\epsilon B29}$-tetradecanoyl Gly$^{A21}$ des(B30) human insulin, $N^{\epsilon B29}$-decanoyl Gly$^{A21}$ des(B30) human insulin, $N^{\epsilon B29}$-dodecanoyl Gly$^{A21}$ des(B30) human insulin, $N^{\epsilon B29}$-tridecanoyl Gly$^{A21}$ Gln$^{B3}$ des(B30) human insulin, $N^{\epsilon B29}$-tetradecanoyl Gly$^{A21}$ Gln$^{B3}$ des(B30) human insulin, $N^{\epsilon B29}$-decanoyl Gly$^{A21}$ Gln$^{B3}$ des(B30) human insulin, $N^{\epsilon B29}$-dodecanoyl Gly$^{A21}$ Gln$^{B3}$ des(B30) human insulin, $N^{\epsilon B29}$-tridecanoyl Ala$^{A21}$ des(B30) human insulin, $N^{\epsilon B29}$-tetradecanoyl Ala$^{A21}$ des(B30) human insulin, $N^{\epsilon B29}$-decanoyl Ala$^{A21}$ des(B30) human insulin, $N^{\epsilon B29}$-dodecanoyl Ala$^{A21}$ des(B30) human insulin, $N^{\epsilon B29}$-tridecanoyl Ala$^{A21}$ Gln$^{B3}$ des(B30) human insulin, $N^{\epsilon B29}$-tetradecanoyl Ala$^{A21}$ Gln$^{B3}$ des(B30) human insulin, $N^{\epsilon B29}$-decanoyl Ala$^{A21}$ Gln$^3$ des(B30) human insulin, $N^{\epsilon B29}$-dodecanoyl Ala$^{A21}$ Gln$^{B3}$ des(B30) human insulin, $N^{\epsilon B29}$-tridecanoyl Gln$^{B3}$ des(B30) human insulin, $N^{\epsilon B29}$-tetradecanoyl Gln$^{B3}$ des(B30) human insulin, $N^{\epsilon B29}$-decanoyl Gln$^{B3}$ des(B30) human insulin, $N^{\epsilon B29}$-dodecanoyl Gln$^{B3}$ des(B30) human insulin, $N^{\epsilon B29}$-tridecanoyl Gly$^{A21}$ human insulin, $N^{\epsilon B29}$-tetradecanoyl Gly$^{A21}$ human insulin, $N^{\epsilon B29}$-decanoyl Gly$^{A21}$ human insulin, $N^{\epsilon B29}$-dodecanoyl Gly$^{A21}$ human insulin, $N^{\epsilon B29}$-tridecanoyl Gly$^{A21}$ Gln$^{B3}$ human insulin, $N^{\epsilon B29}$-tetradecanoyl Gly$^{A21}$ Gln$^{B3}$ human insulin, $N^{\epsilon B29}$-decanoyl Gly$^{A21}$ Gln$^{B3}$ human insulin, $N^{\epsilon B29}$-dodecanoyl Gly$^{A21}$ Gln$^{B3}$ human insulin, $N^{\epsilon B29}$-tridecanoyl Ala$^{A21}$ human insulin, $N^{\epsilon B29}$-tetradecanoyl Ala$^{A21}$ human insulin, $N^{\epsilon B29}$-decanoyl Ala$^{A21}$ human insulin, $N^{\epsilon B29}$-dodecanoyl Ala$^{A21}$ human insulin, $N^{\epsilon B29}$-tridecanoyl Ala$^{A21}$ Gln$^{B3}$ human insulin, $N^{\epsilon B29}$-tetradecanoyl Ala$^{A21}$ Gln$^{B3}$ human insulin, $N^{\epsilon B29}$-decanoyl Ala$^{A21}$ Gln$^{B3}$ human insulin, $N^{\epsilon B29}$-dodecanoyl Ala$^{A21}$ Gln$^{B3}$ human insulin, $N^{\epsilon B29}$-tridecanoyl Gln$^{B3}$ human insulin, $N^{\epsilon B29}$-tetradecanoyl Gln$^{B3}$ human insulin, $N^{\epsilon B29}$-decanoyl Gln$^{B3}$ human insulin, $N^{\epsilon B29}$-dodecanoyl Gln$^3$ human insulin, $N^{\epsilon B29}$-tridecanoyl Glu$^{B30}$ human insulin, $N^{\epsilon B29}$-tetradecanoyl Glu$^{B30}$ human insulin, $N^{\epsilon B29}$-decanoyl Glu$^{B30}$ human insulin, $N^{\epsilon B29}$-dodecanoyl Glu$^{B30}$ human insulin, $N^{\epsilon B29}$-tridecanoyl Gly$^{A21}$ Glu$^{B30}$ human insulin, $N^{\epsilon B29}$-tetradecanoyl Gly$^{A21}$ Glu$^{B30}$ human insulin, $N^{\epsilon B29}$-decanoyl Gly$^{A21}$ Glu$^{B30}$ human insulin, $N^{\epsilon B29}$-dodecanoyl Gly$^{A21}$ Glu$^{B30}$ human insulin, $N^{\epsilon B29}$-tridecanoyl Gly$^{A21}$ Gln$^{B3}$ Glu$^{B30}$ human insulin, $N^{\epsilon B29}$-tetradecanoyl Gly$^{A21}$ Gln$^{B3}$ Glu$^{B30}$ human insulin, $N^{\epsilon B29}$-decanoyl Gly$^{A21}$ Gln$^{B3}$ Glu$^{B30}$ human insulin, $N^{\epsilon B29}$-dodecanoyl Gly$^{A21}$ Gln$^{B3}$ Glu$^{B30}$ human insulin, $N^{\epsilon B29}$-tridecanoyl Ala$^{A21}$ Glu$^{B30}$ human insulin, $N^{\epsilon B29}$-tetradecanoyl Ala$^{A21}$ Glu$^{B30}$ human insulin, $N^{\epsilon B29}$-decanoyl Ala$^{A21}$ Glu$^{B30}$ human insulin, $N^{\epsilon B29}$-dodecanoyl Ala$^{A21}$ Glu$^{B30}$ human insulin, $N^{\epsilon B29}$-tridecanoyl Ala$^{A21}$ Gln$^{B3}$ Glu$^{B30}$ human insulin, $N^{\epsilon B29}$-tetradecanoyl Ala$^{A21}$ Gln$^{B3}$ Glu$^{B30}$ human insulin, $N^{\epsilon B29}$-decanoyl Ala$^{A21}$ Gln$^{B3}$ Glu$^{B30}$ human insulin, $N^{\epsilon B29}$-dodecanoyl Ala$^{A21}$ Gln$^{B3}$ Glu$^{B30}$ human insulin, $N^{\epsilon B29}$-tridecanoyl Gln$^{B3}$ Glu$^{B30}$ human insulin, $N^{\epsilon B29}$-tetradecanoyl Gln$^{B3}$ Glu$^{B30}$ human insulin, $N^{\epsilon B29}$-decanoyl Gln$^{B3}$ Glu$^{B30}$ human insulin and $N^{\epsilon B29}$-dodecanoyl Gln$^{B3}$ Glu$^{B30}$ human insulin.

WO 97/02043 (Novo Nordisk), which is incorporated herein by reference discloses hormonally inactive insulin compounds which are useful in insulin prophylaxis, and in particular such analogues of human insulin are selected from amongst desA1 human insulin; des(A1-A2) human insulin; des(A1-A3) human insulin; desA21 human insulin; des(B1-B5) human insulin; des(B1-B6) human insulin; des(B23-B30) human insulin; des(B24-B30) human insulin; des(B25-B30) human insulin; Gly$^{A21}$ human insulin; Ala$^{A21}$ human insulin; $N^{\epsilon B29}$human insulin; Thr$^{A2}$ human insulin; Pro$^{A2}$ human insulin; D-allo IleA human insulin; $N^{\epsilon B29}$ human insulin; $N^{\epsilon B29}$ human insulin; Leu$^{A3}$ human insulin; Val$^{A2}$, Ile$^{A3}$ human insulin; Abu$^{A2}$, Abu$^{A3}$ human insulin; Gly$^{A2}$, Gly$^{A3}$ human insulin; D-Cys$^{A6}$ human insulin; D-Cys$^{A6}$, D-Cys$^{A11}$ human insulin; Ser$^{A6}$, Ser$^{A11}$, des(A8-A10) human insulin; D-Cys$^{A7}$ human insulin; D-Cys$^{A11}$ human insulin; Leu$^{A19}$ human insulin; Gly$^{B6}$ human insulin; Glu$^{B12}$ human insulin; Asn$^{B12}$ human insulin; Phe$^{B12}$ human insulin; D-Ala$^{B12}$ human insulin; and Asp$^{B25}$ human insulin are applicable in the methods of the present invention.

WO 92/15611 (Novo nordisk), which is incorporated herein by reference, discloses analogues of human insulin with a fast association rate constants in the insulin receptor binding process and characterised by comprising a tyrosine in position A13 and/or a phenylalanin, tryptophane or tyrosine in position B17. In particular, such analogues are selected from amongst TyrA$^{13}$ human insulin, Phe$^{B17}$ human insulin, Trp$^{B17}$ human insulin, Tyr$^{B17}$ human insulin, Tyr$^{A13}$, Phe$^{B17}$ human insulin, Tyr$^{A13}$, Trp$^{B17}$ human insulin, Tyr$^{A13}$, Tyr$^{B17}$ human insulin, Phe$^{A13}$, Phe$^{B17}$ human insulin, Phe$^{A13}$, Trp$^{B17}$ human insulin, Phe$^{A13}$, Tyr$^{B17}$ human insulin, Trp$^{A13}$, Phe$^{B17}$ human insulin, Trp$^{A13}$, Trp$^{B17}$ human insulin and Trp$^{A13}$, Tyr$^{B17}$ human insulin.

WO 92/00322 (Novo Nordisk), which is incorporated herein by reference, discloses analogues of human insulin which are capable of being targeted to specific tissues, and which are characterized by having in the A13 position and/or in the B17 position in the insulin molecule a naturally occurring amino acid residue different from leucine and/or by having in the B18 position in the insulin molecule a naturally occurring amino acid residue different from valine. In particular, such analogues are selected from amongst Ala$^{B17}$ human insulin, Ala$^{B18}$ human insulin, Asn$^{A13}$ human insulin, Asn$^{A13}$, Ala$^{B17}$human insulin, Asn$^{A13}$, Asp$^{B17}$ human insulin, Asn$^{A13}$, Glu$^{B17}$ human insulin, Asn$^{B18}$ human insulin, Asp$^{A13}$ human insulin, Asp$^{A13}$, Ala$^{B17}$ human insulin, Asp$^{A13}$, Asp$^{B17}$ human insulin, Asp$^{A13}$, Glu$^{B17}$ human insulin, Asp$^{B18}$ human insulin, Gln$^{A13}$ human insulin, Gln$^{A13}$, Ala$^{B17}$ human insulin, Gln$^{A13}$, Asp$^{B17}$ human insulin, Gln$^{B18}$ human insulin, Glu$^{A13}$ human insulin, Glu$^{A13}$, Ala$^{B17}$ human insulin, Glu$^{A13}$, Asp$^{B17}$ human insulin, Glu$^{A13}$, Glu$^{B17}$ human insulin, Glu$^{B18}$ human insulin, Gly$^{A13}$ human insulin, Gly$^{A13}$, Ala$^{B17}$ human insulin, Gly$^{A13}$, Asn$^{B17}$ human insulin, Gly$^{A13}$, Asp$^{B17}$ human insulin, Gly$^{A13}$, Glu$^{B17}$ human insulin, Gly$^{B18}$ human insulin, Ser$^{A13}$ human insulin, Ser$^{A13}$, Gln$^{A17}$, Glu$^{B10}$, Gln$^{B17}$-des(Thr$^{B30}$) human insulin, Ser$^{A13}$, Ala$^{B17}$ human insulin, Ser$^{A13}$, Asn$^{B17}$ human insulin, Ser$^{A13}$, Asp$^{B17}$ human insulin, Ser$^{A13}$, Gln$^{B17}$ human insulin, Ser$^{A13}$, Glu$^{B17}$ human insulin, Ser$^{A13}$, Thr$^{B17}$ human insulin, Ser$^{A14}$, Asp$^{B17}$ human insulin, Ser$^{B18}$ human insulin, Thr$^{A13}$ human insulin or Thr$^{B18}$ human insulin.

WO 90/01038 (Novo Nordisk), which is incorporated herein by reference, discloses analogues of human insulin with high biological activity and characterized by having Phe$^{B25}$ substituted by His or Tyr, by having substitutions in one or more of positions A4, A8, A17, A21, B9, B10, B12, B13, B21, B26, B27, B28 and B30, and by having the amino acid residue at position B30 optionally absent. In particular, such analogues are selected from amongst Tyr$^{B25}$ human insulin, Tyr$^{B25}$, Asp$^{B28}$ human insulin, His$^{B25}$ human insulin, His$^{B25}$, Asp$^{B28}$ human insulin, Tyr$^{B25}$ human insulin-B30-amide and His$^{B25}$ human insulin-B30-amide.

WO 86/05496 (Nordisk Gentofte) discloses analogues of human insulin with a protracted action and characterized by having a blocked B30 carboxylic group, and by having one to four blocked carboxylic groups in the amino acid residues at positions A4, A17, A21, B13 and B21. In particular, such analogues are selected from amongst insulin-B30-octyl ester, insulin-B30-dodecyl amide, insulin-B30-hexadecyl amide, insulin-(B21,B30)-dimethyl ester, insulin-(B17,B30)-dimethyl ester, insulin-(A4,B30) diamide, insulin-A17amide-B30-octyl ester, insulin-(A4,B13) diamide-B30-hexylamide, insulin-(A4,A17,B21,B30)-tetraamide, insulin-(A17,B30)-diamide, A4-Ala-insulin-B30-amide and B30-Leu-insulin-(A4,B30)-diamide.

WO 86/05497 (Nordisk Gentofte), which is incorporated herein by reference, discloses insulin compounds in which one or more of the four amino acid residues in positions A4, A17, B13 and B21 comprises an uncharged side chain. Particular mentioning is made of human insulin A17-Gln, human insulin A4-Gln, porcine insulin B21-Gln, human insulin B13-Gln, human insulin (A17,B21 Gln, human insulin A4-Ala, human insulin B21-Thr, human insulin B13-Val, human insulin-Thr-A17-Gln, human insulin B21-methyl ester and human insulin A17-methyl ester.

WO 92/00321 (Novo Nordisk), which is incorporated herein by reference, discloses insulin compounds with prolonged activity wherein a positive charge in the N-terminal end of the B-chain has been introduced. Particular mentioning is made of Arg$^{B5}$, Ser$^{A21}$, Thr$^{B30}$-NH$_2$ human insulin, Arg$^{B5}$, Pro$^{B6}$, Ser$^{A21}$, Thr$^{B3}$-NH$_2$ human insulin, Arg$^{B5}$, Gly$^{A21}$, Thr$^{B30}$-NH$_2$ human insulin, Arg$^{B5}$, Pro$^{B6}$, Gly$^{A21}$, Thr$^{B30}$-NH$_2$ human insulin, Arg$^{B2}$, Ser$^{A21}$, Thr$^{B30}$-NH$_2$ human insulin, Arg$^{B2}$, Pro$^{B3}$, Ser$^{A21}$, Thr$^{B30}$-NH$_2$ human insulin, Arg$^{B2}$, Gly$^{A21}$, Thr$^{B30}$-NH$_2$ human insulin, Arg$^{B2}$, Pro$^{B3}$, Gly$^{A21}$, Thr$^{B30}$-NH$_2$ human insulin, Arg$^{B2}$, Arg$^{B3}$, Ser$^{A21}$, Thr$^{B30}$-NH$_2$ human insulin, Arg$^{B2}$, Ser$^{A21}$ human insulin, Arg$^{B4}$, Pro$^{B5}$, Ser$^{A21}$, Thr$^{B30}$-NH$_2$ human insulin, Arg$^{B4}$, Pro$^{B6}$, Gly$^{A21}$, Thr$^{B30}$ human insulin, Arg$^{B3}$, Gly$^{A21}$, Thr$^{B30}$-NH$_2$ human insulin, Arg$^{B3}$, Ser$^{A21}$, Thr$^{B30}$-NH$_2$ human insulin, Arg$^{B4}$, Gly$^{A21}$, Thr$^{B3}$-NH$_2$ human insulin, Arg$^{B4}$, Ser$^{A21}$, Thr$^{B30}$-NH$_2$ human insulin and Arg$^{B1}$, Pro$^{B2}$, Gly$^{A21}$, Thr$^{B30}$-NH$_2$ human insulin.

WO 90/07522 (Novo Nordisk), which is incorporated herein by reference, discloses insulin compounds exhibiting a low ability to associate in solution wherein there is a positively charged amino acid residue, i.e. Lys or Arg in the position B28. Particular mentioning is made of des[Phe$^{B25}$]-human insulin, des[Tyr$^{B26}$]-human insulin, des[Thr$^{B27}$]-human insulin, des[Pro$^{B28}$]-human insulin, des[Phe$^{B25}$]-porcine insulin, des[Pro$^{B28}$]-porcine insulin, des[Pro$^{B28}$]-rabbit insulin, des[Phe$^{B25}$], des[Thr$^{B30}$]-human insulin, des[Tyr$^{B26}$], des[Thr$^{B30}$]-human insulin, [Ser$^{A21}$]-des[Pro$^{B28}$]-human insulin, [Gly$^{A21}$]-des[Pro$^{B28}$]-human insulin, [Gly$^{A21}$]-des[Phe$^{B25}$]-human insulin, [Asp$^{A21}$]-des[Phe$^{B25}$]-human insulin, [His$^{B25}$]-des[Tyr$^{B26}$], des[Thr$^{B30}$]-human insulin, [Asn$^{B21}$]-des[Tyr$^{B26}$],des[Thr$^{B30}$]-human insulin, [Asp$^{A21}$]-des[Phe B25], des[Thr$^{B30}$]-human insulin, [Asp$^{B28}$]-des[Phe$^{B25}$]-human insulin, [Asp$^{B3}$]-des[Phe$^{B25}$]-human insulin, [Lys$^{B28}$]-human insulin, [Lys$^{B28}$, Thr$^{B29}$]-human insulin and [Arg$^{B28}$]-des[Lys$^{B29}$]-human insulin.

WO 90/11290 (Novo Nordisk), which is incorporated herein by reference discloses insulin compounds with a prolonged activity. Particular mentioning is made of [Arg$^{A0}$]-human insulin-(B30-amide), [Arg$^{A0}$, Gln$^{B13}$]-human insulin-(B30-amide), [Arg$^{A0}$, Gln$^{A4}$, Asp$^{A21}$]-human insulin-(B30-amide), [Arg$^{A0}$, Ser$^{A21}$]-human insulin-(B30-amide) and [Arg$^{A0}$, Arg$^{B27}$]-des[Thr$^{B30}$]-human insulin.

WO 90/10645 (Novo Nordisk), which is incorporated herein by reference discloses glycosylated insulins. Particular mentioning is made of Phe(B1) glucose human insulin, Phe(B1) mannose human insulin, Gly(A1) mannose human insulin, Lys(B29) mannose human insulin, Phe(B1) galactose human insulin, Gly(A1) galactose human insulin, Lys(B29) galactose human insulin, Phe(B1) maltose human insulin, Phe(B1) lactose human insulin, Gly(A1) glucose human insulin, Gly(A1) maltose human insulin, Gly(A1) lactose human insulin, Lys(B29) glucose human insulin, Lys(B29) maltose human insulin, Lys(B29) lactose human insulin, Gly (A1), Phe(B1) diglucose human insulin, Gly(A1), Lys(B29) diglucose human insulin, Phe(B1), Lys(B29) diglucose human insulin, Phe(B1) isomaltose human insulin, Gly(A1) isomaltose human insulin, Lys(B29) isomaltose human insulin, Phe(B1) maltotriose human insulin, Gly(A1) maltotriose human insulin, Lys(B29) maltotriose human insulin, Gly (A1), Phe(B1) dimaltose human insulin, Gly(A1), Lys(B29) dimaltose human insulin, Phe(B1), Lys(B29) dimaltose human insulin, Gly(A1), Phe(B1) dilactose human insulin, Gly(A1), Lys(B29) dilactose human insulin, Phe(B1), Lys (B29) dilactose human insulin, Gly(A1), Phe(B1) dimaltotriose human insulin, Gly(A1), Lys(B29) dimaltotriose human insulin, Phe(B1), Lys(B29) dimaltotriose human insulin, Phe (B1), Gly(A1) dimannose human insulin, Phe(B1), Lys(B29) dimannose human insulin, Gly(A1), Lys(B29) dimannose human insulin, Phe(B1), Gly(A1) digalactose human insulin, Phe(B1), Lys(B29) digalactose human insulin, Gly(A1), Lys(B29) digalactose human insulin, Phe(B1), Gly(A1) diisomaltose human insulin, Phe(B1), Lys(B29) diisomaltose human insulin, Gly(A1), Lys(B29) diisomaltose human insulin, Phe(B1) glucose [Asp$^{B10}$] human insulin and Gly(A1), Phe(B1) diglucose [Asp$^{B10}$] human insulin.

WO 88/065999 (Novo Nordisk), which is incorporated herein by reference, discloses stabilized insulin compounds, wherein Ans$^{21A}$ has been substituted with other amino acid residues. Particular mentioning is made of Gly$^{A21}$ human insulin, Ala$^{A21}$ human insulin, Ser$^{A21}$ human insulin, Thr$^{A21}$ human insulin and hSer$^{A21}$ human insulin.

EP 254516 (Novo Nordisk), which is incorporated herein by reference, discloses insulin compounds with a prolonged action, wherein basic amino acid residues have been substituted by neutral amino acid residues. Particular mentioning is made of $Gly^{A21}$, $Lys^{B27}$, $Thr^{B30}$-$NH_2$ human insulin, $Ser^{A21}$, $Lys^{B27}$, $Thr^{B30}$-$NH_2$ human insulin, $Thr^{A21}$, $Lys^{B27}$, $Thr^{B30}$-$NH_2$ human insulin, $Ala^{B21}$, Lys 27, $Thr^{B30}$-$NH_2$ human insulin, $His^{A21}$, $Lys^{B27}$, $Thr^{B30}$-$NH_2$ human insulin, $Asp^{B21}$, $Lys^{B27}$, $Thr^{B30}$-$NH_2$ human Insulin, $Gly^{A21}$, $Arg^{B21}$, $Thr^{B30}$-$NH_2$ human insulin, $Ser^{A21}$, $Arg^{B27}$, $Thr^{B30}$-$NH_2$ human insulin, $Thr^{A21}$, $Arg^{B27}$, $Thr^{B30}$-$NH_2$ human insulin, $Ala^{B21}$, $Arg^{B27}$, $Thr^{B30}$-$NH_2$ human insulin, $His^{A21}$, $Arg^{B27}$, $Thr^{B30}$-$NH_2$ human insulin, $Asp^{B21}$, $Arg^{B27}$, $Thr^{B30}$-$NH_2$ human insulin, $Gln^{B13}$, $Gly^{A21}$, $Arg^{B27}$, $Thr^{B30}$-$NH_2$ human insulin, $Gln^{B13}$, $Ser^{A21}$, $Thr^{B30}$-$NH_2$ human insulin, $Gln^{B13}$, $Ser^{A21}$, $Arg^{B27}$, $Thr^{B30}$-$NH_2$ human insulin, $Gln^{B13}$, $Thr^{A21}$, $Arg^{B27}$, $Thr^{B30}$-$NH_2$ human insulin, $Gln^{B13}$, $Ala^{A21}$, $Arg^{B27}$, $Thr^{B30}$-$NH_2$ human insulin, $Gln^{B13}$, $His^{A21}$, $Arg^{B27}$, $Thr^{B30}$-$NH_2$ human insulin, $Gln^{B13}$, $Asp^{A21}$, $Arg^{B27}$, $Thr^{B30}$-$NH_2$ human insulin, $Gln^{B13}$, $Gly^{A21}$, $Lys^{B27}$, $Thr^{B30}$-$NH_2$ human insulin, $Gln^{B13}$, $Ser^{A21}$, $Lys^{B27}$, $Thr^{B30}$-$NH_2$ human insulin, $Gln^{B13}$, $Thr^{A21}$, $Lys^{B27}$, $Thr^{B30}$-$NH_2$ human insulin, $Gln^{B13}$, $Ala^{A21}$, $Lys^{B27}$, $Thr^{B30}$-$NH_2$ human insulin, $Gln^{B13}$, $His^{A21}$, $Lys^{B27}$, $Thr^{B30}$-$NH_2$ human insulin, $Gln^{B13}$, $Aps^{A21}$, $Lys^{B27}$, $Thr^{B30}$-$NH_2$ human insulin, $Asn^{A21}$, $Lys^{B27}$ human insulin, $Ser^{A21}$, $Lys^{B27}$ human insulin, $Thr^{A21}$, $Lys^{B27}$ human insulin, $Ala^{A21}$, $Lys^{B27}$ human insulin, $His^{A21}$, $Lys^{B27}$ human insulin, $Asp^{A21}$, $Lys^{B27}$ human insulin, $Gly^{A21}$, $Lys^{B27}$ human insulin, $Asn^{A21}$, $Arg^{B27}$ human insulin, $Ser^{A21}$, $Arg^{B27}$ human insulin, $Thr^{A21}$, $Arg^{B27}$ human insulin, $Ala^{A21}$, $Arg^{B27}$ human insulin, $His^{A21}$, $Arg^{B27}$ human insulin, $Asp^{A21}$, $Arg^{B27}$ human insulin, $Gly^{A21}$, $Arg^{B27}$ human insulin, $Gln^{A17}$, $Asn^{A21}$, $Arg^{B27}$ human insulin, $Gln^{A17}$, $Ser^{A21}$, $Arg^{B27}$ human insulin, $Gln^{A17}$, $Thr^{A21}$, $Arg^{B27}$ human insulin, $Gln^{A17}$, $Ala^{A21}$, $Arg^{B27}$ human insulin, $Gln^{A17}$, $His^{A21}$, $Arg^{B27}$ human insulin, $Gln^{A17}$, $Asp^{A21}$ $Arg^{B27}$ human insulin, $Gln^{A17}$, $Gly^{A21}$, $Arg^{B27}$ human insulin, $Gln^{A17}$, $Asn^{A21}$, $Gln^{B13}$ human insulin, $Gln^{A17}$, $Ser^{A21}$, $Gln^{B13}$ human insulin, $Gln^{A17}$, $Thr^{A21}$, $Gln^{B13}$ human insulin, $Gln^{A17}$, $Ala^{A21}$, $Gln^{B13}$ human insulin, $Gln^{A17}$, $His^{A21}$, $Gln^{B13}$ human insulin, $Gln^{A17}$, $Asp^{A21}$, $Gln^{B13}$ human insulin, $Gln^{A17}$, $Gly^{A21}$, $Gln^{B13}$ human insulin, $Arg^{A27}$, $Asn^{A21}$, $Gln^{B13}$ human insulin, $Arg^{A27}$, $Ser^{A21}$, $Gln^{B13}$ human insulin, $Arg^{A27}$, $Thr^{A21}$, $Gln^{B13}$ human insulin, $Arg^{A27}$, $Ala^{A21}$, $Gln^{B13}$ human insulin, $Arg^{A27}$, $His^{A21}$, $Gln^{B13}$ human insulin, $Arg^{A27}$, $Asp^{A21}$, $Gln^{B13}$ human insulin, $Arg^{A27}$, $Gly^{A21}$, $Gln^{B13}$ human insulin, $Gln^{A17}$, $Asn^{A21}$, $Lys^{B27}$ human insulin, $Gln^{A17}$, $Ser^{A21}$, $Lys^{B27}$ human insulin, $Gln^{A17}$, $Thr^{B13}$, $Lys^{B27}$ human insulin, $Gln^{A17}$, $Ala^{A21}$, $Lys^{B27}$ human insulin, $Gln^{A17}$, $His^{A21}$, $Lys^{B27}$ human insulin, $Gln^{A17}$, $Asp^{A21}$, $Lys^{B27}$ human insulin, $Gln^{A17}$, $Gly^{A21}$, $Lys^{B27}$ human insulin, $Gln^{B13}$, $Asn^{A21}$, $Lys^{B27}$ human insulin, $Gln^{B13}$, $Ser^{A21}$, $Lys^{B27}$ human insulin, $Gln^{B13}$, $Thr^{A21}$, $Lys^{B27}$ human insulin, $Gln^{B13}$, $Ala^{A21}$, $Lys^{B27}$ human insulin, $Gln^{B13}$, $His^{A21}$, $Lys^{B27}$ human insulin, $Gln^{B13}$, $Asp^{A21}$, $Lys^{B27}$ human insulin, and $Gln^{B13}$, $Gly^{A21}$, $Lys^{B27}$ human insulin.

EP 214826 (Novo Nordisk), which is incorporated herein by reference, discloses rapid on-set insulin compounds.

EP 194864 (Novo Nordisk), which is incorporated herein by reference, discloses insulin compounds with a prolonged action, wherein basic amino acid residues have been substituted by neutral amino acid residues. Particular mentioning is made of $Gln^{A17}$, $Arg^{B27}$, $Thr^{B30}$-$NH_2$ human insulin, $Gln^{A17}$, $Gln^{B13}$, $Thr^{B30}$-$NH_2$ human insulin, $Gln^{A17}$, $Lys^{B27}$, $Thr^{B30}$-$NH_2$ human insulin, $Gln^{A17}$, $Lys^{B27}$-$NH_2$ human insulin, $Gln^{A17}$, $Thr^{B30}$-$NH_2$ human insulin, $Gln^{B13}$, $Arg^{B27}$, $Thr^{B30}$-$NH_2$ human insulin, $Gln^{B13}$ $Lys^{B27}$, $Thr^{B30}$-$NH_2$ human insulin, $Gln^{B13}$, $Lys^{B30}$-$NH_2$ human insulin, $Gln^{B13}$, $Thr^{B30}$-$NH_2$ human insulin, $Arg^{B27}$, $Arg^{B30}$-$NH_2$ human insulin, $Arg^{B27}$, $Lys^{B30}$-$NH_2$ human insulin, $Arg^{B27}$, $Thr^{B30}$-$NH_2$ human insulin, $Lys^{B27}$, $Arg^{B30}$-$NH_2$ human insulin, $Lys^{B27}$, $Lys^{B30}$-$NH_2$ human insulin, $Lys^{B27}$, $Thr^{B30}$-$NH_2$ human insulin, $Lys^{B29}$-$NH_2$, des-(B30)human insulin, $Thr^{B30}$-$NH_2$ human insulin, $Lys^{B30}$-$NH_2$ human insulin, $Lys^{B30}$(Lau)-$NH_2$ human insulin, $Lys^{B30}$, $Arg^{B31}$-$NH_2$ human insulin, $Lys^{B30}$, $Lys^{B31}$-$NH_2$ human insulin, $Arg^{B30}$-$NH_2$ human insulin, $Arg^{B30}$, $Arg^{B31}$-$NH_2$ human insulin, and $Arg^{B30}$, $Lys^{B31}$-$NH_2$ human insulin.

U.S. Pat. No. 3,528,960 (Eli Lilly), which is incorporated herein by reference, discloses N-carboxyaroyl insulin compounds in which one, two or three primary amino groups of the insulin molecule has a carboxyaroyl group.

GB Patent No. 1.492.997 (Nat. Res. Dev. Corp.), which is incorporated herein by reference, discloses insulin compounds with a carbamyl substitution at $N^{\epsilon B29}$ with an improved profile of hypoglycaemic effect.

JP laid-open patent application No. 1-254699 (Kodama Co., Ltd.), which is incorporated herein by reference, discloses insulin compounds, wherein an alkanoyl group is bound to the amino group of $Phe^{B1}$ or to the $\epsilon$-amino group of $Lys^{B29}$ or to both of these.

JP laid-open patent applicaton No. 57-067548 (Shionogi), which is incorporated herein by reference discloses insulin compounds, in which the B30 position have an amino acid having at least five carbon atoms which cannot necessarily be coded for by a triplet of nucleotides.

WO 03/053339 (Eli Lilly), which is incorporated herein by reference, disclose insulin compounds, wherein the A-chain in the N-terminal has been extended with two amino acid residues, A-1 and A0, wherein the B-chain has been extended at the N-terminal with two amino acid residues, B-1 and B0, wherein the amino acid residues at positions B28, B29 and B39 may be substituted, and wherein the $\epsilon$-amino group of Lys at position B28 or B29 is covalently bound to the x-carboxyl group of a positively charged amino acid to form a Lys-$N^{\epsilon}$-aminoacid derivative. Particular mentioning is made of said analogues, wherein A-1 and B-1 are both absent, and wherein A0 represent Arg and B0 represents Arg or is absent.

Insulin compounds selected from the group consisting of
i. An analogue wherein position B28 is Asp, Lys, Leu, Val, or Ala and position B29 is Lys or Pro; and
ii. des(B28-B30), des(B27) or des(B30) human insulin.

are also applicable for the methods of the present invention, and in particular, the insulin compound wherein position B28 is Asp or Lys, and position B29 is Lys or Pro.

des(B30) human insulin is also applicable in the methods of the present invention.

Other applicable insulin compounds are selected from the group consisting of B29-$N^{\epsilon}$-myristoyl-des(B30) human insulin, B29-$N^{\epsilon}$-palmitoyl-des(B30) human insulin, B29-$N^{\epsilon}$-myristoyl human insulin, B29-$N^{\epsilon}$-palmitoyl human insulin, B28-$N^{\epsilon}$-myristoyl $Lys^{B28}$ $Pro^{B29}$ human insulin, B28-$N^{\epsilon}$-palmitoyl $Lys^{B28}$ $Pro^{B29}$ human insulin, B30-$N^{\epsilon}$-myristoyl-$Thr^{B29}Lys^{B30}$ human insulin, B30-$N^{\epsilon}$-paimitoyl-$Thr^{B29}Lys^{B30}$ human insulin, B29-N-(N-palmitoyl-$\gamma$-glutamyl)-des(B30) human insulin, B29-$N^{\epsilon}$-(N-lithocholyl-$\gamma$-glutamyl)-des(B30) human insulin, B29-$N^{\epsilon}$-($\omega$-carboxyheptadecanoyl)-des(B30) human insulin, B29-$N^{\epsilon}$-($\omega$-carboxyheptadecanoyl) human insulin and B29-$N^{\epsilon}$-myristoyl-des(B30) human insulin.

Examples of GLP-1 applicable in the methods of the present invention include human GLP-1 and GLP-1 compounds. Human GLP-1 is a 37 amino acid residue peptide originating from preproglucagon which is synthesised i.a. in the L-cells in the distal ileum, in the pancreas and in the brain.

GLP-1 is an important gut hormone with regulatory function in glucose metabolism and gastrointestinal secretion and metabolism. Processing of preproglucagon to give GLP-1(7-36)-amide, GLP-1(7-37) and GLP-2 occurs mainly in the L-cells. The fragments GLP-1(7-36)-amide and GLP-1(7-37) are both glucose-dependent insulinotropic agents. In the past decades a number of structural analogues of GLP-1 were isolated from the venom of the Gila monster lizards (*Heloderma suspectum* and *Heloderma horridum*). Exendin-4 is a 39 amino acid residue peptide isolated from the venom of *Heloderma horridum*, and this peptide shares 52% homology with GLP-1. Exendin-4 is a potent GLP-1 receptor agonist which has been shown to stimulate insulin release and ensuring lowering of the blood glucose level when injected into dogs. The group of GLP-1(1-37) and exendin-4(1-39) and certain fragments, analogues and derivatives thereof (designated GLP-1 compounds herein) are potent insulinotropic agents, and they are all applicable in the method of the present invention. Insulinotropic fragments of GLP-1(1-37) are insulinotropic peptides for which the entire sequence can be found in the sequence of GLP-1(1-37) and where at least one terminal amino acid has been deleted. Examples of insulinotropic fragments of GLP-1(1-37) are GLP-1(7-37) wherein the amino acid residues in positions 1-6 of GLP-1(1-37) have been deleted, and GLP-1(7-36) where the amino acid residues in position 1-6 and 37 of GLP-1(1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogs of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogs of GLP-1(1-37) is e.g. Met$^8$-GLP-1(7-37) wherein the alanine in position 8 has been replaced by methionine and the amino acid residues in position 1 to 6 have been deleted, and Arg$^{34}$-GLP-1(7-37) wherein the valine in position 34 has been replaced with arginine and the amino acid residues in position 1 to 6 have been deleted. An example of an insulinotropic analog of exendin-4(1-39) is Ser$^2$Asp$^3$-exendin-4(1-39) wherein the amino acid residues in position 2 and 3 have been replaced with serine and aspartic acid, respectively (this particular analog also being known in the art as exendin-3). Insulinotropic derivatives of GLP-1(1-37), exendin-4(1-39) and analogs thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogs thereof are GLP-1(7-36)-amide, Arg$^{34}$, Lys$^{26}$(N$^\epsilon$-(γ-Glu(N$^\alpha$-hexadecanoyl)))-GLP-1(7-37) and Tyr$^{31}$-exendin-4(1-31)-amide. Further examples of GLP-1(1-37), exendin-4(1-39), insulinotropic fragments thereof, insulinotropic analogs thereof and insulinotropic derivatives thereof are described in WO 98/08871, WO 99/43706, U.S. Pat. No. 5,424,286 and WO 00/09666, which are all enclosed herein by reference.

GLP-2 and GLP-2 compounds may also be modified by the methods provided by the present invention. In the present context a GLP-2 compound binds to a GLP-2 receptor, preferably with an affinity constant ($K_D$) or a potency ($EC_{50}$) of below 1 μM, e.g. below 100 nM. The term "GLP-2 compound" is intended to indicate human GLP-2 in which one or more amino acid residue has been deleted and/or replaced by another amino acid residue, natural or unnatural, and/or human GLP-2 comprising additional amino acid residues, and/or human GLP-2 in which at least one organic substituent is bound to one or more of the amino acid residues. In particular, those peptides are considered, which amino acid sequence exhibit at any sequence of 33 consecutive amino acids more than 60% of the amino acid sequence of human GLP-2. Also those peptides are considered, which amino acid sequence exhibit at any sequence of 37 consecutive amino acids more than 60% of the amino acid sequence of human GLP-2 when up to four amino acids are deleted from the amino acid sequence. Also those peptides are considered, which amino acid sequence exhibit at any sequence of 31 consecutive amino acids more than 60% of the amino acid sequence of GLP-2, when up to two amino acids are added to their amino acid sequence. The term "GLP compounds" also includes natural allelic variations that may exist and occur from one individual to another. Also, degree and location of glycosylation or other post-translation modifications may vary depending on the chosen host cells and the nature of the host cellular environment.

Candidate GLP-2 compounds, which may be used according to the present invention include the GLP-2 compounds described in WO 96/32414, WO 97/39031, WO 98/03547, WO 96/29342, WO 97/31943, WO 98/08872, which are all incorporated herein by reference.

In particular, the following GLP-2 compounds are applicable in the methods of the present invention: A2G-GLP-2(1-33); K30R-GLP-2(1-33); S5K-GLP-2(1-33); S7K-GLP-2(1-33); D8K-GLP-2(1-33); E9K-GLP-2(1-33); M10K-GLP-2(1-33); N11K-GLP-2(1-33); T12K-GLP-2(1-33); I13K-GLP-2(1-33); L14K-GLP-2(1-33); D15K-GLP-2(1-33); N16K-GLP-2(1-33); L17K-GLP -2(1-33); A18K-GLP-2(1-33); D21K-GLP-2(1-33); N24K-GLP-2(1-33); Q28K-GLP-2(1-33); S5K/K30R-GLP-2(1-33); S7K/K30R-GLP-2(1-33); D8K/K30R-GLP-2(1-33); E9K/K30R-GLP-2(1-33); M10K/K30R-GLP-2(1-33); N11K/K30R-GLP-2(1-33); T12K/K30R-GLP-2(1-33); I13K/K30R -GLP-2(1-33); L14K/K30R-GLP-2(1-33); D15K/K30R-GLP-2(1-33); N16K/K30R-GLP-2(1-33); L17K/K30R-GLP-2(1-33); A18K/K30R-GLP-2(1-33); D21K/K30R-GLP-2(1-33); N24K/K30R -GLP-2(1-33); Q28K/K30R-GLP-2(1-33); K30R/D33K-GLP-2(1-33); D3E/K30R/D33E-GLP-2(1-33); D3E/S5K/K30R/D33E-GLP-2(1-33); D3E/S7K/K30R/D33E-GLP-2(1-33); D3E/D8K/K30R/D33E-GLP-2(1-33); D3E/E9K/K30R/D33E-GLP-2(1-33); D3E/M10K/K30R/D33E-GLP-2(1-33); D3E/N11K/K30R/D33E-GLP-2(1-33); D3E/T12K/K30R/D33E-GLP-2(1-33); D3E/I13K/K30R/D33E-GLP-2(1-33); D3E/L14K/K30R/D33E-GLP-2(1-33); D3E/D15K/K30R/D33E-GLP-2(1-33); D3E/N16K/K30R/D33E-GLP-2(1-33); D3E/L17K/K30R/D33E-GLP-2(1-33); D3E/A18K/K30R/D33E-GLP-2(1-33); D3E/D21K/K30R/D33E-GLP-2(1-33); D3E/N24K/K30R/D33E-GLP-2(1-33); and D3E/Q28K/K30R/D33E-GLP-2(1-33).

In one embodiment of the invention the GLP-2 compound is selected from GLP-2(1-33), 34R-GLP-2(1-34), A2G-GLP-2(1-33), A2G/34R-GLP-2(1-34), K30R-GLP-2(1-33); S5K-GLP -2(1-33); S7K-GLP-2(1-33); D8K-GLP-2(1-33); E9K-GLP-2(1-33); M10K-GLP-2(1-33); N11K-GLP -2(1-33); T12K-GLP-2(1-33); I13K-GLP-2(1-33); L14K-GLP-2(1-

33); D15K-GLP-2(1-33); N16K-GLP-2(1-33); L17K-GLP-2(1-33); A18K-GLP-2(1-33); D21K-GLP-2(1-33); N24K-GLP-2(1-33); Q28K-GLP-2(1-33); S5K/K30R-GLP-2(1-33); S7K/K30R-GLP-2(1-33); E9K/K30R-GLP-2(1-33); M10K/K30R-GLP-2(1-33); N11K/K30R-GLP-2(1-33); T12K/K30R-GLP-2(1-33); I13K/K30R-GLP-2(1-33); L14K/K30R-GLP-2(1-33); D15K/K30R-GLP-2(1-33); N16K/K30R-GLP-2(1-33); L17K/K30R-GLP-2(1-33); A18K/K30R-GLP-2(1-33); D21K/K30R-GLP-2(1-33); N24K/K30R-GLP-2(1-33); Q28K/K30R-GLP-2(1-33); K30R/D33K-GLP-2(1-33); D3E/K30R/D33E-GLP-2(1-33); D3E/S5K/K30R/D33E-GLP-2(1-33); D3E/S7K/K33R/D33E-GLP-2(1-33); D3E/D8K/K30R/D33E-GLP-2(1-33); D3E/E9K/K30R/D33E-GLP-2-(1-33); D3E/M10K/K30R/D33E-GLP-2(1-33); D3E/N11K/K30R/D33E-GLP-2(1-33); D3E/T12K/K30R/D33E-GLP-2(1-33); D3E/I13K/K30R/D33E-GLP-2(1-33); D3E/L14K/K30R/D33E-GLP-2(1-33); D3E/D15K/K30R/D33E-GLP-2(1-33); D3E/N16K/K30R/D33E-GLP-2(1-33); D3E/L17K/K30R/D33E-GLP-2(1-33); D3E/A18K/K30R/D33E-GLP-2(1-33); D3E/D21K/K30R/D33E-GLP-2(1-33); D3E/N24K/K30R/D33E-GLP-2(1-33); D3E/Q28K/K30R/D33E-GLP-2(1-33).

GLP-2 derivatives with only one lipophilic substituent attached to the GLP-2peptide are also applicable in the methods of the present invention, such as GLP-2 derivatives wherein the lipophilic substituent comprises from 4 to 40 carbon atoms, such as from 8 to 25 carbon atoms, e.g. from 12 to 20 carbon atoms.

The lipophilic substituent may be attached to an amino acid residue in such a way that a carboxyl group of the lipophilic substituent forms an amide bond with an amino group of the amino acid residue.

By way of example, the lipophilic substituent is attached to a Lys residue.

The lipophilic substituent may be attached to an amino acid residue in such a way that an amino group of the lipophilic substituent forms an amide bond with a carboxyl group of the amino acid residue.

The lipophilic substituent may also be attached to the GLP-2 peptide by means of a spacer, and said spacer may be selected from amongst β-alanine, gamma-aminobutyric acid (GABA), γ-glutamic acid, Lys, Asp, Glu, a dipeptide containing Asp, a dipeptide containing Glu, or a dipeptide containing Lys. In one embodiment of the invention the spacer is β-alanine.

A carboxyl group of the parent GLP-2 peptide may also form an amide bond with an amino group of a spacer, and the carboxyl group of the amino acid or dipeptide spacer forms an amide bond with an amino group of the lipophilic substituent.

An amino group of the parent GLP-2 peptide may also form an amide bond with a carboxylic group of a spacer, and an amino group of the spacer forms an amide bond with a carboxyl group of the lipophilic substituent.

In one embodiment of the invention the lipophilic substituent is a straight-chain or branched alkyl group. In one embodiment of the invention the lipophilic substituent is the acyl group of a straight-chain or branched fatty acid.

In one embodiment of the invention the lipophilic substituent is an acyl group of a straight-chain or branched alkane α,ω-dicarboxylic acid.

In one embodiment of the invention the GLP-2 derivative has one lipophilic substituent. In one embodiment of the invention the GLP-2 derivative has two lipophilic substituents. In one embodiment of the invention the GLP-2 derivative has three lipophilic substituents. In one embodiment of the invention the GLP-2 derivative has four lipophilic substituents. The following list contains GLP-2 derivatives which are particular applicable in the methods of the present invention.

S5K(3-(hexadecanoylamino)propionyl)-GLP-2(1-33);
S7K(3-(hexadecanoylamino)propionyl)-GLP-2(1-33);
D8K(3-(hexadecanoylamino)propionyl)-GLP-2(1-33);
E9K(3-(hexadecanoylamino)propionyl)-GLP-2(1-33);
M10K(3-(hexadecanoylamino)propionyl)-GLP-2(1-33);
N11K(3-(hexadecanoylamino)propionyl)-GLP-2(1-33);
T12K(3-(hexadecanoylamino)propionyl)-GLP-2(1-33);
I13K(3-(hexadecanoylamino)propionyl)-GLP-2(1-33);
L14K(3-(hexadecanoylamino)propionyl)-GLP-2(1-33);
D15K(3-(hexadecanoylamino)propionyl)-GLP-2(1-33);
N16K(3-(hexadecanoylamino)propionyl)-GLP-2(1-33);
L17K(3-(octanoylamino)propionyl)-GLP-2(1-33);
L17K(3-(nonanoylamino)propionyl)-GLP-2(1-33);
L17K(3-(decanoylamino)propionyl)-GLP-2(1-33);
L17K(3-(undecanoylamino)propionyl)-GLP-2(1-33);
L17K(3-(dodecanoylamino)propionyl)-GLP-2(1-33);
L17K(3-(tridecanoylamino)propionyl)-GLP-2(1-33);
L17K(3-(tetradecanoylamino)propionyl)-GLP-2(1-33);
L17K(3-(pentadecanoylamino)propionyl)-GLP-2(1-33);
L17K(3-(hexadecanoylamino)propionyl)-GLP-2(1-33);
L17K(3-(heptadecanoylamino)propionyl)-GLP-2(1-33);
L17K(3-(octadecanoylamino)propionyl)-GLP-2(1-33);
L17K(3-(nonadecanoylamino)propionyl)-GLP-2(1-33);
L17K(3-(eicosanoylamino)propionyl)-GLP-2(1-33);
L17K((S)-4-carboxy-4-(octanoylamino)butanoyl)-GLP-2(1-33);
L17K((S)-4-carboxy-4-(nonanoylamino)butanoyl)-GLP-2(1-33);
L17K((S)-4-carboxy-4-(decanoylamino)butanoyl)-GLP-2(1-33);
L17K((S)-4-carboxy-4-(undecanoylamino)butanoyl)-GLP-2(1-33);
L17K((S)-4-carboxy-4-(dodecanoylamino)butanoyl)-GLP-2(1-33);
L17K((S)-4-carboxy-4-(tridecanoylamino)butanoyl)-GLP-2(1-33);
L17K((S)-4-carboxy-4-(tetradecanoylamino)butanoyl)-GLP-2(1-33);
L17K((S)-4-carboxy-4-(pentadecanoylamino)butanoyl)-GLP-2(1-33);
L17K((S)-4-carboxy-4-(hexadecanoylamino)butanoyl)-GLP-2(1-33);
L17K((S)-4-carboxy-4-(heptadecanoylamino)butanoyl)-GLP-2(1-33);
L17K((S)-4-carboxy-4-(octadecanoylamino)butanoyl)-GLP-2(1-33);
L17K((S)-4-carboxy-4-(nonadecanoylamino)butanoyl)-GLP-2(1-33);
L17K((S)-4-carboxy-4-(eicosanoylamino)butanoyl)-GLP-2(1-33);
L17K(4-(octanoylamino)butanoyl)-GLP-2(1-33);
L17K(4-(nonanoylamino)butanoyl)-GLP-2(1-33);
L17K(4-(decanoylamino)butanoyl)-GLP-2(1-33);
L17K(4-(undecanoylamino)butanoyl)-GLP-2(1-33);
L17K(4-(dodecanoylamino)butanoyl)-GLP-2(1-33);
L17K(4-(tridecanoylamino)butanoyl)-GLP-2(1-33);
L17K(4-(tetradecanoylamino)butanoyl)-GLP-2(1-33);
L17K(4-(pentadecanoylamino)butanoyl)-GLP-2(1-33);
L17K(4-(hexadecanoylamino)butanoyl)-GLP-2(1-33);
L17K(4-(heptadecanoylamino)butanoyl)-GLP-2(1-33);
L17K(4-(octadecanoylamino)butanoyl)-GLP-2(1-33);
L17K(4-(nonadecanoylamino)butanoyl)-GLP-2(1-33);
L17K(4-(eicosanoylamino)butanoyl)-GLP-2(1-33);
A18K(3-(hexadecanoylamino)propionyl)-GLP-2(1-33);

D21K(3-(hexadecanoylamino)propionyl)-GLP-2(1-33);
N24K(3-(hexadecanoylamino)propionyl)-GLP-2(1-33);
Q28K(3-(hexadecanoylamino)propionyl)-GLP-2(1-33);
S5K(3-(hexadecanoylamino)propionyl)/K30R-GLP-2(1-33);
S7K(3-(hexadecanoylamino)propionyl)/K30R-GLP-2(1-33);
D8K(3-(hexadecanoylamino)propionyl)/K30R-GLP-2(1-33);
E9K(3-(hexadecanoylamino)propionyl)/K30R-GLP-2(1-33);
M10K(3-(hexadecanoylamino)propionyl)/K30R-GLP-2(1-33);
N11K(3-(hexadecanoylamino)propionyl)/K30R-GLP-2(1-33);
T12K(3-(hexadecanoylamino)propionyl)/K30R-GLP-2(1-33);
I13K(3-(hexadecanoylamino)propionyl)/K30R-GLP-2(1-33);
L14K(3-(hexadecanoylamino)propionyl)/K30R-GLP-2(1-33);
D15K(3-(hexadecanoylamino)propionyl)/K30R-GLP-2(1-33);
N16K(3-(hexadecanoylamino)propionyl)/K30R-GLP-2(1-33);
L17K(3-(octanoylamino)propionyl)/K30R-GLP-2(1-33);
L17K(3-(nonanoylamino)propionyl)/K30R-GLP-2(1-33);
L17K(3-(decanoylamino)propionyl)/K30R-GLP-2(1-33);
L17K(3-(undecanoylamino)propionyl)/K30R-GLP-2(1-33);
L17K(3-(dodecanoylamino)propionyl)/K30R-GLP-2(1-33);
L17K(3-(tridecanoylamino)propionyl)/K30R-GLP-2(1-33);
L17K(3-(tetradeanoylamino)propionyl)/K30R-GLP-2(1-33);
L17K(3-(pentadecanoylamino)propionyl)/K30R-GLP-2(1-33);
L17K(3-(hexadecanoylamino)propionyl)/K30R-GLP-2(1-33);
L17K(3-(heptadecanoylamino)propionyl)/K30R-GLP-2(1-33);
L17K(3-(octadecanoylamino)propionyl)/K30R-GLP-2(1-33);
L17K(3-(nonadecanoylamino)propionyl)/K30R-GLP-2(1-33);
L17K(3-(eicosanoylamino)propionyl)/K30R-GLP-2(1-33);
L17K((S)-4-carboxy-4-(octanoylamino)butanoyl)/K30R-GLP-2(1-33);
L17K((S)-4-carboxy-4-(nonanoylamino)butanoyl)/K30R-GLP-2(1-33);
L17K((S)-4-carboxy-4-(decanoylamino)butanoyl)/K30R-GLP-2(1-33);
L17K((S)-4-carboxy-4-(undecanoylamino)butanoyl)/K30R-GLP-2(1-33);
L17K((S)-4-carboxy-4-(dodecanoylamino)butanoyl)/K30R-GLP-2(1-33);
L17K((S)-4-carboxy-4-(tridecanoylamino)butanoyl)/K30R-GLP-2(1-33);
L17K((S)-4-carboxy-4-(tetradecanoylamino)butanoyl)/K30R-GLP-2(1-33);
L17K((S)-4-carboxy-4-(pentadecanoylamino)butanoyl)/K30R-GLP-2(1-33);
L17K((S)-4-carboxy-4-(hexadecanoylamino)butanoyl)/K30R-GLP-2(1-33);
L17K((S)-4-carboxy-4-(heptadecanoylamino)butanoyl)/K30R-GLP-2(1-33);
L17K((S)-4-carboxy-4-(octadecanoylamino)butanoyl)/K30R-GLP-2(1-33);
L17K((S)-4-carboxy-4-(nonadecanoylamino)butanoyl)/K30R-GLP-2(1-33);
L17K((S)-4-carboxy-4-(eicosanoylamino)butanoyl)/K30R-GLP-2(1-33);
L17K(4-(octanoylamino)butanoyl)/K30R-GLP-2(1-33);
L17K(4-(nonanoylamino)butanoyl)/K30R-GLP-2(1-33);
L17K(4-(decanoylamino)butanoyl)/K30R-GLP-2(1-33);
L17K(4-(undecanoylamino)butanoyl)/K30R-GLP-2(1-33);
L17K(4-(dodecanoylamino)butanoyl)/K30R-GLP-2(1-33);
L17K(4-(tridecanoylamino)butanoyl)/K30R-GLP-2(1-33);
L17K(4-(tetradecanoylamino)butanoyl)/K30R-GLP-2(1-33);
L17K(4-(pentadecanoylamino)butanoyl)/K30R-GLP-2(1-33);
L17K(4-(hexadecanoylamino)butanoyl)/K30R-GLP-2(1-33);
L17K(4-(heptadecanoylamino)butanoyl)/K30R-GLP-2(1-33);
L17K(4-(octadecanoylamino)butanoyl)/K30R-GLP-2(1-33);
L17K(4-(nonadecanoylamino)butanoyl)/K30R-GLP-2(1-33);
L17K(4-(eicosanoylamino)butanoyl)/K30R-GLP-2(1-33);
A18K(3-(hexadecanoylamino)propionyl)/K30R-GLP-2(1-33);
D21K(3-(hexadecanoylamino)propionyl)/K30R-GLP-2(1-33);
N24K(3-(hexadecanoylamino)propionyl)/K30R-GLP-2(1-33);
Q28K(3-(hexadecanoylamino)propionyl)/K30R-GLP-2(1-33);
D3E/S5K(3-(hexadecanoylamino)propionyl)/K30R/D33E-GLP-2(1-33);
D3E/S7K(3-(hexadecanoylamino)propionyl)/K30R/D33E-GLP-2(1-33);
D3E/D8K(3-(hexadecanoylamino)propionyl)/K30R/D33E-GLP-2(1-33);
D3E/E9K(3-(hexadecanoylamino)propionyl)/K30R/D33E-GLP-2(1-33);
D3E/M10K(3-(hexadeanoylamino)propionyl)/K30R/D33E-GLP-2(1-33);
D3E/N11K(3-(hexadecanoylamino)propionyl)/K30R/D33E-GLP-2(1-33);
D3E/T12K(3-(hexadecanoylamino)propionyl)/K30R/D33E-GLP-2(1-33);
D3E/I13K(3-(hexadecanoylamino)propionyl)/K30R/D33E-GLP-2(1-33);
D3E/L14K(3-(hexadecanoylamino)propionyl)/K30R/D33E-GLP-2(1-33);
D3E/D15K(3-(hexadecanoylamino)propionyl)/K30R/D33E-GLP-2(1-33);
D3E/N16K(3-(hexadecanoylamino)propionyl)/K30R/D33E-GLP-2(1-33);
D3E/L17K(3-(octanoylamino)propionyl)/k30R/D33E-GLP-2(1-33);
D3E/L17K(3-(nonanoylamino)propionyl)/K30R/D33E-GLP-2(1-33);
D3E/L17K(3-(decanoylamino)propionyl)/K30R/D33E-GLP-2(1-33);
D3E/L17K(3-(undecanoylamino)propionyl)/K30R/D33E-GLP-2(1-33);
D3E/L17K(3-(dodecanoylamino)propionyl)/K30R/D33E-GLP-2(1-33);
D3E/L17K(3-(tridecanoylamino)propionyl)/K30R/D33E-GLP-2(1-33);
D3E/L17K(3-(tetradecanoylamino)propionyl)/K30R/D33E-GLP-2(1-33);

D3E/L17K(3-(pentadecanoylamino)propionyl)/K30R/
D33E-GLP-2(1-33);
D3E/L17K(3-(hexadecanoylamino)propionyl)/K30R/
D33E-GLP-2(1-33);
D3E/L17K(3-(heptadecanoylamino)propionyl)/K30R/
D33E-GLP-2(1-33);
D3E/L17K(3-(octadecanoylamino)propionyl)/K30R/D33E-
GLP-2(1-33);
D3E/L17K(3-(nonadecanoylamino)propionyl)/K30R/
D33E-GLP-2(1-33);
D3E/L17K(3-(eicosanoylamino)propionyl)/K30R/D33E-
GLP-2(1-33);
D3E/L17K((S)-4-carboxy-4-(octanoylamino)butanoyl)/
K30R/D33E-GLP-2(1-33);
D3E/L17K((S)-4-carboxy-4-(nonanoylamino)butanoyl)/
K30R/D33E-GLP-2(1-33);
D3E/L17K((S)-4-carboxy-4-(decanoylamino)butanoyl)/
K30R/D33E-GLP-2(1-33);
D3E/L17K((S)-4-carboxy-4-(undecanoylamino)butanoyl)/
K30R/D33E-GLP-2(1-33);
D3E/L17K((S)-4-carboxy-4-(dodecanoylamino)butanoyl)/
K30R/D33E-GLP-2(1-33);
D3E/L17K((S)-4-carboxy-4-(tridecanoylamino)butanoyl)/
K30R/D33E-GLP-2(1-33);
D3E/L17K((S)-4-carboxy-4-(tetradecanoylamino)bu-
tanoyl)/K30R/D33E-GLP-2(1-33);
D3E/L17K((S)-4-carboxy-4-(pentadecanoylamino)bu-
tanoyl)/K30R/D33E-GLP-2(1-33);
D3E/L17K((S)-4-carboxy-4-(hexadecanoylamino)bu-
tanoyl)/K30R/D33E-GLP-2(1-33);
D3E/L17K((S)-4-carboxy-4-(heptadecanoylamino)bu-
tanoyl)/K30R/D33E-GLP-2(1-33);
D3E/L17K((S)-4-carboxy-4-(octadecanoylamino)bu-
tanoyl)/K30R/D33E-GLP-2(1-33);
D3E/L17K((S)-4-carboxy-4-(nonadecanoylamino)bu-
tanoyl)/K30R/D33E-GLP-2(1-33);
D3E/L17K((S)-4-carboxy-4-(eicosanoylamino)butanoyl)/
K30R/D33E-GLP-2(1-33);
D3E/L17K(4-(octanoylamino)butanoyl)/K30R/D33E-GLP-
2(1-33);
D3E/L17K(4-(nonanoylamino)butanoyl)/K30R/D33E-
GLP-2(1-33);
D3E/L17K(4-(decanoylamino)butanoyl)/K30R/D33E-
GLP-2(1-33);
D3E/L17K(4-(undecanoylamino)butanoyl)/K30R/D33E-
GLP-2(1-33);
D3E/L17K(4-(dodecanoylamino)butanoyl)/K30R/D33E-
GLP-2(1-33);
D3E/L17K(4-(tridecanoylamino)butanoyl)/K30R/D33E-
GLP-2(1-33);
D3E/L17K(4-(tetradecanoylamino)butanoyl)/K30R/D33E-
GLP-2(1-33);
D3E/L17K(4-(pentadecanoylamino)butanoyl)/K30R/D33E-
GLP-2(1-33);
D3E/L17K(4-(hexadecanoylamino)butanoyl)/K30R/D33E-
GLP-2(1-33);
D3E/L17K(4-(heptadecanoylamino)butanoyl)/K30R/D33E-
GLP-2(1-33);
D3E/L17K(4-(octadecanoylamino)butanoyl)/K30R/D33E-
GLP-2(1-33);
D3E/L17K(4-(nonadecanoylamino)butanoyl)/K30R/D33E-
GLP-2(1-33);
D3E/L17K(4-(eicosanoylamino)butanoyl)/K30R/D33E-
GLP-2(1-33);
D3E/A18K(3-(hexadecanoylamino)propionyl)/K30R/
D33E-GLP-2(1-33);
D3E/D21K(3-(hexadecanoylamino)propionyl)/K30R/
D33E-GLP-2(1-33);
D3E/N24K(3-(hexadecanoylamino)propionyl)/K30R/
D33E-GLP-2(1-33); and
D3E/Q28K(3-(hexadecanoylamino)propionyl)/K30R/
D33E-GLP-2(1-33).

Factor VII compounds applicable in the methods of the present invention encompasses wild-type Factor VII (i.e., a polypeptide having the amino acid sequence disclosed in U.S. Pat. No. 4,784,950), as well as variants of Factor VII exhibiting substantially the same or improved biological activity relative to wild-type Factor VII, Factor VII-related polypeptides as well as Factor VII derivatives and Factor VII conjugates. The term "Factor VII compounds" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. Such variants of Factor VII may exhibit different properties relative to human Factor VII, including stability, phospholipid binding, altered specific activity, and the like.

As used herein, "Factor VII-related polypeptides" encompasses polypeptides, including variants, in which the Factor VIIa biological activity has been substantially modified or reduced relative to the activity of wild-type Factor VIIa. These polypeptides include, without limitation, Factor VII or Factor VIIa into which specific amino acid sequence alterations have been introduced that modify or disrupt the bioactivity of the polypeptide.

The term "Factor VII derivative" as used herein, is intended to designate wild-type Factor VII, variants of Factor VII exhibiting substantially the same or improved biological activity relative to wild-type Factor VII and Factor VII-related polypeptides, in which one or more of the amino acids of the parent peptide have been chemically modified, e.g. by alkylation, PEGylation, acylation, ester formation or amide formation or the like. This includes but are not limited to PEGylated human Factor VIIa, cysteine-PEGylated human Factor VIIa and variants thereof.

The term "PEGylated human Factor VIIa" means human Factor VIIa, having a PEG mole-cule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively). For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce of Factor Xa in a system comprising TF embedded in a lipid membrane and Factor X. (Persson et al., J. Biol. Chem. 272:19919-19924, 1997); (ii) measuring Factor X hydrolysis in an aqueous system; (iii) measuring its physical binding to TF using an instrument based on surface plasmon resonance (Persson, FEBS Letts. 413:359-363, 1997) and (iv) measuring hydrolysis of a synthetic substrate.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of Factor VIIa that has been produced in the same cell type, when tested in one or more of a clotting assay, proteolysis assay, or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

The terms "variant" or "variants", as used herein, is intended to designate Factor VII having the sequence of wild-type factor VII, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "variant" or "variants" within this definition still have FVII activity in its activated form. In one embodiment a variant is 70% identical with the sequence of wild-type Factor VII. In one embodiment a variant is 80% identical with the sequence of wild-type factor VII. In another embodiment a variant is 90% identical with the sequence of wild-type factor VII. In a further embodiment a variant is 95% identical with the sequence of wild-type factor VII.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189; and FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota) and WO 00/66753 (University of Minnesota); and FVII variants as disclosed in WO 01/58935 (Maxygen ApS), WO 03/93465 (Maxygen ApS) and WO 04/029091 (Maxygen ApS) all of which are incorporated herein by reference.

Particular mentioning is made of FVII variants having increased biological activity compared to wild-type FVIIa include FVII variants as disclosed in WO 01/83725, WO 02/22776, WO 02/077218, PCT/DK02/00635, WO 2004/029090, WO 2003/037932; WO 02/38162 (Scripps Research Institute); and FVIIa variants with enhanced activity as disclosed in JP 2001061479 (Chemo-Sero-Therapeutic Res Inst.), all of which are incorporated herein by reference, all of which are incorporated herein by reference.

Examples of Factor VII variants having substantially reduced or modified biological activity relative to wild-type Factor VII include R152E-FVIIa (Wildgoose et al., Biochem 29:3413-3420, 1990), S344A-FVIIa (Kazama et al., J. Biol. Chem. 270:66-72, 1995), FFR-FVIIa (Hoist et al., Eur. J. Vasc. Endovasc. Surg. 15:515-520, 1998), and Factor VIIa lacking the Gla domain, (Nicolaisen et al., FEBS Letts. 317: 245-249, 1993), all of which are incorporated herein by reference.

Examples of variants of factor VII, factor VII or factor VII-related polypeptides include wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S3 14E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/

L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S3 14E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S3 14E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T-FVII, F374Y/V158D/E296V/M298Q/V158T-FVII, F374Y/L305V/V158D/E296V/M298Q/S314E-FVII, F374Y/L305V/E296V/M298Q/V158T/S314E-FVII, F374Y/L305V/E296V/M298Q/K337A/V158T-FVII, F374Y/L305V/E296V/K337A/V158T/S314E-FVII, F374Y/L305V/M298Q/K337A/V158T/S314E-FVII, F374Y/L305V/V158D/E296V/K337A/V158T-FVII, F374Y/L305V/V158D/M298Q/K337A/V158T-FVII, F374Y/L305V/V158D/K337A/V158T/S314E-FVII, F374Y/L305V/V158D/E296V/V158T/S314E-FVII, F374Y/L305V/V158D/E296V/M298Q/V158T-FVII, F374Y/L305V/V158D/M298Q/V158T/S314E-FVII, F374Y/L305V/V158D/M298Q/K337A/S314E-FVII, F374Y/V158D/E296V/M298Q/K337A/S314E-FVII, F374Y/L305V/V158D/E296V/K337A/S314E-FVII, F374Y/L305V/V158D/E296V/M298Q/K337A/S314E-FVII, S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn, FVII having substitutions, additions or deletions in the amino acid sequence from 304Arg to 329Cys.

Growth hormone applicable in the methods of the present invention includes human growth hormone (hGH), which sequence and characteristics are set froth in, e.g. *Hormone Drugs*, Gueriguian, U.S.P. Covention, Rockvill, 1982 and growth hormone compounds. The term "growth hormone compound" is intended to indicate human growth hormone (hGH) in which one or more amino acid residues have been deleted and/or replaced by other amino acid residues, natural or unnatural, and/or hGH comprising addition amino acid residues, natural or unnatural, and/or hGH in which at least one organic substituent is bound to one or more organic substituent. Particular mentioning is made of the 191 native amino acid sequence (somatropin) and the 192 amino acid N-terminal methionine species (somatrem).

Other examples of growth hormone compound applicable in the present invention include wherein amino acid No 172, 174, 176 and 178 as a group are replaced by one of the following groups of amino acids (R, S, F, R); (R, A, Y, R), (K, T, Y, K); (R, S, Y, R); (K, A, Y, R); (R, F, F, R); (K, Q, Y, R); (R, T, Y, H); (Q, R, Y, R); (K, K, Y, K); (R, S, F, S) or (K, S, N, R) as disclosed in WO 92/09690 (Genentech), which is incorporated herein by reference.

Other examples of growth hormone compound applicable in the present invention include hGH with the following substitutions G120R, G120K, G120Y, G120F and G120E, as disclosed in U.S. Pat. No. 6,004,931 (Genentech), which is incorporated herein by reference.

Other examples of growth hormone compound applicable in the present invention include hGH with the following set of substitutions R167N, D171S, E174S, F176Y and 1179T; R176E, D171S, E174S and F176Y; F10A, M14W, H18D and H21N; F10A, M14W, H18D, H21N, R167N, D171S, E174S, F176Y, 1179T; F10A, M14W, H18D, H21N, R167N, D171A, E174S, F176Y, I179T; F10H, M14G, $H_{18}N$ and H21N; F10A, M14W, H18D, H21N, R167N, D171A, T175T and 1179T; and F10I, M14Q, H18E, R167N, D171S and 1179T, as disclosed in U.S. Pat. No. 6,143,523 (Genentech), which is incorporated herein by reference.

Other examples of growth hormone compound applicable in the present invention include hGH with the following set of substitutions H18A, Q22A, F25A, D26A, Q29A, E65A, K168A, E174A and G120K as disclosed in U.S. Pat. No. 6,136,536 (Genentech), which is incorporated herein by reference.

Other examples of growth hormone compound applicable in the present invention include hGH with the following set of substitutions H18D, H21N, R167N, K168A, D171S, K172R, E174S, I179T and wherein G120 is further substituted with either R, K, W, Y, F or E, as disclosed in U.S. Pat. No. 6,057,292 (Genentech), which is incorporated herein by reference.

Other examples of growth hormone compound applicable in the present invention include hGH with the following set of substitutions H18D, H21N, R167N, K168A, D171S, K172R, E174S and I179T, as disclosed in U.S. Pat. No. 5,849,535 (Genentech), which is incorporated herein by reference.

Other examples of growth hormone compound applicable in the present invention include hGH with the following set of substitutions H18D, H21D, R167N, K168A, D171S, K172R, E174S and I179T; and H18A, Q22A, F25A, D26A, Q29A, E65A, K168A and E174A, as disclosed in WO 97/11178 (Genentech), which is incorporated herein by reference.

Other examples of growth hormone compound applicable in the present invention include hGH with the following set of substitutions K168A and E174A; R178N and I179M; K172A and F176A; and $H_{54}F$, S56E, L581, E62S, D63N and Q66E as disclosed in WO 90/04788 (Genentech), which is incorporated herein by reference.

Examples of cytokines which could be modified using the method of the present invention include erythropoietin (EPO), thrombopoietin, INF-α, IFN-β, IFN-γ, TNF-α, interleukin-1β (IL-1-β), IL-3, IL-4, IL-5, IL-10, IL-12, IL-15, IL-18, IL-19, IL-20, IL-21 IL-24, grannolyte colonystimulating factor (G-CSF), GM-CSF, and chemokines such as macrophage inflammatory protein-1 (MIP-1) gamma interferon inducible protein and monokines induced by IFNγ (MIG).

Particular examples of IL-19 applicable in the methods of the present invention include those disclosed WO 98/08870 (Human Genome Science), which is incorporated herein by reference. Particular mentioning is made of the peptide disclosed as SEQ ID NO:2 in WO 98/08870.

Particular examples of applicable IL-20 include those disclosed in WO 99/27103 (Zymo-genetics), which is incorporated herein by reference. In the present context, IL-20 is intended to indicate IL-20 itself and fragments thereof as well as polypeptides being at least 90% identical to IL-20 or fragments thereof. Proteins particular applicable in the methods of the present invention includes those disclosed in WO 99/27103 as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34 and SEQ ID NO:35.

Examples of IL-21 applicable in the methods of the present invention include those disclosed in WO 00/53761 (Zymogenetics), which is incorporated herein by reference. particular mentioning is made of the peptide disclosed as SEQ ID NO:2 in WO 00/53761.

TTF are applicable in the methods of the present invention. TTF peptides are a family of peptides found mainly in association with the gastrointestinal tract. Particular mentioning is made of breast cancer associated pS2 peptide (TFF-1), which is known from human, mouse, and rat, spasmolytical polypeptide (TFF-2), which is known from human, pig, rat, and mouse and intestinal trefoil factor (TFF-3), known from human, rat and mouse.

Other peptides from the TFF family applicable in the methods of the present invention include those disclosed in WO 02/46226 (Novo Nordisk), which is included herein by reference. Particular mentioning is made of a TFF-2 peptide wherein a TFF2 peptide with an amino acid as disclosed in SEQ ID NO:1 of WO 02/46226 comprising disulphide bonds between Cys6-Cys104, Cys8-Cys35, Cys19-Cys34, Cys29-Cys46, Cys58-Cys84, Cys68-Cys83, and Cys78-Cys95 and wherein a moiety X independently selected from sugar residues and oligosaccharides is covalently attached to Asn15.

Other peptides of the TFF family include TFF-1 and TFF-3 dimers as those disclosed in WO 96/06861 (Novo Nordisk), which is incorporated herein by reference.

Several melanorcortin receptors are known, and particular mentioning of peptides applicable for the methods of the present invention is made of peptidic melanocortin-4 receptor agonists, which are known to have an appetite suppressive effect. Particular mentioning is made of peptides or proteins disclosed in the following patent documents, which are all incorporated herein by reference: U.S. Pat. No. 6,054,556 (Hruby), WO 00/05263 (William Harvey Research), WO 00/35952 (Melacure), WO 00/35952 (Melacure), WO 00/58361 (Procter & Gamble), WO 01/52880 (Merck), WO 02/26774 (Procter & Gamble), WO 03/06620 (Palatin), WO 98/27113 (Rudolf Magnus Institute) and WO 99/21571 (Trega).

Other classes of peptides or proteins which are applicable in the methods of the present invention include enzymes. Many enzymes are used for various industrial purposes, and particular mentioning is made of hydrolases (proteases, lipases, cellulases, esterases), oxidoreductases (laccases, peroxidaxes, catalases, superoxide dismutases, lipoxygenases), transferases and isomerases.

Other peptides or proteins applicable in the methods of the present invention include ACTH, corticotropin-releasing factor, angiotensin, calcitonin, insulin and fragments and analogues thereof, glucagon, IGF-1, IGF-2, enterogastrin, gastrin, tetragastrin, pentagastrin, urogastrin, epidermal growth factor, secretin, nerve growth factor, thyrotropin releasing hormone, somatostatin, growth hormone releasing hormone, somatomedin, parathyroid hormone, thrombopoietin, erythropoietin, hypothalamic releasing factors, prolactin, thyroid stimulating hormones, endorphins, enkephalins, vasopressin, oxytocin, opiods and analogues thereof, asparaginase, arginase, arginine deaminase, adenosine deaminase and ribonuclease.

Peptides to be modified according to the methods of the present invention may either be isolated from natural sources (e.g. plants, animals or micro-organisms, such as yeast, bacteria, fungi or vira) or they may be synthesised. Peptides form natural sources also include peptides form transgenic sources, e.g. sources which have been genetically modified to express or to increase the expression of a peptide, wherein said peptide may be "natural" in the sense that it exists in nature or "unnatural" in the sense that it only exists due to human intervention. Peptides isolated form natural sources may also be subjected to synthetic modification prior to the conjugation of the present invention.

In one embodiment, the invention relates to conjugated peptides obtainable according to the methods of the present invention. If the conjugated peptide obtained by the methods of the present invention is a therapeutic peptide, the invention also provides the use of such compounds in therapy, and pharmaceutical compositions comprising such compounds.

In one embodiment, the invention provides conjugated peptides of the formula

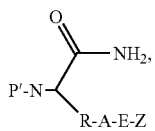

wherein P', R, A, E and Z are as defined above, and wherein the group

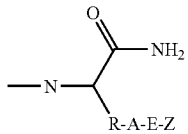

is bonded to the C-terminal of P' via a peptide bond.

Particular examples of such compounds include

Lys$^ε$(4-((2-(1-(mPEGcarbonyl)piperidin-4yl)ethoxy)imino)pentanoyl)192)hGH(1-192) amide, which mPEG has a molecular weight of 20 kDa;

(Lys$^ε$(4-((3-(palmitoylamino)propoxy)imino)pentanoyl) 192)hGH(1-192) amide;

(Lys$^ε$(4-((3-((2S)-2,6-mPEGcarbonylamino)hexanoylamino)propoxy)imino)pentanoyl)$_{34}$)GLP-2(1-34) amide, in which mPEG has a molecular weight of 20 kDa;

(Lys$^ε$(4-(1-(2-(3-(mPEG)propanoylamino)hydrazino)ethyl)benzoyl)192)hGH(1-92) amide, in which mPEG has a molecular weight of 10 kDa;

(S)-3-(4-((3-(3-Chlorophenyl)isoxazol-5-yl)methoxy)phenyl)-2-([Glu$^3$, Leu$^{10}$]GLP-2ylleucinylamino)propionic amide;

(S)-3-(4-((3-(3-Chlorophenyl)isoxazol-5-yl)methoxy)phenyl)-2-([Glu$^3$]GLP-2ylleucinylamino)propionic amide;

3-(3-(3-((4-((S)-2-Carbamoyl-3-([Glu$^3$, Leu$^{10}$]GLP-2ylleucinylamino)ethyl)phenoxyl)methyl)isoxazol-3-yl)benzylcarbamoyl)propionic acid;

11-(4-(4-((2S)-2-Carbamoyl-2-(([Glu$^3$, Leu$^{10}$]GLP-2ylleucinylamino)ethyl) pheoxymethyl)-1,2,3-triazolyl) undecanoic acid;

11-(5-(4-((2S)-2-Carbamoyl-2-(([Glu$^3$, Leu$^{10}$]GLP-2ylleucinylamino)ethyl) pheoxymethyl)-1,2,3-triazolyl) undecanoic acid11-(4-(4-((S)-2-carbamoyl-2-([Glu$^3$] GLP-2ylleucinylamino))phenoxymethyl)-1H-1,2,3-triazol-1-yl)undecanoic acid;

11-(5-(4-((S)-2-carbamoyl-2-([Glu$^3$]GLP-2ylleucinylamino))phenoxymethyl)-1H-1,2,3-triazol-1-yl)undecanoic acid;

2-([Glu$^3$]GLP-2ylleucinyl)-3-(4-((1-((N-(mPeg20kDayl)carbamoyl)decanyl)-1H-1,2,3-tetrazol-4-yl)methoxy)phenyl)propionamide; and 2-([Glu$^3$]GLP-2ylleucinyl)-3-(4-((1-((N-(mPeg20kDayl)carbamoyl)decanyl)-1H-1,2,3-tetrazol-5-yl)methoxy)phenyl)propionamide.

Insulin is used to treat or prevent diabetes, and in one embodiment, the present invention thus provides a method of treating type 1 or type 2 diabetes, the method comprising administering to a subject in need thereof a therapeutically effective amount of an insulin or insulin compound conjugate according to the present invention.

In another embodiment, the invention provides the use of an insulin or insulin compound conjugate according to the present invention in the manufacture of a medicament used in the treatment of type 1 or type 2 diabetes.

GLP-1 may be used in the treatment of hyperglycemia, type 2 diabetes, impaired glucose tolerance, type 1 diabetes, obesity, hypertension, syndrome X, dyslipidemia, β-cell apoptosis, β-cell deficiency, inflammatory bowel syndrome, dyspepsia, cognitive disorders, e.g. cognitive enhancing, neuroprotection, atherosclerosis, coronary heart disease and other cardiovascular disorders. In one embodiment, the present invention thus provides a method of treating said diseases, the method comprising administering to a subject in need thereof a therapeutically effective amount of a GLP-1 or GLP-1 compound conjugate according to the present invention.

In another embodiment, the invention provides the use of a GLP-1 or GLP-1 compound conjugate according to the present invention in the manufacture of a medicament used in the treatment of the above mentioned diseases.

GLP-2 may be used in the treatment of intestinal failure leading to malabsorption of nutrients in the intestines, and in particular GLP-2 may be used in the treatment of small bowel syndrome, Inflammatory bowel syndrome, Crohns disease, colitis including collagen colitis, radiation colitis, post radiation atrophy, non-tropical (gluten intolerance) and tropical sprue, damaged tissue after vascular obstruction or trauma, tourist diarrhea, dehydration, bacteremia, sepsis, anorexia nervosa, damaged tissue after chemotherapy, premature infants, schleroderma, gastritis including atrophic gastritis, postantrectomy atrophic gastritis and *helicobacter pylori* gastritis, ulcers, enteritis, cul-de-sac, lymphatic obstruction, vascular disease and graft-versus-host, healing after surgical procedures, post radiation atrophy and chemotherapy, and osteoporosis. It is therefore an intension of the present invention to provide methods of treating the above diseases, the method comprising administering to a subject in need thereof a therapeutically effective amount of a GLP-2 or GLP-2 compound conjugate according to this invention.

In another embodiment, the present invention provides the use of a GLP-2 or GLP-2 compound conjugate according to this invention in the manufacture of a medicament used in the treatment of the above mentioned diseases.

Growth hormone has been implicated in the treatment of diseases benefiting from an increase in the plasma level of growth hormone. In one embodiment, the invention provides a method for the treatment of growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or $1^{st}$ toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; or short stature due to glucucorticoid treatment in children, the method comprising administering to a patient in need thereof an effective amount of a growth hormone compound conjugate according to the present invention.

In one aspect, the invention provides a method for the acceleration of the healing of muscle tissue, nervous tissue or wounds; the acceleration or improvement of blood flow to damaged tissue; or the decrease of infection rate in damaged tissue, the method comprising administration to a patient in need thereof an effective amount of a growth hormone compound onjugayte according to the present invention.

In one aspect, the invention provides the use of growth hormone compound conjugates according to the present invention in the manufacture of medicaments for the treatment of the above mentioned diseases.

Cytokines are implicated in the etiology of a host of diseases involving the immune system. In particular it is mentioned that IL-20 could be involved in psoriasis and its treatment, and 1-21 is believed to be involved in cancer and could constitute a treatment to this disease. In one embodiment, the invention provides a method for the treatment of psoriasis comprising the administration of IL-20 conjugates according to the present invention. In another embodiment, the invention relates to the use of an IL-20 conjugate of the present invention in the manufacture of a medicament used in the treatment of psoriasis.

In another embodiment, the present invention relates to a method of treating cancer, the method comprising administration of an IL-21 conjugate of the present invention to qa subject in need thereof.

In another embodiment, the invention relates to the use of an IL-21 conjugate according to the present invention in the manufacture of a medicament used in the treatment of cancer.

TF peptides may be used to increase the viscosity of muscus layers in subject, to reduce secretion of salvia, e.g. where the increase salvia secretion is caused by irradiation therapy, treatment with anticholinergics or Sjögren's syndrome, to treat allergic rhinitis, stress induced gastric ulcers secondary to trauma, shock, large operations, renal or liver diseases, treatment with NSAID, e.g. aspirin, steroids or alcohol. TTF peptides may also be used to treat Chrohn's disease, ulcerative colitis, keratoconjunctivitis, chronic bladder infections, intestinal cystitis, papillomas and bladder cancer. In one embodiment, the invention thus relates the a method of treating the above mention diseases or states, the method comprising administering to a subject patient in need thereof a therapeutically effective amount of a TTF conjugate according to the present invention.

In another embodiment, the invention relates the use of a TTF conjugate of the present invention in the manufacture of a medicament for the treatment of the above mentioned diseases or states.

Melanocortin receptor modifiers, and in particular melanorcortin 4 receptor agonists have been implicated the treatment and prevention of obesity and related diseases. In one embodiment, the present invention provides a method for preventing or delaying the progression of impaired glucose tolerance (IGT) to non-insulin requiring type 2 diabetes, for preventing or delaying the progression of non-insulin requiring type 2 diabetes to insulin requiring diabetes, for treating obesity and for regulating the appetite. Melanocortin 4 receptor agonists have also been implicated in the treatment of diseases selected from atherosclerosis, hypertension, diabetes, type 2 diabetes, impaired glucose tolerance (IGT), dyslipidemia, coronary heart disease, gall-bladder disease, gall stone, osteoarthritis, cancer, sexual dysfunction and the risk of premature death. In one embodiment, the invention thus provides a method of treating the above diseases or states, the method comprising administering to a subject in need thereof a therapeutically effective amount of an melanocortin 4 receptor agonist conjugate of the present invention.

In still another embodiment, the invention relates to the use of a melanocortin 4 receptor agonist conjugate of the present invention in the manufacture of a medicament for the treatment of the above mentioned diseases or states.

Factor VII compounds have been implicated in the treatment of disease related to coagulation, and biological active Factor VII compounds in particular have been implicated in the treatment of hemophiliacs, hemophiliacs with inhibitors to Factor VIII and IX, patients with thrombocytopenia, patients with thrombocytopathies, such as Glanzmann's thrombastenia platelet release defect and storage pool defects, patient with von Willebrand's disease, patients with liver disease and bleeding problems associated with traumas or surgery. Biologically inactive Factor VII compounds have been implicated in the treatment of patients being in hypercoagluable states, such as patients with sepsis, deep-vein thrombosis, patients in risk of myocardial infections or thrombotic stroke, pulmonary embolism, patients with acute coronary syndromes, patients undergoing coronary cardiac, prevention of cardiac events and restenosis for patient receiving angioplasty, patient with peripheral vascular diseases, and acute respiratory distress syndrome. In one embodiment, the invention thus provides a method for the treatment of the above mentioned diseases or states, the method comprising administering to a subject in need, thereof a therapeutically effective amount of a Factor VII compound conjugate according to the present invention.

In another embodiment, the invention provides the use of a Factor VII compound conjugate according to the present invention in the manufacture of a medicament used in the treatment of the above mentioned diseases or states.

Many diseases are treated using more than one medicament in the treatment, either concomitantly administered or sequentially administered. It is therefore within the scope of the present invention to use the peptide conjugates of the present invention in therapeutic methods for the treatment of one of the above mentioned diseases in combination with one or more other therapeutically active compound normally used to in the treatment said disease. By analogy, it is also within the scope of the present invention to use the peptide conjugates of the present invention in combination with other therapeutically active compounds normally used in the treatment of one of the above mentioned diseases in the manufacture of a medicament for said disease.

In another embodiment, the present invention provides the use of conjugated peptides of the present invention in diagnostics.

α-amino acid amides are, as mentioned previously, particular well-suited as a nucleophile in the methods of the present invention. In one embodiment, the invention thus provides compounds according to formula (I)

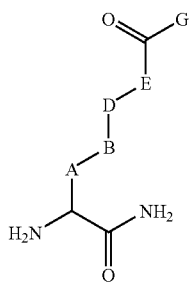

[I]

wherein A and E independently represent $C_{1-6}$alkylene, $C_{2-6}$alkenylene, $C_{2-6}$alkynylene or arylene, all of which may optionally be substituted with one or more substituents selected from halogen, amino, cyano and nitro;

B and D represents —C(O) or —NH— with the proviso that when B represents —C(O)— then D must represent —NH—, and when B represents —NH— then D must represent —C(O); and G represents hydrogen or $C_{1-6}$-alkyl, $C_{2-6}$alkenyl, $C_{2-6}$alkynyl or aryl, all of which may optionally be substituted with one or more substituents selected from halogen, amino, cyano and nitro.

In one embodiment, A and E independently represent $C_{1-6}$alkylene, such as methylene, ethylene, propylene, butylenes, pentylene or hexylene, or arylene, such as phenylene.

In one embodiment, G represents hydrogen or methyl, ethyl, propyl or butyl.

Particular examples of a compound of formula I include
(2S)-2-Amino-6-(4-oxo-4-phenylbutyrylamino)hexanoic acid amide,
4-Acetyl-N-((5S)-5-amino-5-carbamoylpentyl)benzamide,
(2S)-2-Amino-6-(4-oxo-4(4-chlorophenylbutyrylamino) hexanoic acid amide,
3-Acetyl-N-((5S)-5-amino-5-carbamoylpentyl)benzamide, and
2-Acetyl-N-((5S)-5-amino-5-carbamoylpentyl)benzamide In another embodiment, the invention provides compounds according to formula II

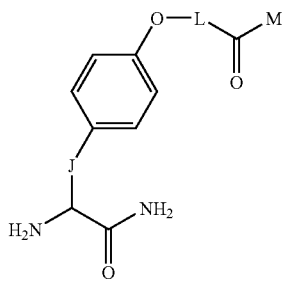

[II]

wherein J and L independently represent $C_{1-6}$-alkylene, $C_{2-6}$alkenylene, $C_{2-6}$alkynylene or arylene, all of which may optionally be substituted with one or more substituents selected from halogen, amino, cyano and nitro;

and M represents hydrogen or $C_{1-6}$-alkyl.

In one embodiment, J and L independently represent $C_{1-6}$-alkylene, such as methylene, ethylene, propylene, butylenes, pentylene or hexylene, or arylene, such as phenylene.

In one embodiment, M represents hydrogen or methyl, ethyl, propyl or butyl.

In one embodiment, the compounds of formula II are selected from amongst
(2S)-Amino-3-[4-(2-oxopropoxy)phenyl]propionamide,
(2S)-Amino-3-[4-(2-oxobutoxy)phenyl]propionamide,
(2S)-Amino-3-[4-(2-oxopentoxy)phenyl]propionamide, and
(2S)-Amino-3-[4-(4-oxopentoxy)phenyl]propionamide.

In still another embodiment, the invention provides compounds according to formula III

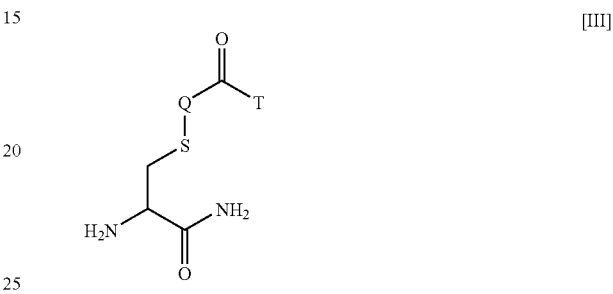

[III]

wherein Q represents represent $C_{1-6}$alkylene, $C_{2-6}$alkenylene, $C_{2-6}$alkynylene or arylene, all of which may optionally be substituted with one or more substituents selected from halogen, amino, cyano and nitro;

and T represents hydrogen or $C_{1-6}$-alkyl.

In one embodiment, Q represents $C_{1-6}$alkylene, such as methylene, ethylene, propylene, butylenes, pentylene or hexylene, or arylene, such as phenylene.

In one embodiment, T represents hydrogen or methyl, ethyl, propyl or butyl.

In still another embodiment, the invention provides compounds according to formula IV

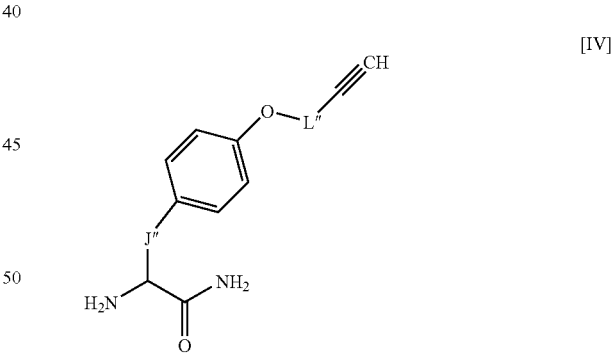

[IV]

wherein J″ and L″ independently represent $C_{1-6}$alkylene or arylene, all of which may optionally be substituted with one or more substituents selected from halogen amino, cyano and nitro.

In one embodiment J and L independently represent methylene or ethylene.

In one embodiment, the compounds of formula IV are selected from amongst (S)-2-amino-3-(4-(propargyloxy) phenyl)propionyl amide.

Pharmaceutical Compositions

Another object of the present invention is to provide a pharmaceutical composition comprising a compound of formula [a] which is present in a concentration from $10^{-12}$ mg/ml to 200 mg/ml, such as e.g. $10^{-10}$ mg/ml to 5 mg/ml and wherein said composition has a pH from 2.0 to 10.0. The composition may further comprise a buffer system, preservative(s), tonicity agent(s), chelating agent(s), stabilizers and surfactants. In one embodiment of the invention the pharmaceutical composition is an aqueous composition, i.e. composition comprising water. Such composition is typically a solution or a suspension. In a further embodiment of the invention the pharmaceutical composition is an aqueous solution. The term "aqueous composition" is defined as a composition comprising at least 50% w/w water. Likewise, the term "aqueous solution" is defined as a solution comprising at least 50' % w/w water, and the term "aqueous suspension" is defined as a suspension comprising at least 50% w/w water.

In another embodiment the pharmaceutical composition is a freeze-dried composition, whereto the physician or the patient adds solvents and/or diluents prior to use.

In another embodiment the pharmaceutical composition is a dried composition (e.g. freeze-dried or spray-dried) ready for use without any prior dissolution.

In a further aspect the invention relates to a pharmaceutical composition comprising an aqueous solution of a compound of formula [a], and a buffer, wherein said compound of formula [a] is present in a concentration from 0.1-100 mg/ml or above, and wherein said composition has a pH from about 2.0 to about 10.0.

In another embodiment of the invention the pH of the composition is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the composition further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 20$^{th}$ edition, 2000.

In a further embodiment of the invention the composition further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects obtained using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 20$^{th}$ edition, 2000.

In a further embodiment of the invention the composition further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 20$^{th}$ edition, 2000.

In a further embodiment of the invention the composition further comprises a stabilizer. The use of a stabilizer in pharmaceutical compositions is well-known to the skilled person. For convenience reference is made to Remington: *The Science and Practice of Pharmacy*, 20$^{th}$ edition, 2000.

More particularly, compositions of the invention are stabilized liquid pharmaceutical compositions whose therapeutically active components include a protein that possibly exhibits aggregate formation during storage in liquid pharmaceutical compositions. By "aggregate formation" is intended a physical interaction between the protein molecules that results in formation of oligomers, which may remain soluble, or large visible aggregates that precipitate from the solution. By "during storage" is intended a liquid pharmaceutical composition or composition once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or composition is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a protein during storage of a liquid pharmaceutical composition can adversely affect biological activity of that protein, resulting in loss of therapeutic efficacy of the pharmaceutical composition. Furthermore, aggregate formation may cause other problems such as blockage of tubing, membranes, or pumps when the protein-containing pharmaceutical composition is administered using an infusion system.

The pharmaceutical compositions of the invention may further comprise an amount of an amino acid base sufficient to decrease aggregate formation by the protein during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L or D isomer, or mixtures thereof) of a particular amino acid (methionine, histidine, arginine, lysine, isoleucine, aspartic acid, tryptophan, threonine and mixtures thereof) or combinations of these stereoisomers or glycine or an organic base such as but not limited to imidazole, may be present in the pharmaceutical compositions of the invention so long as the particular amino acid or organic base is present either in its free base form or its salt form. In one embodiment the L-stereoisomer of an amino acid is used. In one embodiment the D-stereoisomer is used. Compositions of the invention may also be formulated with analogues of these amino acids. By "amino acid analogue" is intended a derivative of the naturally occurring amino acid that brings about the desired effect of decreasing aggregate formation by the protein during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the protein acting as the therapeutic agent is a protein comprising at least one methionine residue susceptible to such oxidation. By "inhibit" is intended minimal accumulation of methionine oxidized species over time. Inhibiting methionine oxidation results in greater retention of the protein in its proper molecular form. Any stereoisomer of methionine (L or D isomer) or any combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be obtained by adding methionine such that the ratio of methionine added to methionine residues ranges from about 1:1 to about 1000:1, such as 10:1 to about 100:1.

In a further embodiment of the invention the composition further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active protein therein. Stabilizing agents of particular interest to the present invention include, but are not limited to, methionine and EDTA, which protect the protein against methionine oxidation, and a nonionic surfactant, which protects the protein against aggregation associated with freeze-thawing or mechanical shearing.

In a further embodiment of the invention the composition further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl(alkyl ester), alkoxy(alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof $C_6$-$C_{12}$ (eg. oleic acid and caprylic acid), acylcarnitines and derivatives, $N^\alpha$-acylated derivatives of lysine, arginine or histidine, or side-chain acylated derivatives of lysine or arginine, N-acylated derivatives of dipeptides comprising any combination of lysine, arginine or histidine and a neutral or acidic amino acid, N-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 20$^{th}$ edition, 2000.

It is possible that other ingredients may be present in the pharmaceutical composition of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical composition of the present invention.

Pharmaceutical compositions containing a compound of formula [a] according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the present invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the compound of formula [a], increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the present invention are useful in the composition of solids, semisolids, powder and solutions for pulmonary administration of compound of formula [a], using, for example a metered dose inhaler, dry powder inhaler and a nebulizer, all being devices well known to those skilled in the art.

Compositions of the current invention are specifically useful in the composition of controlled, sustained, protracting, retarded, and slow release drug delivery systems. More specifically, but not limited to, compositions are useful in composition of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Composition and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the Compound of formula [a] in the form of a nasal or pulmonal spray. As a still further option, the pharmaceutical compositions containing the compound of formula [a] of the invention can also be adapted to transdermal administration, e.g. by needle-free injection or from a patch, optionally an iontophoretic patch, or transmucosal, e.g. buccal, administration.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Following abbreviations are used for chemical groups:

Fmoc:

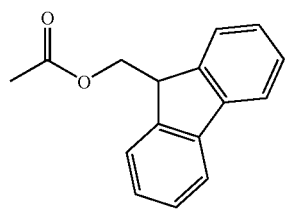

Boc:

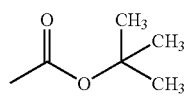

Pmc:

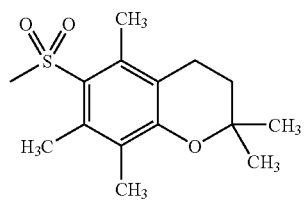

Trt:

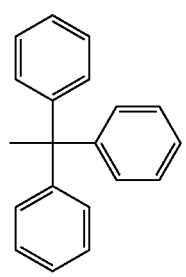

-continued tBu:

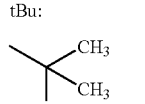

OtBu:

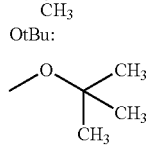

Following other abbreviations were used:
DMSO: Dimethylsulfoxide
CHCA: 4-Hydroxy-alpha-cyanocinnamic acid

HEPES

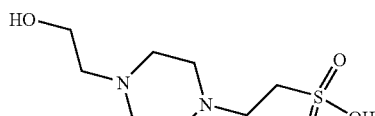

EDTA:

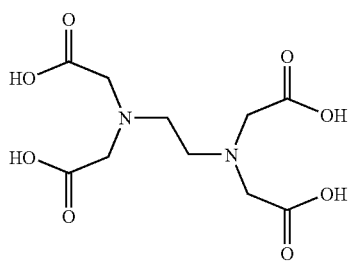

CPY: Carboxypeptidase Y.

HPLC-Methods:

Method 02-B4-4:

The RP-analyses was performed using an Alliance Waters 2695 system fitted with a Waters 2487 dualband detector. UV detections at 214 nm and 254 nm were collected using a Symmetry300 C18, 5 um, 3.9 mm×150 mm column, 42° C. The compounds are eluted with a linear gradient of 5-95% acetonitrile in water which is buffered with 0.05% trifluoroacetic acid over 15 minutes at a flow-rate of 1.0 min/min.

Method 03-B1-1:

The RP-analysis was performed using a Waters 2690 systems fitted with a Waters 996 diode array detector. UV detections were collected at 214, 254, 276, and 301 nm on a 218TP54 4.6 mm×250 mm 5μ C-18 silica column (The Seperations Group, Hesperia), which was eluted at 1 ml/min at 42° C. The column was equilibrated with 5% acetonitrile, which was buffered with 0.1% trifluoroacetic acid, in a 0.1% aqueous solution of trifluoroacetic acid in water. After injection, the sample was eluted by a gradient of 0% to 90% acetonitrile, which was buffered with 0.1% trifluoroacetic acid, in a 0.1% aqueous solution of trifluoroacetic acid in water during 50 min.

Mass spectra for peptides were obtained on an Agilent 1100 Series in the range of 500-1800 Da or on Perkin Elmer PE API 100 in the range of 500-2000 Da. Typically the found signals for m/z correspond to a series of any of z=1, 2, 3, 4, 5, or 6.

MALDI-TOF spectra were obtained on a Bruker Daltonix autoflex.

The transacylating compound, e.g. the compound of the formula

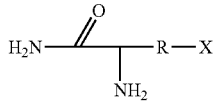

and the conjugating moiety, Y-E-Z, may either be acquired commercially or synthesized according to the following guidelines in general methods below.

General Method (A):

A compound of the general formula

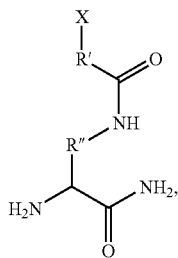

wherein R' and R" independently represents $C_{1-15}$alkylene, $C_{2-15}$alkenylene, $C_{2-15}$alkynylene, $C_{1-15}$heteroalkylene, $C_{2-15}$heteroalkenylene, $C_{2-15}$heteroalkynylene, wherein one or more homocyclic aromatic compound biradical or heterocyclic compound biradical may be inserted, may be prepared from a suitable amino acid methyl ester which is protected at the alpha-amino group by a suitable protecting group PG as described in the literature (e.g. T. W. Greene, P. G. M. Wuts, Protective groups in organic synthesis, $2^{nd}$ ed., 1991 John Wiley & Sons, Inc. New York)

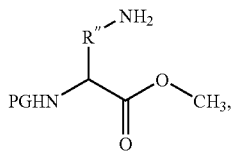

by an acylation method, e.g. using an suitable acid, in which X may or may not be protected by a suitable protective group, as described in the literature (e.g. T. W. Greene, P. G. M. Wuts, Protective groups in organic synthesis, $2^{nd}$ ed., 1991 John Wiley & Sons, Inc. New York)

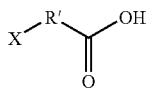

and a coupling reagent such as e.g. 1-hydroxybenzotriazole, 3,4-dihydro-3-hydroxybenzotriazin-4-one or 7-azabenzotriazole in combination with e.g. a carbodiimide such as e.g. diisopropylcarbodiimide or 1-(3-dimethylaminopropyl)-3-ethylcarbodiimide hydrochloride in the presence or absence of a suitable base such as e.g. triethylamine or ethyldiisopropylamine to form the ester of type

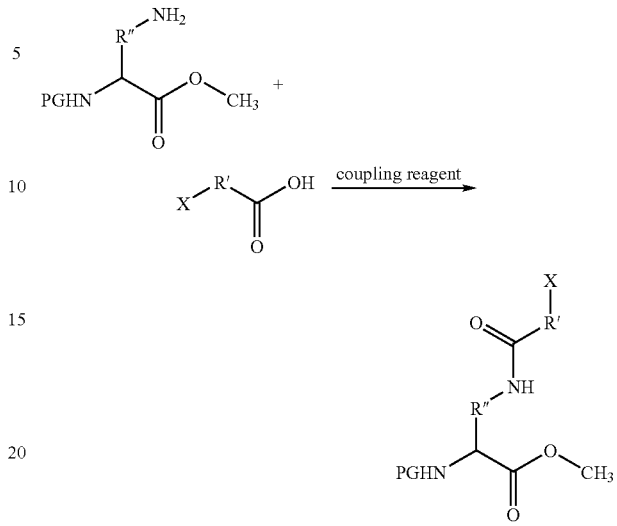

The ester may be transformed into the corresponding amide by reaction with e.g. ammonia in a suitable solvent or mixture of solvents such as e.g. water or N,N-dimethylformamide.

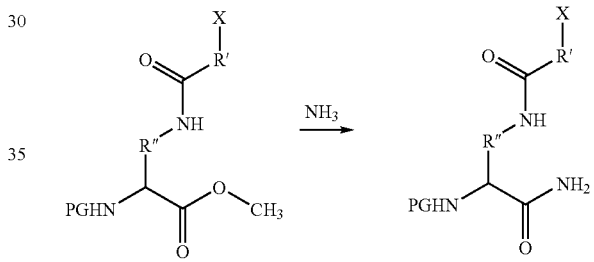

The removal of all protective groups may be performed in one or several steps by methods as described in the literature (e.g. T. W. Greene, P. G. M. Wuts, Protective groups in organic synthesis, $2^{nd}$ ed., 1991 John Wiley & Sons, Inc. New York)

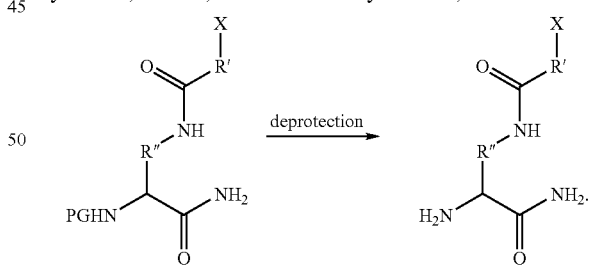

As defined in General Method (A)

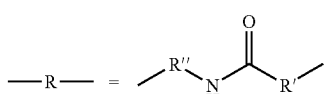

Amino acid methyl esters are generally commercially available, or they may be synthesized by well-known methods.

General Method (B):

A compound of the general formula

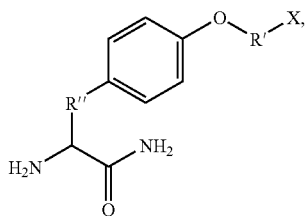

wherein R' and R" are defined as above, may be prepared from a suitable amino acid methyl ester which is protected at the alpha-amino group by a suitable protecting group PG, as described in the literature (e.g. T. W. Greene, P. G. M. Wuts, Protective groups in organic synthesis, $2^{nd}$ ed., 1991 John Wiley & Sons, Inc. New York)

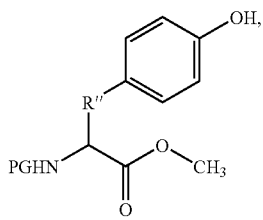

by an alkylation of the aromatic hydroxyl group using an suitable alcohol, in which X may or may not be protected by a suitable protective group, as described in the literature (e.g. T. W. Greene, P. G. M. Wuts, Protective groups in organic synthesis, $2^{nd}$ ed., 1991 John Wiley & Sons, Inc. New York)

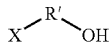

under conditions which effect alkylation, as described in the literature, e.g. Mitsunobu conditions such as e.g. triphenylphosphine and ethyl azodicarboxylate to form the ester of type

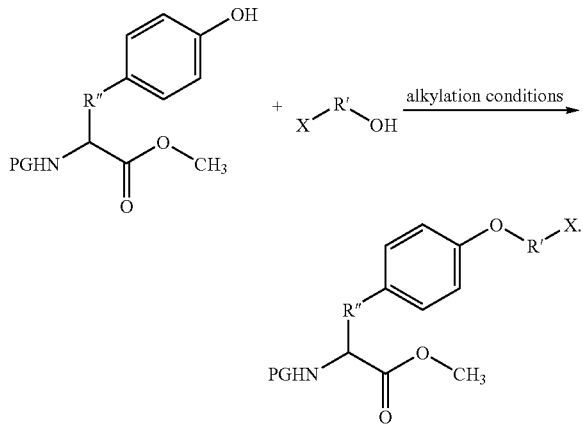

The ester may be transformed into the corresponding amide by reaction with e.g. ammonia in a suitable solvent or mixture of solvents such as e.g. water or N,N-dimethylformamide.

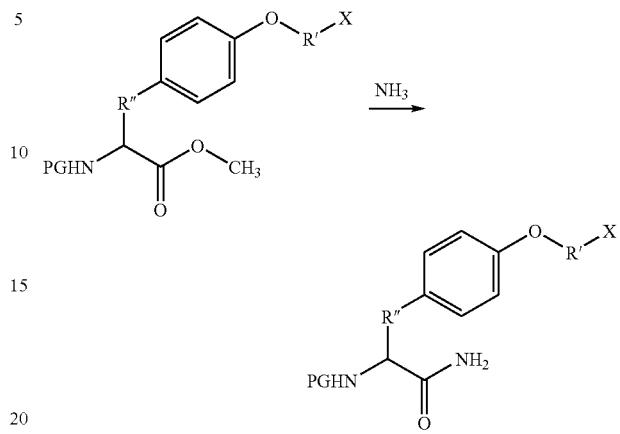

The removal of all protective groups may be performed in one or several steps by methods as described in the literature (e.g. T. W. Greene, P. G. M. Wuts, Protective groups in organic synthesis, $2^{nd}$ ed., 1991 John Wiley & Sons, Inc. New York)

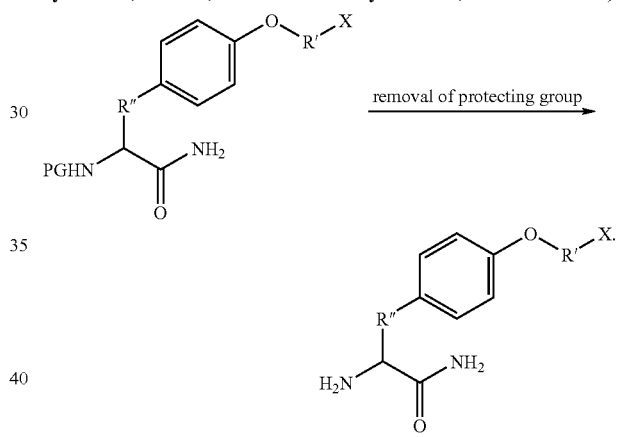

As defined in General Method (B)

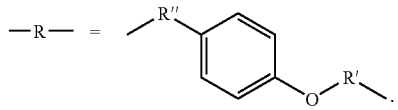

General Method (C):

A compound of the general formula

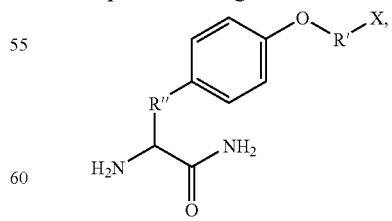

wherein R' and R" are defined as above, may be prepared from a suitable amino acid methyl ester which is protected at the alpha-amino group by a suitable protecting group PG, as and described in the literature, e.g. in T. W. Greene, P. G. M. Wuts, Protective groups in organic synthesis, $2^{nd}$ ed., 1991 John Wiley & Sons, Inc. New York)

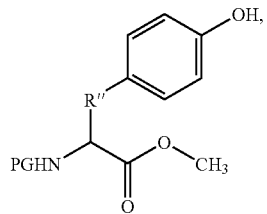

by an alkylation of the aromatic hydroxyl group, using an suitable alkylation reagent

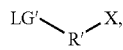

in which the anion of LG' is a suitable leaving group such as halogenide or sulfonate and X may or may not be protected by a suitable protective group as described in the literature, e.g. in T. W. Greene, P. G. M. Wuts, Protective groups in organic synthesis, $2^{nd}$ ed., 1991 John Wiley & Sons, Inc. New York. The reaction may take place under basic conditions, applying bases such as e.g. potassium carbonate, diazabicylo[5,4,0] undec-5-ene, or tert-butyltetramethyluanidine at a suitable temperature, typically between −78° C. and 200° C.

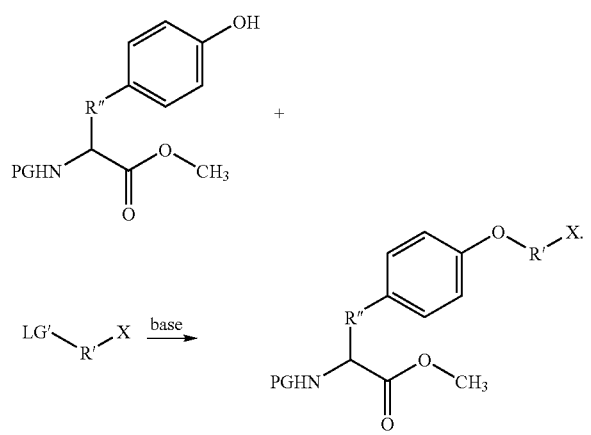

The ester may be transformed into the corresponding amide by reaction with e.g. ammonia in a suitable solvent or mixture of solvents such as e.g. water or N,N-dimethylformamide.

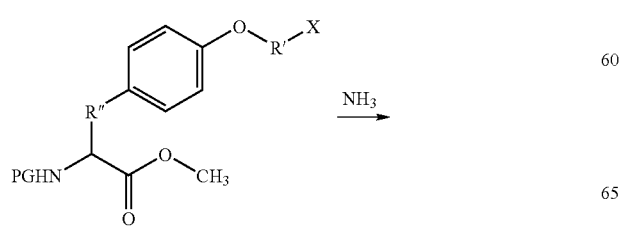

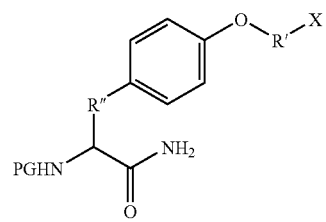

The removal of all protective groups may be performed in one or several steps by methods as described in the literature, e.g. in T. W. Greene, P. G. M. Wuts, Protective groups in organic synthesis, $2^{nd}$ ed., 1991 John Wiley & Sons, Inc. New York

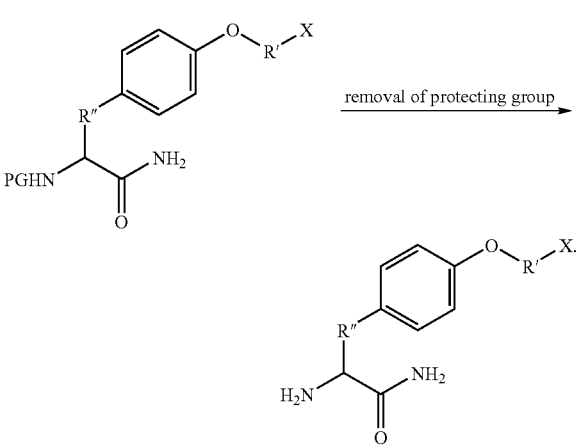

As defined in General Method (C)

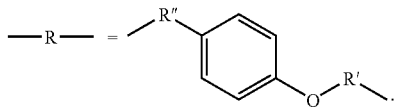

General Method (D):

A compound of the general formula

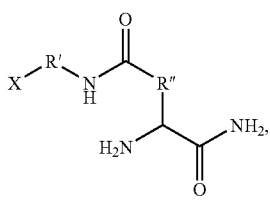

wherein R' and R" are defined as above, may be prepared from a suitable acid which is protected at the alpha-amino group by a suitable protecting group PG, as described in the literature, e.g. in T. W. Greene, P. G. M. Wuts, Protective groups in organic synthesis, $2^{nd}$ ed., 1991 John Wiley & Sons, Inc. New York

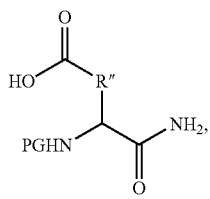

by reaction with a suitable primary or secondary amine, in which X may or may not be protected by a suitable protecting group, using acylation conditions known to a person skilled in the art e.g. a coupling reagent such as e.g. 1-hydroxybenzotriazole, 3,4-dihydro-3-hydroxybenzotriazin-4-one or 7-azabenzotriazole in combination with e.g. a carbodiimide such as e.g. diisopropylcarbodiimide or 1-(3-dimethylaminopropyl)-3-ethylcarbodiimide hydrochloride in the presence or absence of a suitable base such as e.g. triethylamine or ethyldiisopropylamine to form an amide

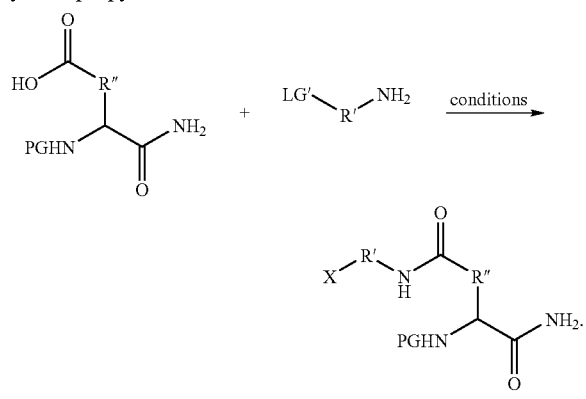

The removal of all protective groups may be performed in one or several steps as described in the literature, T. W. Greene, P. G. M. Wuts, Protective groups in organic synthesis, 2$^{nd}$ ed., 1991 John Wiley & Sons, Inc. New York

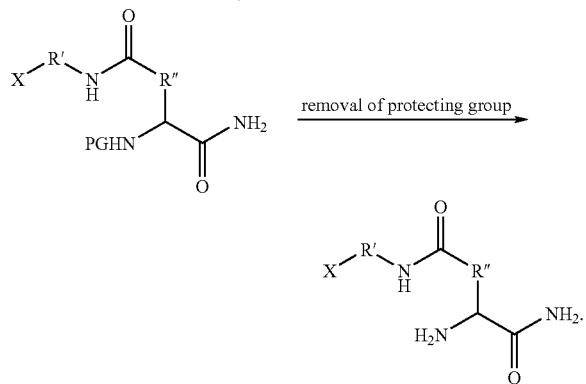

As defined in general Method (D)

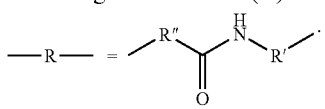

General Method (E): Synthesis of Ketogroup-Containing Amino Acid Amides from Cysteine A conveniently N-protected cysteine derivative (for instance an ester, N-(2,4-dimethoxybenzyl)amide or N-bis (cyclopropyl)methyl amide) or conveniently N-protected cysteine amide is treated with a carbonyl-group-containing alkylating agent ($R^{50}CO(CH_2)_nLG''$, LG''=leaving group for nucleophilic displacement selected from halogen, sulfonate (—O—SO$_2$—R$^{51}$), dialkylsulfonium, phenyliodonium, or hydroxy, wherein $R^{51}$ represents $C_{1-6}$alkyl, partially or completely fluorinated $C_{1-6}$alkyl, or aryl, optionally substituted with alkyl, halogen, nitro, cyano, or acetamido, and $R^{50}$ represents hydrogen, alkyl, aryl, or heteroaryl, said aryl or heteroaryl being optionally substituted once or several times with $C_{1-6}$alkoxy, hydroxy, halogen, cyano, acyl, alkyl, or nitro, under suitable reaction conditions to yield an S-alkylated cysteine derivative. This derivative is converted into an amino acid amide by conversion of the acid derivative into an amide and deprotection of the alpha-amino group. Suitable N-protecting groups are for instance trityl, phthaloyl, or alkoxycarbonyl groups, such as tert-butyloxycarbonyl

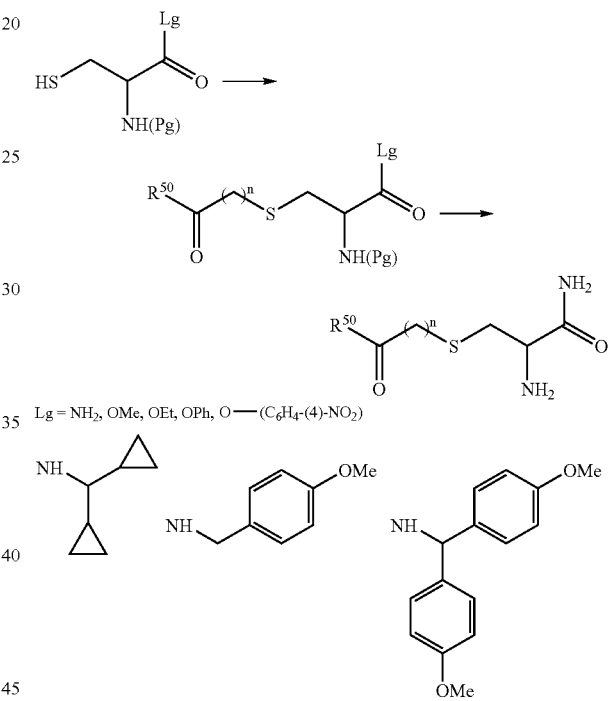

wherein n represents an integer from 1 to 10.

General Method (F): Synthesis of Ketogroup-Containing Amino Acid Amides from Aspartic or Glutamic Acid Aspartic or glutamic acids can be selectively protected by treatment of an N-alkoxycarbonyl derivative with formaldehyde, to yield cyclic esters as shown below:

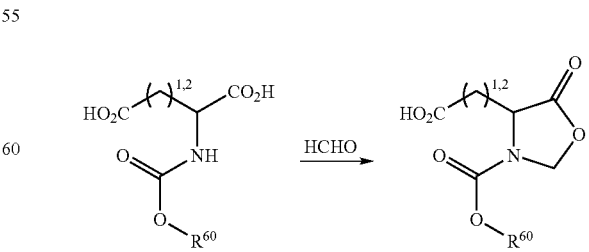

These derivatives, in which $R^{60}$ represents tert-butyl, benzyl, 2-chlorobenzyl, allyl, 2-(trimethylsilyl)ethyl, 2,2,2- trichloroethyl, or benzhydryl, can be converted to protected, ketone-containing amino acid derivatives by activation of the carboxylic acid (LvG representing halogen, aryloxy, or heteroaryloxy) and reaction with a carbon nucleophile $R^{80}$-$M^1$, in which $R^{80}$ represents alkyl, aryl, or heteroaryl, said aryl or heteroaryl being optionally substituted once or several times with $C_{1-6}$alkoxy, hydroxy, halogen, cyano, acyl, alkyl, or nitro, and in which $M^1$ represents an alkali metal, Mg, Zn, Ti, Zr, Mn, Cu, Ce, or Ca, optionally in the presence of a suitable catalyst. Reaction of the product with ammonia and deprotection will yield the desired amino acid amide

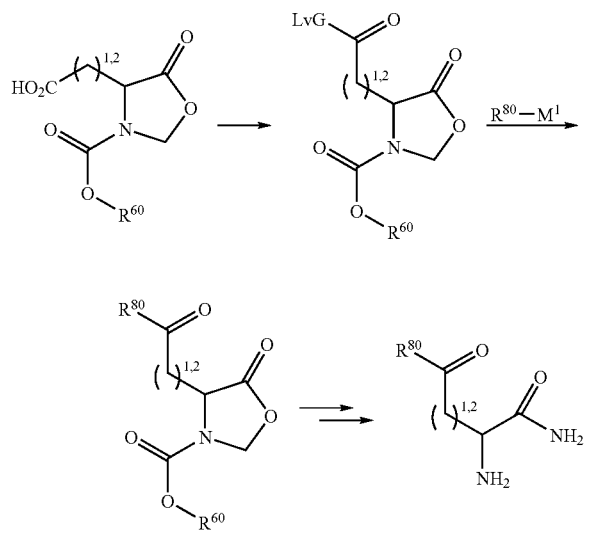

Similarly, reaction of N-alkoxycarbonyl pyroglutamic acid esters, in which $R^{70}$ represents tert-butyl, benzyl, 2-chlorobenzyl, allyl, 2-(trimethylsilyl)ethyl, 2,2,2-trichloroethyl, or benzhydryl, and $R^{80}$ represents lower alkyl, with nucleophilic carbon reagents can yield protected, keto-group-containing amino acid derivatives. Reaction of the product with ammonia and deprotection will yield the desired amino acid amide:

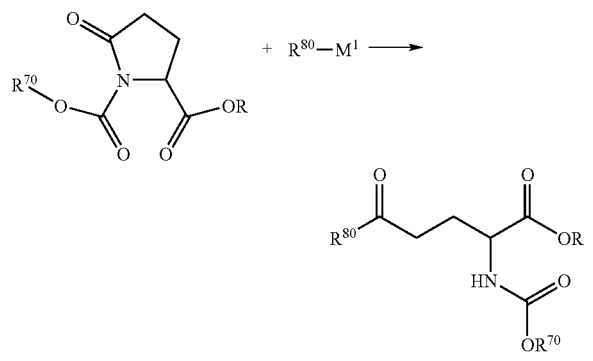

Similarly, suitably N-protected glutamic acid diesters as those shown below, in which $R^{90}$ represents lower alkyl, can be selectively acylated at carbon to yield, after hydrolysis and decarboxylation, protected derivatives of keto-group-containing amino acids, which can be converted into amino acid amides using standard procedures

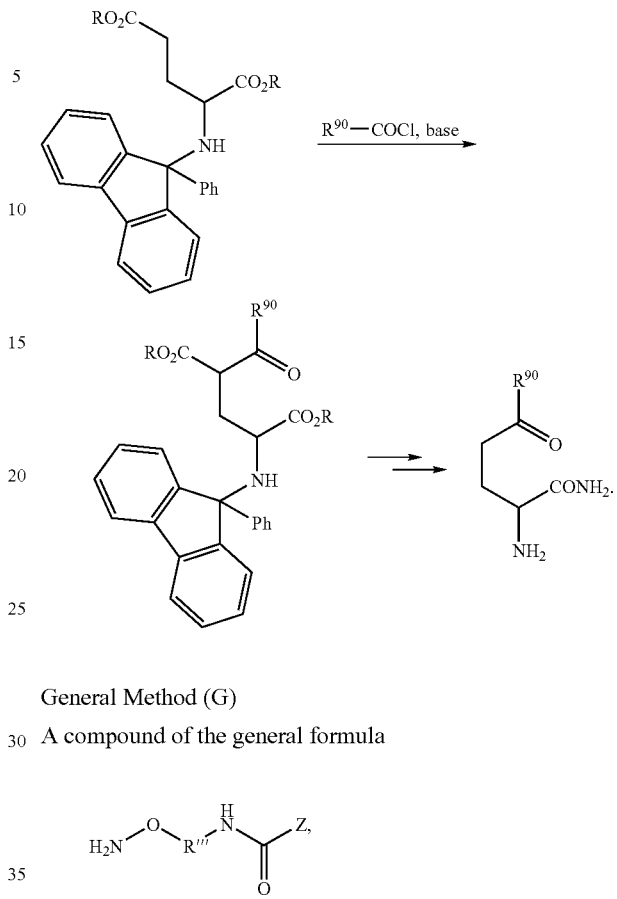

General Method (G)

A compound of the general formula

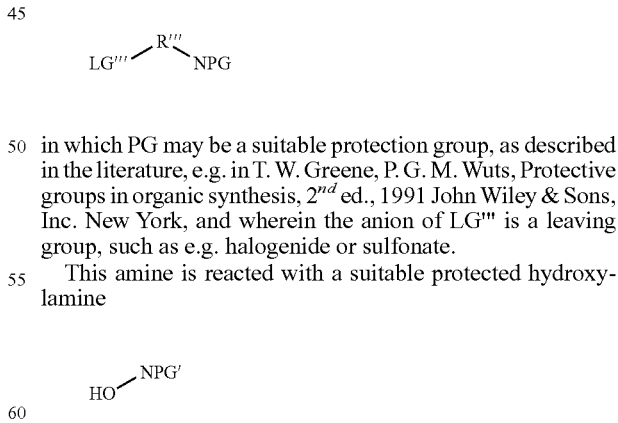

wherein R''' represents $C_{1-15}$alkylene, $C_{2-15}$alkenylene, $C_{2-15}$alkynylene, $C_{1-15}$heteroalkylene, $C_{2-15}$heteroalkenylene, $C_{2-15}$heteroalkynylene, wherein one or more homocyclic aromatic compound biradical or heterocyclic compound biradical may be inserted, may be prepared from a suitable protected primary or secondary amine $$LG''' \diagdown^{R'''} \diagdown NPG$$

in which PG may be a suitable protection group, as described in the literature, e.g. in T. W. Greene, P. G. M. Wuts, Protective groups in organic synthesis, $2^{nd}$ ed., 1991 John Wiley & Sons, Inc. New York, and wherein the anion of LG''' is a leaving group, such as e.g. halogenide or sulfonate.

This amine is reacted with a suitable protected hydroxylamine $$HO \diagdown^{NPG'}$$

wherein PG' is a protecting group, which is chosen in a way that PG can be removed from an amine without removal of PG' from the hydroxylamine. Examples for that can be found in the literature, e.g. in T. W. Greene, P. G. M. Wuts, Protective groups in organic synthesis, $2^{nd}$ ed., 1991 John Wiley & Sons, Inc. New York.

The two components are reacted under basic conditions such as e.g. sodium hydride at a suitable temperature such as e.g −78° C. to 200° C.

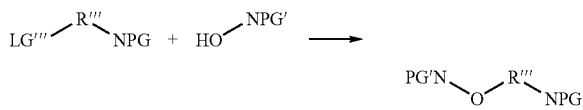

The protecting group of the amine may be removed selectively with a method described in the literature

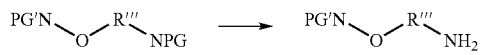

The amine may be acylated with a suitable acid and a coupling reagent such as e.g. 1-hydroxybenzotriazole, 3,4-dihydro-3-hydroxybenzotriazin-4-one or 7-azabenzotriazole in combination with e.g. a carbodiimide such as e.g. diisopropylcarbodiimide or 1-(3-dimethylaminopropyl)-3-ethyl-carbodiimide hydrochloride in the presence or absence of a suitable base such as e.g. triethylamine or ethyldiisopropylamine to give an amide.

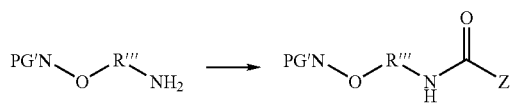

Finally, the protecting group of the hydroxylamine may be removed by a method described in the literature, e.g. in T. W. Greene, P. G. M. Wuts, Protective groups in organic synthesis, $2^{nd}$ ed., 1991 John Wiley & Sons, Inc. New York

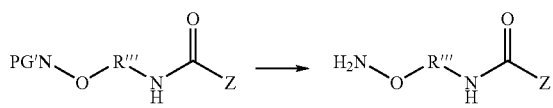

General Method (H)

A compound of the general formula

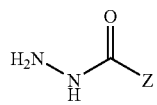

may be prepared from a suitable ester, in which $R^{IV}$ is $C_{1-10}$alkyl in a suitable solvent such as ethanol by addition of hydrazine hydrate.

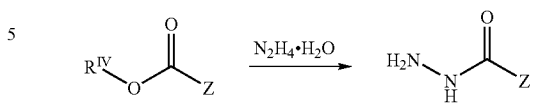

General Method (J) Transacylation Reaction

At a suitable temperature such as e.g. 5-50° C. or room temperature, a solution of the peptide in question (final concentration 1-10 mM) and the nucleophile in question (final concentration 10 mM-2M) is dissolved or suspended in water containing low concentrations of EDTA.

Organic solvents may be added to improve the solubility of the reactants. The mixture may be buffered to a suitable pH-value such as e.g. between pH 1 and pH 14, between e.g. between pH 3.5 and pH 9, between pH 6 and pH 8.5, with a suitable buffer such as e.g. phosphate buffer or HEPES, or the pH can be maintained by addition of base or acid. A suitable enzyme e.g. carboxypeptidase Y is added to the said mixture of peptide and nucleophile. The reaction may be stopped after a suitable time e.g. between 5 min and 10 days, by changing temperature or pH-value, by adding organic solvents, or by dialysis or gel filtration.

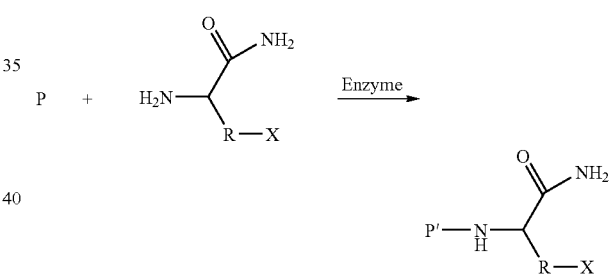

The pH of choice is determined e.g. by the solubility of the peptide to be conjugated and the activity of the enzyme to be used. Solubility of peptides is to a large extent determined by the pKa of the peptide. Normally, the solubility of a given peptide is at its minimum when pH equals pKa of the peptide. It lies within the skills of a skilled person to choose a pH at which to run the reaction taking due care to the above considerations.

General Method (K) Oxime Formation

An oxime moiety may be formed by dissolving the transacylated peptide in question, in which $R^V$ may be a substituted or unsubstituted aromatic ring, a substituted or an unsubstituted heteroaromatic ring, hydrogen, or $C_{1-10}$alkyl, in water. Organic solvents may be added to increase solubility. The solution is buffered to a suitable pH-value such as e.g. between pH 0 and pH 14, between pH 3 and pH 6, or pH 5 and kept at a suitable temperature such as e.g. 0-60° C. The hydroxylamine in question is added, and oxime moiety is formed according to the reaction scheme below

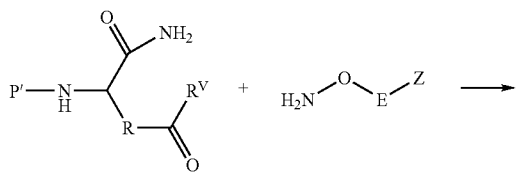

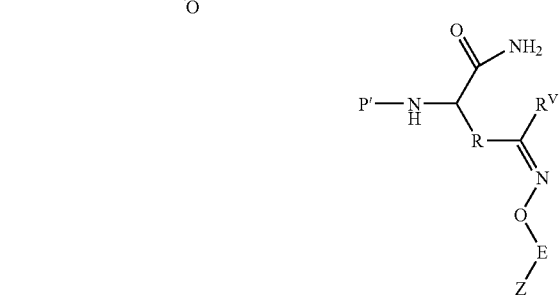

The pH of choice is determined e.g. by the solubility of the peptide to be. Solubility of peptides is to a large extent determined by the pKa of the peptide. Normally, the solubility of a given peptide is at its minimum when pH equals pKa of the peptide. It lies within the skills of a skilled person to choose a pH at which to run the reaction taking due care to the above consideration.

General method (L) Hydrazone Formation

Hydrazone Formation (I)

An hydrazone moiety is formed by dissolving the transacylated peptide in question, in which $R^{VI}$ may be a substituted or unsubstituted aromatic ring, a substituted or an unsubstituted heteroaromatic ring, hydrogen, or $C_{1-10}$alkyl, in water. The solution is buffered to a suitable pH-value such as e.g. between pH 2 and pH 14 or between pH 0 and pH 4 and kept at a suitable temperature such as e.g. 0-60° C. The hydrazide in question is added, whereby the hydrazone is formed

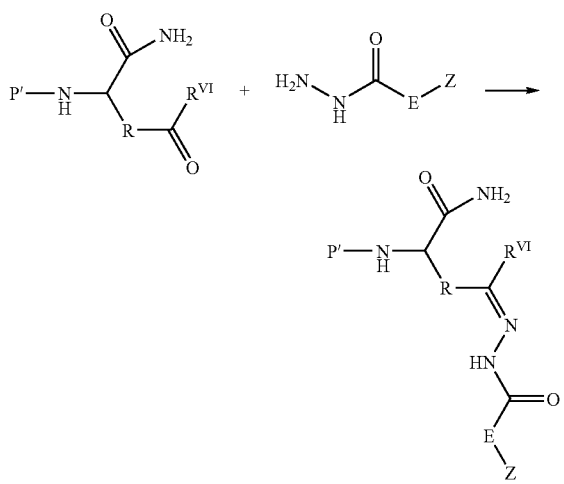

Hydrazone Formation (II)

An hydrazone is formed by dissolving the transacylated peptide in question, in which $R^{VII}$ may be a substituted or unsubstituted aromatic ring, a substituted or an unsubstituted heteroaromatic ring, hydrogen, or $C_{1-10}$alkyl, in water. The solution is buffered to a suitable pH value such as e.g. between pH 2 and pH 14 or between pH 0 and pH, 4 and kept at a suitable temperature such as e.g. 0-60° C. The hydrazine in question is added, whereby the hydrazone is formed

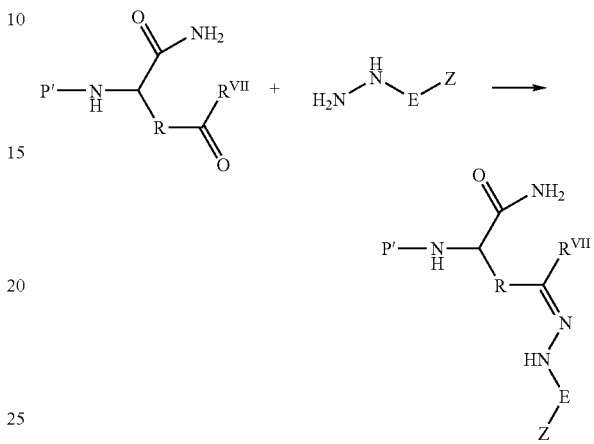

General Method (M) Isoxazole Formation

An isoxazole can be formed by reaction between a nitril-oxide and an alkyne. The nitril-oxide is formed by addition of a suitable oxidation-reagent such as e.g. bleach to an excess of a suitable oxime. A solution of an excess of the freshly formed nitrile-oxide may be added to the peptide in question.

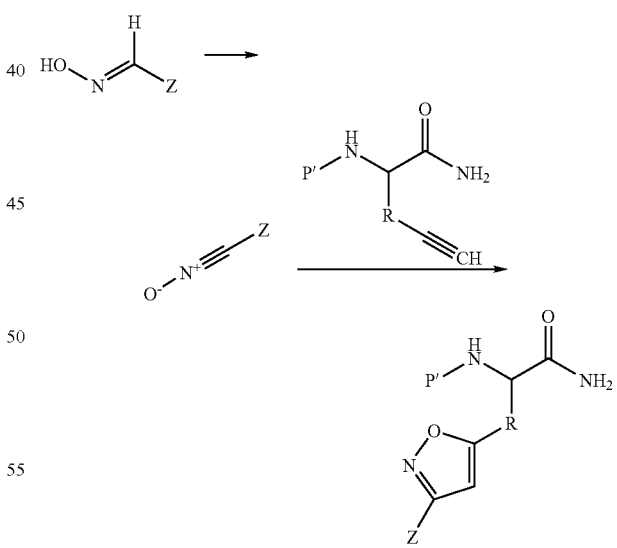

General Method (N) Triazole Formation

A triazole can be formed by reaction between an azide which is attached to the group Z and an alkyne, which is attached to the peptide in question, in the presence of Cu(1)-ions in a suitable solvent such as water or a mixture of water and an organic solvent such as e.g. acetonitrile. The triazole may be formed in two possible regioisomers.

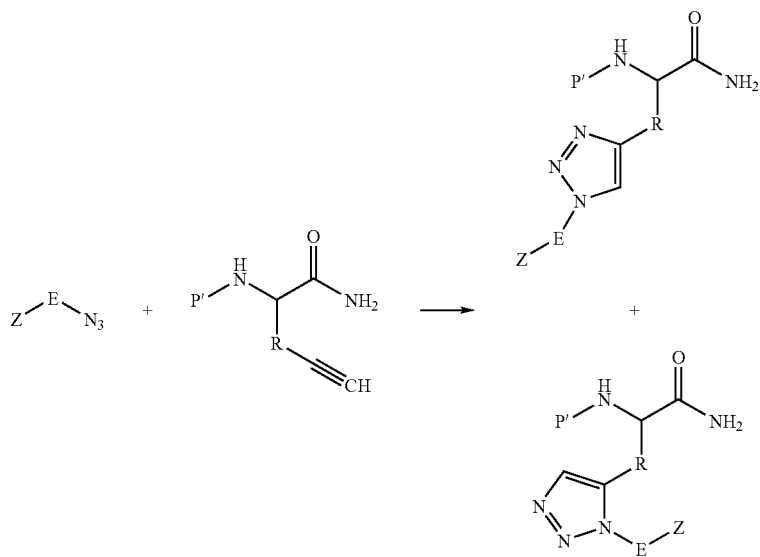

General Method (O) Triazole Formation

A triazole can be formed by reaction between an alkyne which is attached to the group Z and an azide, which is attached to the peptide in question, in the presence of Cu(1)-ions in a suitable solvent such as water or a mixture of water and an organic solvent such as e.g. acetonitrile. The triazole may be formed in two possible regioisomers.

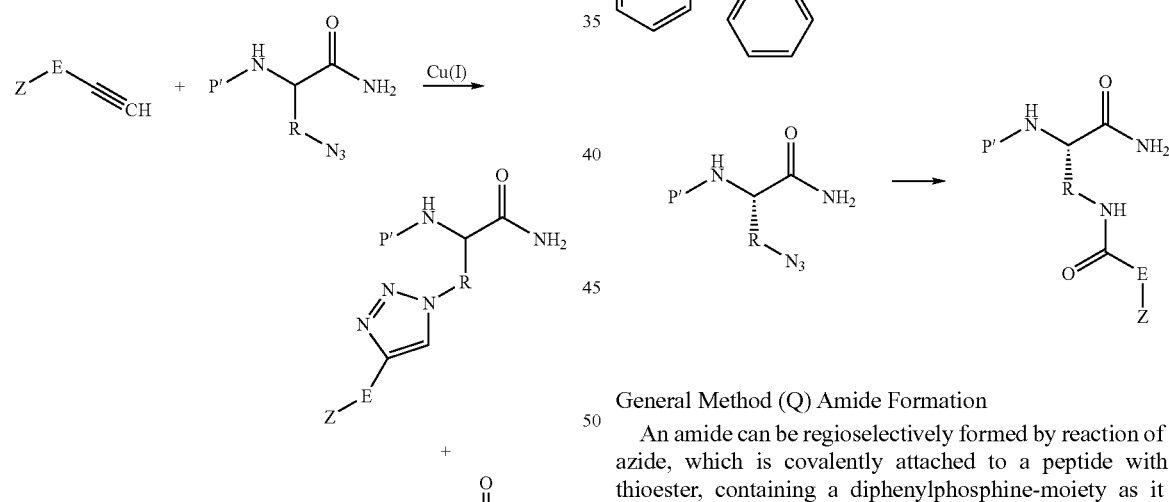

General Method (P) Amide Formation

An amide can be regioselectively formed by reaction of an azide, which is covalently attached to a peptide with an ester, containing a triphenylphosphine-moiety as it is described in e.g. *Tetrahedron Lett.* 2003, 44, 4515-4518.

General Method (Q) Amide Formation

An amide can be regioselectively formed by reaction of an azide, which is covalently attached to a peptide with a thioester, containing a diphenylphosphine-moiety as it is described in e.g. *J. Org. Chem.* 2002, 67, 4993-4996.

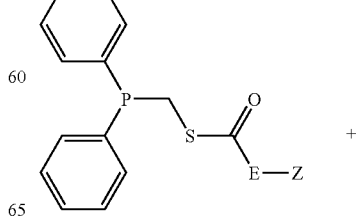

-continued

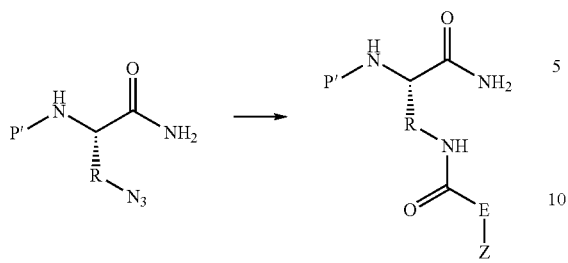

General Method (R) Arylalkyne Formation

An arylalkyne can be formed by reaction between an alkyne, which is covalently attached to a peptide and a haloaryl compound in the presence of a palladium catalyst, which is water-soluable, as described in e.g. *Bioconjugate Chemistry*, 2004, 15, 231-234. The haloaryl compound may be exchanged with the corresponding aryl trifluorosulfonate.

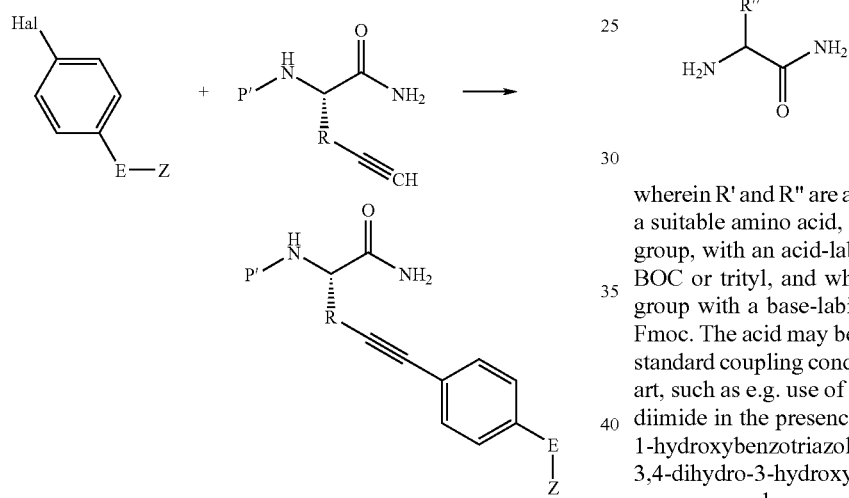

General Method (R) Arylalkyne Formation

An arylalkyne might be formed by reaction between a haloaryl-moiety, which is covalently attached to a peptide and an alkyne in the presence of a palladium catalyst, which is water-soluable, as described in e.g. *Bioconjugate Chemistry*, 2004, 15, 231-234. Instead of the haloaryl-moiety a trifluorosulfonyloxyaryl-moiety, which is attached to a peptide can be used as well.

-continued

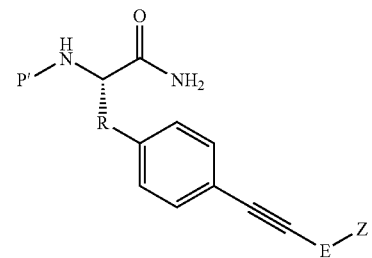

General Method (T)

A compound of the general formula

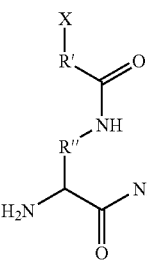

wherein R' and R" are as defined above may be prepared from a suitable amino acid, which is protected at the alpha-amino group, with an acid-labile protecting group PG' such as e.g. BOC or trityl, and which is protected at the omega-amino group with a base-labile protecting group $PG^2$ such as e.g. Fmoc. The acid may be attached to a Rink-amide resin using standard coupling conditions known to a person skilled in the art, such as e.g. use of a carbodiimide e.g. diisopropylcarbodiimide in the presence or absence of a reagent such as e.g. 1-hydroxybenzotriazole, 1-hydroxy-7-azabenzotriazole or 3,4-dihydro-3-hydroxy-4-oxo-1,2,3-benzotriazin and in the presence or absence of a base such as e.g. triethylamine or ethyldiisopropylamine. The protecting group at the omega-amine $PG^2$, may be removed under basic conditions described for the particular protecting group in the literature such as e.g. T. W. Greene, P. G. M. Wuts, Protective groups in organic synthesis, $2^{nd}$ ed., 1991 John Wiley & Sons, Inc. New York.

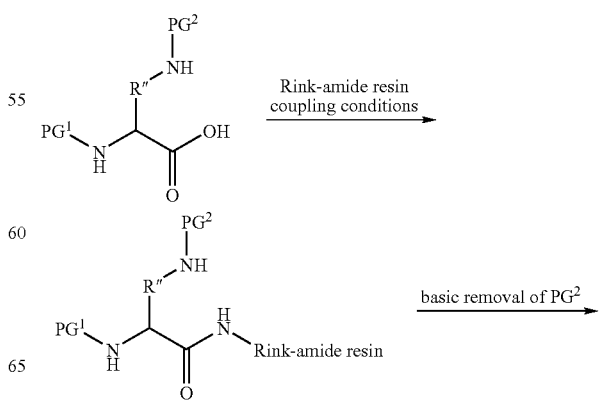

-continued

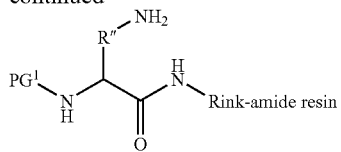

An acid can be attached to the omega amino moiety using standard coupling conditions, such as e.g. use of a carbodiimide e.g. diisopropylcarbodiimide in the presence or absence of a reagent such as e.g. 1-hydroxybenzotriazole, 1-hydroxy-7-azabenzotriazole or 3,4-dihydro-3-hydroxy-4-oxo-1,2,3-benzotriazin and in the presence or absence of a base such as e.g. triethylamine or ethyldiisopropylamine. The intermediate may be cleaved from the solid support under acidic conditions such as e.g. trifluoroacetic acid or a 20-70% solution of trifluoroacetic acid in dichloromethane to give the desired aminamide.

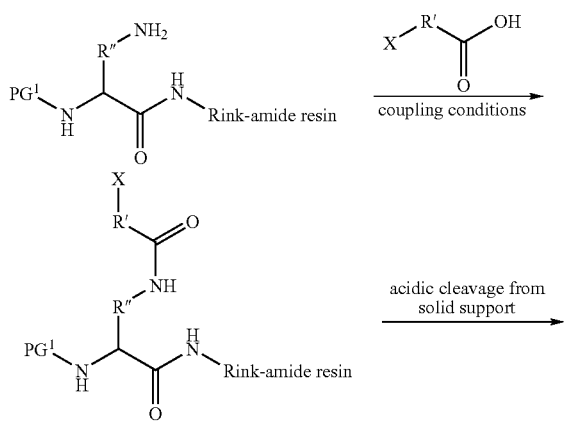

General Method (U)

A compound of the general formula

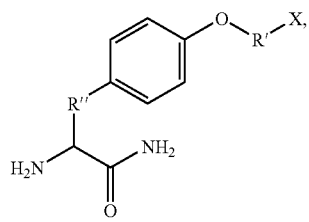

wherein R' and R" are defined as above, may be prepared from a suitable amino acid, which is protected with an acid labile protecting group PG¹, such as e.g. Boc or trityl, which is reacted with an excess of ammonia in the presence of a coupling reagent, such as e.g. a carbodiimide e.g. diisopropylcarbodiimide in the presence or absence of a reagent such as e.g. 1-hydroxybenzotriazole, 1-hydroxy-7-azabenzotriazole or 3,4-dihydro-3-hydroxy-4-oxo-1,2,3-benzotriazin.

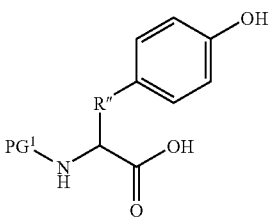

The phenolic hydroxyl group may be alkylated with a suitable halogenide or sulfonate, in which $R^a$ is any suitable substituted alkyl or aryl radical, in the presence of a suitable base such as e.g. potassium carbonate or tetramethylguanidine. The protecting group PG¹ may be removed from the alpha amino acid under acidic conditions and described in the literature for the particular protecting group chosen e.g. in T. W. Greene, P. G. M. Wuts, Protective groups in organic synthesis, $2^{nd}$ ed., 1991 John Wiley & Sons, Inc. New York, to give the desired amino amide.

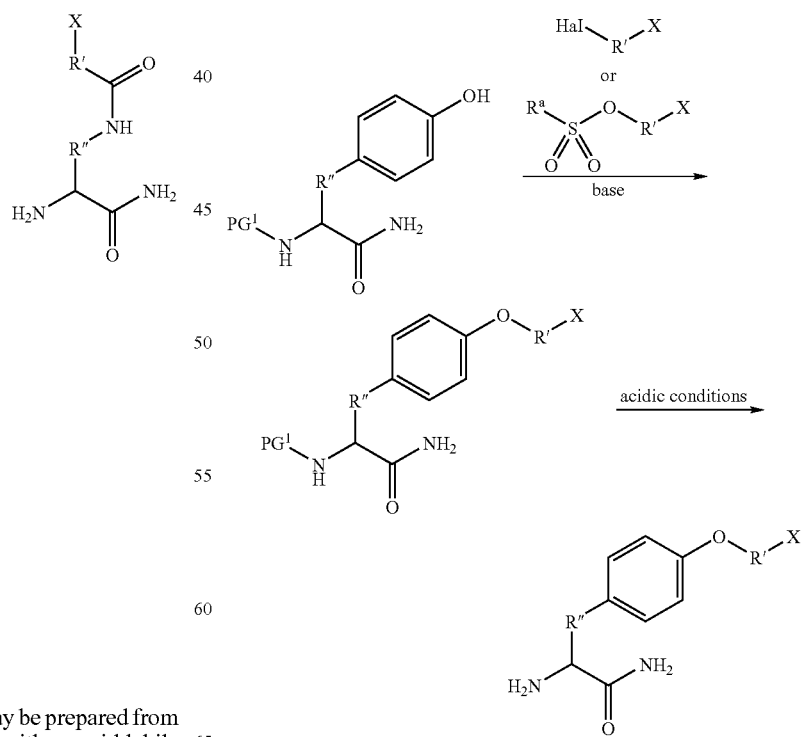

General Method (V) PEG-Reagent

A reagent of the general formula

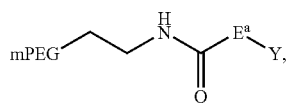

in which

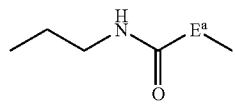

is E, as defined above, may be prepared from a suitable acid, which may be activated by reaction with a suitable reagent or a combination of reagents, such as e.g. 2-succinimido-1,1,3,3,-tetramethyluronium tetrafluoroborate (TSTU) in a suitable solvent such as e.g. N,N-dimethylformamide. The activated acid e.g. the obtained 2,5-dioxopyrrodin-1yl ester of said acid may be reacted with commercially available PEG-reagents, which are functionalized with a primary amine, optionally in the presence of a suitable base such as e.g. ethyldiisopropylamine or triethylamine.

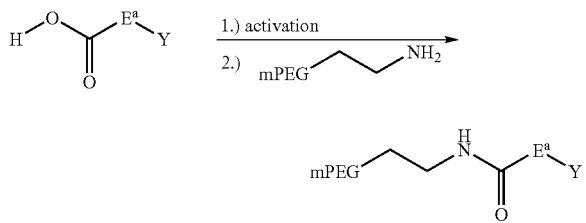

Example 1

(2S)-2-Amino-6-(4-oxo-4-phenylbutyrylamino)hexanoic acid amide

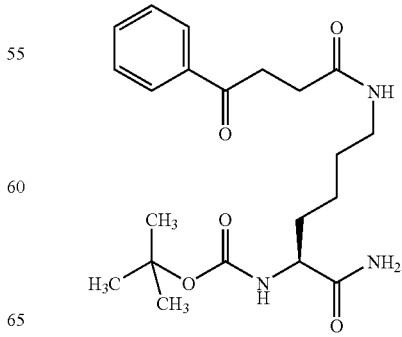

Step A:

(2S)-2-tert-(Butoxycarbonylamino)-6-(4-oxo-4-phenylbutyrylamino)hexanoic acid methyl ester

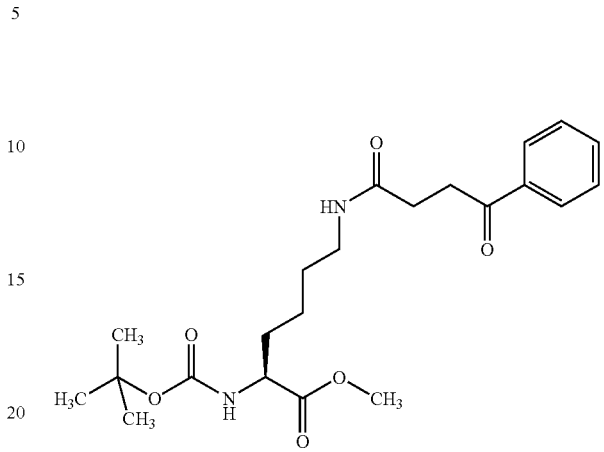

1-(3-Dimethylaminopropyl)-3-ethylcarbodiimide hydrochloride (3.23 g, 16.8 mmol) was added to a solution of benzoylpropionic acid (3.00 g, 16.8 mmol) and 3,4-dihydro-3-hydroxybenzotriazin-4-one (2.75 g, 16.8 mmol) in a mixture of N,N-dimethylformamide (20 ml) and dichloromethane (20 ml). The reaction mixture was stirred for 20 min at room temperature. The hydrochloride salt of BOC-Lys-OMe (5.00 g, 16.8 mmol) and ethyldiisopropylamine (8.65 ml, 50.5 mmol) were added successively. The reaction mixture was stirred for 16 h. It was diluted with ethyl acetate (300 ml) and washed with a half-concentrated solution of sodium hydrogencarbonate (2×300 ml). The organic layer was dried over magnesium sulphate. The solvent was removed in vacuo. The crude product was purified by flash chromatography on silica (90 g), using ethyl acetate/heptane 2:1 as eluent, to give 2.41 g of (2S)-2-tert-(butoxycarbonylamino)-6-(4-oxo-4-phenylbutyrylamino)hexanoic acid methyl ester.

$^1$H-NMR (CDCl$_3$): δ 1.30-1.90 (m, 6H); 1.44 (s, 9H); 2.61 (t, 2H); 3.20 (q, 2 H; 3.37 (t, 2 H); 4.25 (m, 1H); 5.20 (br, 1H); 5.90 (br, 1H); 7.46 (m, 2H); 7.50 (m, 1H); 8.00 (d, 2 H).

Step B:

[(1S)-1-Carbamoyl-5-(4-oxo-4-phenylbutyrylamino)pentyl]carbamic acid tert-butyl ester A 25% solution of ammonia in water (25 ml) was added to (2S)-2-tert-(butoxycarbonylamino)-6-(4-oxo-4-phenylbutyrylamino)hexanoic acid methyl ester (0.70 g, 1.67 mmol). The reaction mixture was stirred for 2 days at room temperature. The solvent was removed in vacuo to give 0.56 g of [(1S)-1-carbamoyl-5-(4-oxo-4-phenylbutyrylamino)pentyl]carbamic acid tert-butyl ester.

$^1$H-NMR (CDCl$_3$): δ 0.90 (m, 6H); 2.75 (t, 2H); 3.20-3.50 (m, 4H); 4.15 (m, 3H); 8.00 (d, 2H).

Step C:

Trifluoroacetic acid (25 ml) was added to a solution of [(1S)-1-carbamoyl-5-(4-oxo-4-phenylbutyrylamino)pentyl]carbamic acid tert-butyl ester (0.56 g, 1.38 mmol) in dichloromethane (25 ml). The reaction mixture was stirred for 1 h at room temperature. The solvent was removed. The crude product was purified by HPLC on a RP-18 column, using a gradient of 20-45% acetonitrile in water, containing 0.1% of trifluoroacetic acid as buffer to give 92 mg of the title compound with a purity of approx. 85%, which was used for the further experiments.

$^1$H-NMR (CDCl$_3$): δ 1.40 (m, 4H); 1.70 (m, 2H); 2.46 (t, 2H); 3.00 (q, 2H); 3.23 (t, 2 H); 3.70 (m, 1H); 7.53 (m, 3H); 7.65 (t, 1H); 7.83 (br, 1H); 7.90 (t, 1H); 8.00 (d, 2H); 8.05 (br, 3 H).

MS: m/z=306 [M+1]$^+$

4-Acetyl-N-((5S)-5-amino-5-carbamoylpentyl)benzamide

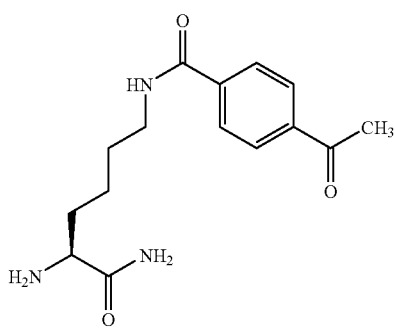

Step A:

1.65 g of the title compound was prepared as described for (2S)-2-amino-6-(4-oxo-4-phenylbutyrylamino)hexanoic acid amide, using 4-acetylbenzoic acid instead of benzoylpropionic acid.

$^1$H-NMR (CDCl$_3$): δ 1.40 (m, 2H); 1.60 (m, 2H); 1.80 (m, 2H); 2.62 (s, 3H); 3.30 (q, 2 H); 3.75 (q, 1H); 7.55 (br, 1H); 7.85 (br, 1H); 7.97 (d, 2H); 8.05 (d, 2H); 8.10 (br, 3H); 8.65 (t, 1 H).

S-Phenacylcysteine amide hydrochloride

Step A: S-Phenacyl-N-Boc-cystein methyl ester

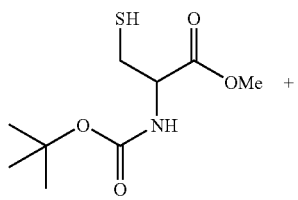

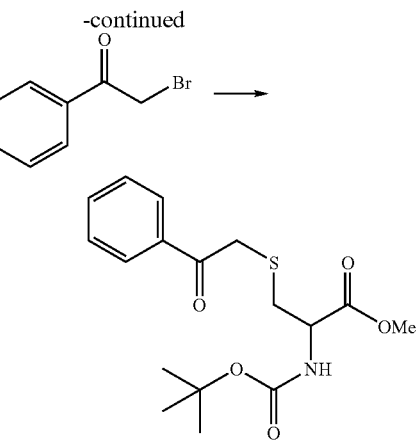

To a solution of the N-Boc cysteine methyl ester (2.05 ml, 9.93 mmol) in MeCN (20 ml) at 0° C. were added DIPEA (3.55 ml, 20.1 mmol), NaI (0.48 g, 3.20 mmol), and then a solution of phenacyl bromide (2.41 g, 12.1 mmol) in MeCN (4 ml). The mixture was stirred at room temperature for 19 h. Water (100 ml) and 1N aqueous HCl. (30 ml) was added, and the product was extracted (3×AcOEt). The combined extracts were washed with brine, dried (MgSO$_4$), and concentrated under reduced pressure to yield 4.37 g of an oil. Crystallization from AcOEt (approx 10 ml) and heptane (approx 40 ml) at −20° C. overnight yielded 3.49 g (99%) of the title methyl ester as a brown solid.

$^1$H NMR (DMSO-d$_6$): δ 1.37 (s, 9H), 2.74 (dd, J=9 Hz, 13 Hz, 1H), 2.89 (dd, J=5.5 Hz, 13 Hz, 1H), 3.62 (s, 3H), 4.03 (d, J=15 Hz, 1H), 4.14 (d, J=15 Hz, 1H), 4.22 (m, 1H), 7.33 (br d, J=8 Hz, 1H), 7.52 (m, 2H), 7.64 (m, 1H), 7.99 (m, 2H).

Step B: S-Phenacyl-N-Boc cysteine amide

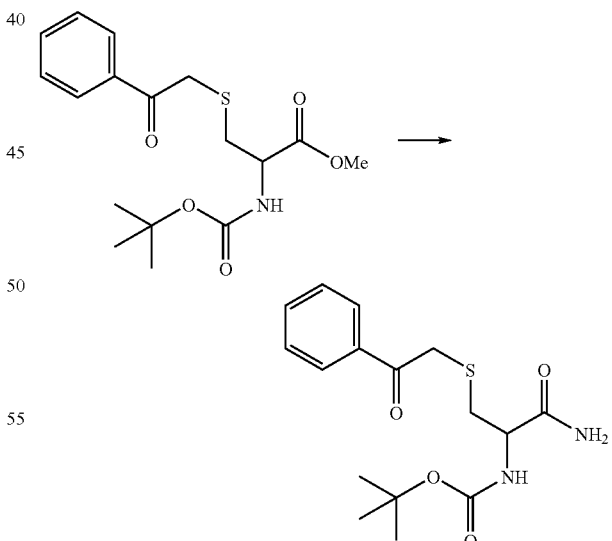

To a solution of S-phenacyl-N-Boc-cystein methyl ester (1.77 g, 5.01 mmol) in MeCN (30 ml) was added aqueous ammonia (50 ml, 25%; 12.5 g NH$_3$). After stirring at room temperature for 71 h no more starting material could be detected by TLC. The mixture was concentrated under reduced pressure, and the residue was resuspended in toluene and ethanol and concentrated again. stripping with PhMe+ EtOH. Crystallization from cold methanol yielded 0.86 g (50%) of the title amide.

$^1$H NMR (DMSO-$d_6$): δ 1.37 (s, 9H), 2.66 (dd, J=9 Hz, 13 Hz, 1H), 2.83 (dd, J=5.5 Hz, 13 Hz, 1H), 4.07(d, J=15 Hz, 1H), 4.10(m, 1H), 4.12 (d, J=15 Hz, 1H), 6.88(br d, J=8 Hz, 7.12 (br s, 1H), 7.35 (br s, 1H), 7.52 (t, J=8 Hz, 2H), 7.64 (m, 1H), 7.96 (m, 2H).

Step C S-Phenacylcysteine amide hydrochloride

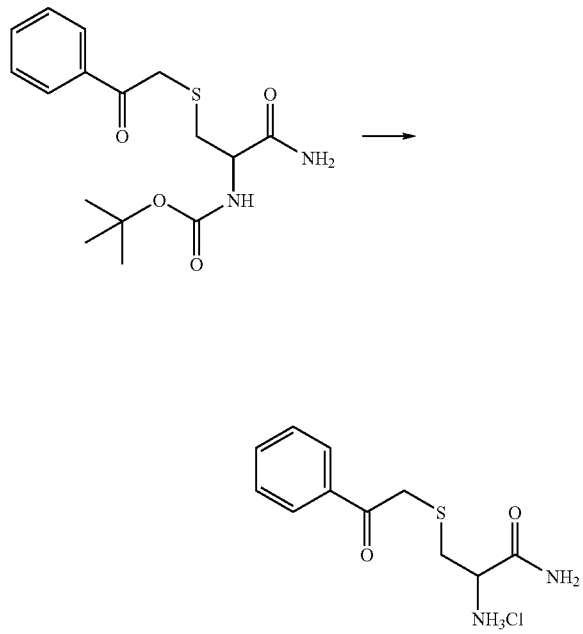

S-Phenacyl-N-Boc cysteine amide (0.70 g, 2.07 mmol) was mixed with DCM (10 ml) and TFA (20 ml). After 30 min the mixture was concentrated, and the residue was mixed with toluene and MeCN and concentrated again. The residue was mixed with 1N HCl (1.5 ml), ethanol, MeCN, and toluene and concentrated again. The residue was suspended in boiling EtOH (approx 5 ml).

Filtration and drying yielded 0.18 g (32%) of the title hydrochloride as a light brown solid. LCMS: only one product (HPLC, 210 nm), MH$^+$=221 (product−water).

$^1$H NMR (DMSO-$d_6$): δ 2.93 (dd, J=7 Hz, 13 Hz, 1H), 3.06 (dd, J=6 Hz, 13 Hz, 1H), 3.97(m, 1H), 4.33 (br s, 2H), 7.58 (m, 2H), 7.68 (m, 1H), 8.02 (m, 2H), 8.32 (br s, 3H).

Example 4

4-Acetyl-N-((5S)-5-amino-5-carbamoylpentyl)benzamide

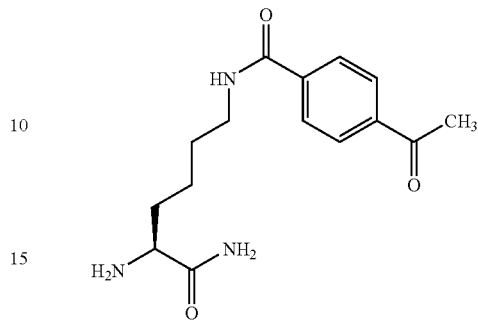

Rink-amide-resin (loading: 0.43 mmol/g, 6.66 g, 2.86 mmol) was swelled with dichloromethane (50 ml). The solvent was removed. A 20% solution of piperidine in N-methylpyrrolidinone was added (50 ml). The reactor was shaken for 20 min. The liquid was removed. The resin was washed with N-methylpyrrolidinone (3×50 ml) and dichloromethane (5×50 ml). A solution of BOC-Lys(FMOC)-OH (5.37 g, 11.5 mmol) in N-methylpyrrolidinone (50 ml) and a solution of 1-hydroxybenzotriazole (1.75 g, 11.5 mmol) in N-methylpyrrolidinone (20 ml) were added successively. Diisopropylcarbodiimide (1.79 ml, 11.5 mmol) and ethyldiisopropylamine (1.96 ml, 11.5 mmol) were added. The reactor was shaken at room temperature for 16 h. The liquid was removed. The resin was washed with N-methylpyrrolidinone (3×50 ml) and dichloromethane (3×50 ml). A solution of 4-acetylbenzoic acid (2.82 g, 11.5 mmol) in N-methylpyrrolidinone (50 ml) and a solution of 1-hydroxybenzotriazole (1.75 g, 11.5 mmol) in N-methylpyrrolidinone (20 ml) were added successively. Diisopropylcarbodiimide (1.79 ml, 11.5 mmol) and ethyldiisopropylamine (1.96 ml, 11.5 mmol) were added. The reactor was shaken at room temperature for 16 h. The resin was washed with N-methylpyrrolidinone (3×50 ml) and dichloromethane (3×50 ml). A solution of 50% of trifluoroacetic acid and 10% triisopropylsilane in dichloromethane (50 ml) was added to the resin. The reaction vessel was shaken for 1 h at room temperature. The liquid was collected. The solvent was removed in vacuo. The residue was redissolved in toluene (50 ml). The solvent was removed in vacuo.

The crude products of 6 runs of the procedure described above were combined. They were purified by HPLC-chromatography on a $C_{18}$-reversed phase column, using a gradient of 3-23% of acetonitrile in water in a 0.1% buffer of trifluoroacetic acid to afford 1.07 g of the trifluoroacetic acid salt of 4-acetyl-N-((5S)-5-amino-5-carbamoylpentyl)benzamide.

Example 5

1-[4(2-(Aminooxy)ethyl)piperidin-1-yl]hexadecan-1-one

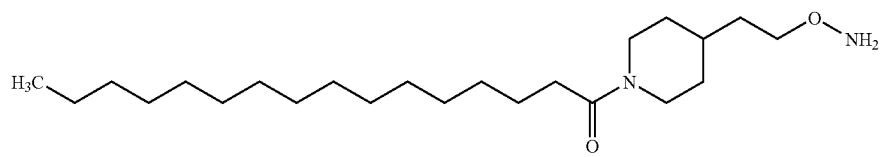

Step 1:

4-[2-(Toluene-4-sulfonyloxy)ethyl]piperidine-1-carboxylic acid tert-butyl ester

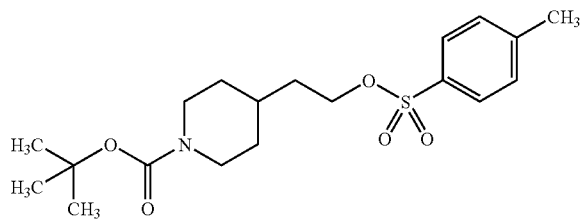

Tosyl chloride (4.16 g, 21.8 mmol) was added to a solution of commercially available 4-(2-hydroxyethyl)piperidine-1-carbocylic ester tert-butyl ester (e.g Aldrich 54,724-7, 5.0 g, 21.8 mmol) and triethylamine (4.25 ml, 30.5 mmol) in dichloromethane (100 ml). The reaction mixture was stirred at room temperature for 16 h. It was diluted with ethyl acetate (300 ml) and washed with a 10% aqueous solution of sodium hydrogensulphate (200 ml). The aqueous phase was extracted with ethyl acetate (150 ml). The combined organic layers were washed with a saturated aqueous solution of sodium hydrogencarbonate (250 ml) and dried over magnesium sulphate. The solvent was removed in vacuo. The crude product was purified by flash chromatography on silica (80 g), using ethyl acetate/heptane first: 1:2 then 1:1 as eluent, to give 6.04 g of 4-[2-(toluene-4-sulfonyloxy)ethyl]piperidine-1-carboxylic acid tert-butyl ester.

$^1$H-NMR (CDCl$_3$): δ 1.05 (m, 2H); 1.45 (s, 9H); 1.55 (m, 5H); 2.50 (s, 3H); 2.65 (t, 2 H); 4.05 (m, 4H); 7.35 (d, 2H); 7.80 (d, 2H).

Step 2:

4-[2-(1,3-Dioxo-1,3-dihydroisoindol-2-yloxy)ethyl]piperidine-1-carboxylic acid tert-butyl ester

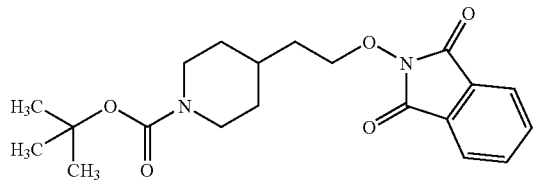

At 0° C., a 60% suspension of sodium hydride in mineral oil (0.69 g, 17.2 mmol) was added to a solution of N-hydroxyphthalimide (2.80 g, 17.2 mmol) in N,N-dimethylformamide (20 ml). The reaction mixture was stirred for 45 min at 0° C. A solution of 4-[2-(toluene-4-sulfonyloxy)ethyl]piperidine-1-carboxylic acid tert-butyl ester (5.99 g, 15.6 mmol) in N,N-dimethylformamide (15 ml) and tetrabutylammonium iodide (0.17 g, 0.47 mmol) were added successively. The reaction mixture was heated to 60° C. for 2 days and cooled to room temperature. Water (5 ml) was added carefully. The reaction mixture was diluted with ethyl acetate (250 ml) and washed with a 10% aqueous solution of sodium hydrogensulphate (200 ml). The aqueous phase was extracted with ethyl acetate (200 ml). The combined organic layers were washed with a saturated aqueous solution of sodium hydrogencarbonate (150 ml) and dried over magnesium sulphate. The solvent was removed in vacuo. The crude product was purified by flash chromatography on silica (80 g), using ethyl acetate/heptane 1:1 as eluent to give 4.36 g of 4-[2-(1,3-dioxo-1,3-dihydroisoindol-2-yloxy)ethyl]piperidine-1-carboxylic acid tert-butyl ester.

$^1$H-NMR (CDCl$_3$): δ 1.15 (m, 2H); 1.50 (s, 9H); 1.75 (m, 5H); 2.75 (m, 2H); 4.10 (m, 2 H); 4.30 (t, 2H); 7.80 (m, 4H).

Step 3:

2-(2-(Piperidin-4-yl)ethoxy)isoindole-1,3-dione

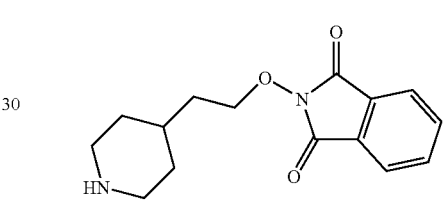

Trifluoroacetic acid (20 ml) was added to a solution of 4-[2-(1,3-dioxo-1,3-dihydroisoindol-2-yloxy)ethyl]piperidine-1-carboxylic acid tert-butyl ester (4.26 g, 11.4 mmol) in dichloromethane (20 ml). The reaction mixture was stirred at room temperature for 50 min. The solvent was removed in vacuo. The residue was dissolved in dichloromethane (50 ml) and the solvent was removed in vacuo. The latter procedure was repeated twice to give 6.46 g of the crude trifluoroacetate salt of 2-(2-(piperidin-4-yl)ethoxy)isoindole-1,3-dione.

MS: m/z=275 [M+1$^+$]

$^1$H-NMR (DMSO-d$_6$): δ 1.30 (m, 2H); 1.65 (m, 2H); 1.90 (m, 3H); 2.90 (q, 2H); 3.30 (d, 2 H); 4.20 (t, 2H); 7.90 (s, 4H); 8.30 (br, 1H); 8.65 (br, 1H).

Step 4:

2-[2-(1-(Hexadecanoyl)piperidin-4-yl)ethoxy]isoindole-1,3-dione

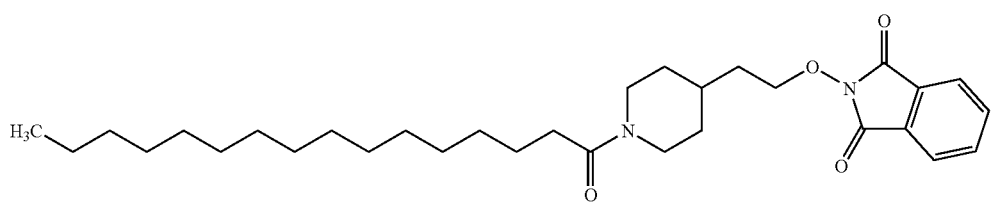

At 0° C., 1-(3-dimethylaminopropyl)-3-ethylcarbodiimide hydrochloride (1.04 g, 5.44 mmol) was added to a solution of palmic acid (1.40 g, 5.44 mmol) and 3,4-dihydro-3-hydroxy-4-oxo-1,2,3-benzotriazole (0.89 g, 5.44 mmol) in N,N-dimethylformamide (20 ml) and dichloromethane (20 ml). The reaction mixture was stirred at 0° C. for 20 min. A solution of the trifluoroacetate salt of 2-(2-(piperidin-4-yl)ethoxy)isoindole-1,3-dione (2.11 g, 5.44 mmol) in N,N-dimethylformamide (5 ml) and ethyldiisopropylamine (6.19 ml, 38.1 mmol) were added successively. The reaction mixture was stirred for 16 h, while it was warming up to room temperature. It was diluted with ethyl acetate (150 ml) and was washed with a 10% aqueous solution of sodium hydrogensulphate (150 ml). The aqueous phase was extracted with ethyl acetate. The combined organic layers were washed with a mixture of water (50 ml) and a saturated aqueous solution of sodium hydrogencarbonate (50 ml) and dried over magnesium sulphate. The crude product was purified by flash chromatography on silica (40 g), using ethyl acetate/heptane 1:1 as eluent to give 1.52 g of 2-[2-(1-(hexadecanoyl)piperidin-4-yl)ethoxy]isoindole-1,3-dione.

MS: m/z=513 [M+1$^+$]

$^1$H-NMR (DMSO-d$_6$): δ 0.90 (t, 3H); 1.10 (m, 2H); 1.25 (m, 26H); 1.45 (m, 2H); 1.65 (m, 1 H); 1.80 (m, 2H); 2.30 (t, 2H); 2.95 (t, 1H); 3.85 (m, 3H); 4.20 (t, 2H); 4.40 (d, 1H); 7.90 (s, 4 H).

Step 5:

Hydrazine hydrate (0.14 ml, 2.96 mmol) was added to a solution of 2-[2-(1-(hexadecanoyl)piperidin-4-yl)ethoxy]isoindole-1,3-dione (1.52 g, 2.96 mmol) in ethanol (30 ml). The reaction mixture was heated to reflux for 75 min and cooled to room temperature. The formed precipitation was removed by filtration. The solvent of the filtrate was removed in vacuo. The crude product was purified by flash chromatography on silica (30 g), using a mixture of dichloromethane/methanol/25% aqueous ammonia (100:10:1) as eluent, to give 800 mg of 1-[4-(2-(aminooxy)ethyl)piperidin-1-yl]hexadecan-1-one.

MS: m/z=383 [M+1$^+$]

$^1$H-NMR (CDCl$_3$): δ 0.80 (t, 3H); 1.25 (m, 2H); 1.60 (m, 26H); 1.70 (m, 4H); 1.65 (m, 3 H); 2.70 8t, 2H); 2.60 (t, 1H); 3.05 (t, 1H); 3.80 (m, 3H); 4.60 (d, 1H).

Example 6

(S)-2-Aminopent-4-ynoic acid amide

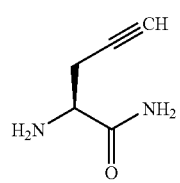

Step 1:

((S)-1-Carbamoylbut-3-ynyl)carbamic acid tert-butyl ester

At 0° C., 1-(3-dimethylaminopropyl)-3-ethylcarbodiimide hydrochloride (563 mg, 2.94 mmol) was added to a solution of commercially available (S)-2-(tert-butyoxycarbonylaminopent-4-ynoic acid (e.g. Acros, 626 mg, 2.94 mmol) and 1-hydroxybenzotriazole (397 mg, 2.94 mmol) in N,N-dimethylformamide (20 ml). The reaction mixture was stirred at 0° C. for 20 min. A 25% aqueous solution of ammonia (2.38 ml) was added. The reaction mixture was stirred for 16 h, while warming up to room temperature. It was diluted with ethyl acetate (150 ml) and washed with a 10% aqueous solution of sodium hydrogensulphate (150 ml). The aqueous phase was extracted with ethyl acetate (2×100 ml). The combined organic layers were washed with brine (250 ml) and dried over magnesium sulphate. The solvent was removed in vacuo. The residue was dissolved in ethyl acetate (100 ml) and washed with a mixture of brine (75 ml) and water (75 ml). The aqueous phase was extracted with ethyl acetate (2×50 ml). The combined organic layers were dried over magnesium sulphate. The solvent was removed in vacuo. The crude product was purified by flash chromatography on silica (50 g), using dichloromethane/methanol (10:1) as eluent, to give 138 mg of ((S)-1-carbamoylbut-3-ynyl)carbamic acid tert-butyl ester.

$^1$H-NMR (CDCl$_3$): δ 1.40 (s, 9H); 2.15 (t, 1H); 2.70 (m, 1H); 2.90 (m, 1H); 4.40 (m, 1 H); 5.70 (d, 1H); 6.50 (br, 1H); 6.90 (br, 1H).

Step 2:

Trifluoroacetic acid (3 ml) was added to a solution of ((S)-1-carbamoylbut-3-ynyl)carbamic acid tert-butyl ester (138 mg, 0.65 mmol) in dichloromethane (3 ml). The reaction mixture was stirred for 1.25 h at room temperature. The solvent was removed in vacuo. The residue was dissolved in dichloromethane (40 ml) and the solvent was removed in vacuo. The latter procedure was repeated twice to give crude trifluoroacetate salt of (S)-2-aminopent-4-ynoic acid amide, which was used for the following experiments.

MS: m/z=113 [M+1$^+$]

$^1$H-NMR (DMSO-d$_6$): δ 2.70 (m, 2H); 3.15 (t, 1H); 3.85 (m, 1H); 7.65 (s, 1H); 7.85 (s, 1 H); 8.20 (br, 3H).

Example 7

(S)-2-(([Leu$^{37}$]GLP-1-(7-37)yl)amino)pent-4-ynoic amide

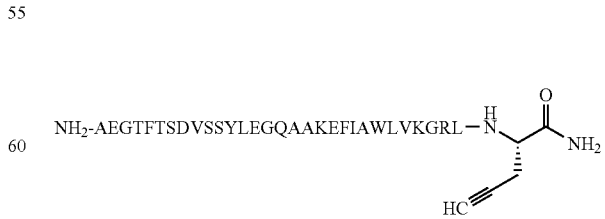

A solution of [Leu$^{37}$]GLP-1 (7-37)ylalanine (0.348 mg, 100 nmol), trifluoroacetate salt of (S)-2 -aminopent-4-ynoic acid amide (2.26 mg, 10000 nmol), and hydroxypropyl-betacyclodextrin (4 mg) in a buffer of 250 mM HEPES and 5 mM EDTA (0.085 ml), which had been adjusted to pH 7.5 prior its use, a 25% aqueous solution of ammonia and 1 N hydrochloric acid (together 0.011 ml) was prepared, having a pH of 7.96. A solution of CPY (1.0 U) in water (0.005 ml) was added. The reaction mixture was left at room temperature. After 40 min a mass corresponding to (S)-2-(([Leu$^{37}$]GLP-1-(7-37)yl)amino)pent-4-ynoic amide could be found in the MALDI-TOF besides masses corresponding to [Leu$^{37}$]GLP-1-(7-37)ylalanine, to [Leu$^{37}$]GLP-1-(7-37) peptide, and to (S)-2-{(S)-2-(([Leu$^{37}$]GLP-1-(7-37)yl)amino)pent-4-ynoylamino}pent-4-ynoyl amide.

MALDI-TOF (CHCA): m/z=3508, 3485, 3604, 3413.

Example 8

(2S)-2-Amino-3-(4-(prop-2-ynyloxy)phenyl)propionamide

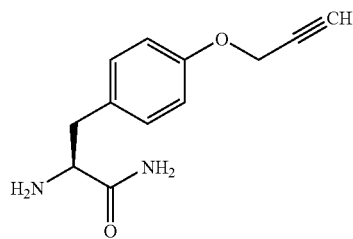

Step 1:

[(S)-1-Carbamoyl-2-(4-hydroxyphenyl)ethyl]-carbamic acid tert-butyl ester

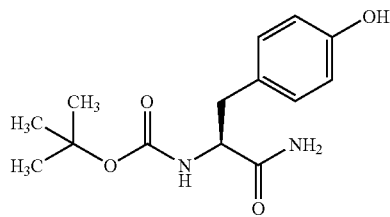

Di-tert-butyl dicarbonate (15 g, 69 mmol) was added to a solution of the hydrochloride salt of tyrosine amide (15 g, 69 mmol) in dioxane (140 ml) and a 1 N aqueous solution of sodium hydroxide (140 ml). The reaction mixture was stirred for 16 h at room temperature. It was diluted with a 10% aqueous solution of sodium hydrogensulphate (200 ml) and extracted with ethyl acetate (3×200 ml). The combined organic layers were washed with a saturated aqueous solution of sodium hydrogencarbonate (100 ml) and dried over magnesium sulphate. The solvent was removed in vacuo. The crude product was purified by flash chromatography on silica (400 g), using a mixture of dichloromethane/methanol (10:1) to give 8.17 g of [(S)-1-carbamoyl-2-(4-hydroxyphenyl)ethyl]-carbamic acid tert-butyl ester.

MS: m/z=303 (M+Na)$^+$.

$^1$H-NMR (DMSO-d$_6$): δ 1.31 (s 9H); 2.80 (dd, 1H); 2.83 (dd, 1H); 4.00 (m, 1H); 6.62 (d, 2 H); 6.70 (d, 1H); 6.97 (br, 1H); 7.03 (d, 2H); 7.31 (br, 1H); 9.14 (s, 1H).

Step 2:

[(S)-1-Carbamoyl-2-(4-(prop-2-ynyloxy)phenyl)ethyl]carbamic acid tert-butyl ester

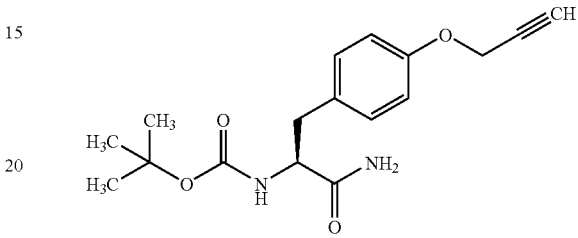

A mixture of [(S)-1-carbamoyl-2-(4-hydroxyphenyl)ethyl]-carbamic acid tert-butyl ester (1.0 g, 3.57 mmol), tetrabutylammonium iodide (65 mg, 0.17 mmol), potassium carbonate (3.94 g, 29 mmol), propargyl bromide (0.38 ml, 4.28 mmol) and N,N-dimethylformamide (15 ml) was heated to 60° C. for 16 h. It was cooled to room temperature, diluted with water (30 ml) and acidified with a 10% aqueous solution of sodium hydrogensulphate. The mixture was extracted with ethyl acetate (2×100 ml). The combined organic layers were washed with a saturated aqueous solution of sodium hydrogencarbonate (200 ml) and dried over magnesium sulphate. The solvent was removed in vacuo. The crude product was purified by flash chromatography on silica (100 g), using a mixture of dichloromethane/methanol (10:1) as eluent, to give 998 mg of [(S)-1-crbamoyl-2-(4-(prop-2-ynyloxy)phenyl)ethyl]carbamic acid tert-butyl ester.

MS: m/z=341 (M+Na)$^+$.

$^1$H-NMR (DMSO-d$_6$) δ 1.31 (s, 9H); 2.50 (s, 1H); 2.67 (dd, 1H); 2.91 (dd, 1H); 4.03 (m, 1 H); 4.74 (s, 2H); 6.77 (d, 1H); 6.86 (d, 2H); 6.99 (s, 1H), 7.17 (d, 2H); 7.35 (s, 1 H).

Trifluoroacetic acid (10 ml) was added to a solution of [(S)-1-crbamoyl-2-(4-(prop-2-ynyloxy)phenyl)ethyl]carbamic acid tert-butyl ester (998 mg, 3.13 mmol) in dichloromethane (10 ml). The reaction mixture was stirred for 1.5 h at room temperature. The solvent was removed. The residue was dissolved in dichloromethane (30 ml). The solvent was removed. The latter procedure was repeated twice to give 1.53 g of the trifluoroacetate salt of (2S)-2-amino-3-(4-(prop-2-ynyloxy)phenyl)propionamide.

HPLC (method 02-B4-4): R$_f$=5.62 min.

MS: m/z=219(M+1)$^+$.

$^1$H-NMR (CDCl$_3$) δ 2.51 (s, 1H); 3.02 (m, 2H); 3.90 (m, 1H); 4.78 (s, 2H); 6.95 (d, 2 H); 7.20 (d, 2H); 7.56 (s, 1H); 7.87 (s, 1H); 8.10 (br, 3H).

Example 9

(S)-2-([Leu37]GLP-1(7-37)ylamino)3-(4(prop-2-ynyl)phenyl)propionamide

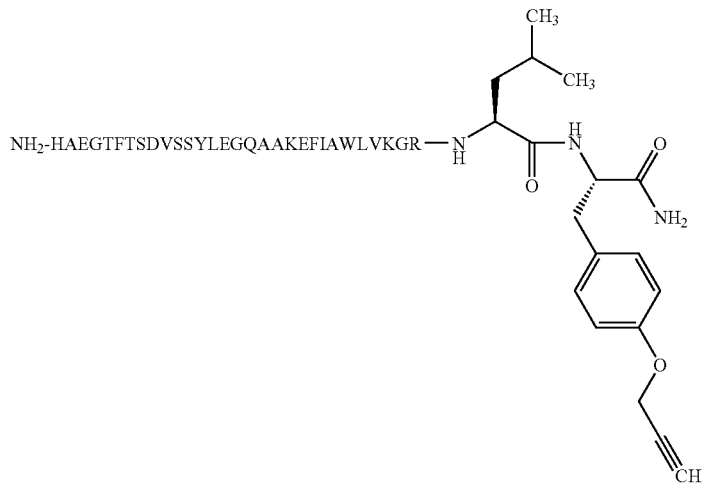

Step 1:

[Leu$^{37}$]GLP-1(7-37)ylalanine

[Leu$^{37}$]GLP-1(7-37)ylalanine was prepared on an Applied Biosystems 433A Peptide Synthesizer by standard Fmoc-strategy starting with a commercially available Fmoc-Ala-Wang resin.

Following amino acid derivatives were used:

| coupling no. | amino acid derivative |
|---|---|
| 1 | Fmoc-Leu-OH |
| 2 | Fmoc-Arg(Pmc)-OH |
| 3 | Fmoc-Gly-OH |
| 4 | Fmoc-Lys(Boc)-OH |
| 5 | Fmoc-Val-OH |
| 6 | Fmoc-Leu-OH |
| 7 | Fmoc-Trp(Boc)-OH |
| 8 | Fmoc-Ala-OH |
| 9 | Fmoc-Ile-OH |
| 10 | Fmoc-Phe-OH |
| 11 | Fmoc-Glu(OtBu)-OH |
| 12 | Fmoc-Lys(Boc)-OH |
| 13 | Fmoc-Ala-OH |
| 14 | Fmoc-Ala-OH |
| 15 | Fmoc-Gln(Trt)-OH |
| 16 | Fmoc-Gly-OH |
| 17 | Fmoc-Glu(OtBu)-OH |
| 18 | Fmoc-Leu-OH |
| 19 | Fmoc-Tyr(tBu)-OH |
| 20 | Fmoc-Ser(tBu)-OH |
| 21 | Fmoc-Ser(tBu)-OH |
| 22 | Fmoc-Val-OH |
| 23 | Fmoc-Asp(OtBu)-OH |
| 24 | Fmoc-Ser(tBu)-OH |
| 25 | Fmoc-Thr(tBu)-OH |
| 26 | Fmoc-Phe-OH |
| 27 | Fmoc-Thr(tBu)-OH |
| 28 | Fmoc-Gly-OH |
| 29 | Fmoc-Glu(OtBu)-OH |
| 30 | Fmoc-Ala-OH |
| 31 | Fmoc-His(Trt)-OH |

A mixture of trifluoroacetic acid (10 ml), water (0.265 ml) and triisopropylsilane (0.265 ml) was added to the resin. It was shaken for 1.5 h. The liquid was collected. The resin was washed with trifluoroacetic acid (1 ml). The liquids were combined. The solution was concentrated under a stream of nitrogen. Ether (40 ml) was added. The precipitation was isolated by centrifugation. The crude product was purified on a reversed phase C$_{18}$-column on a HPLC, using a gradient of 37-65% acetonitrile in water in a buffer of 0.1% trifluoroacetic acid, as eluent.

Step 2:

CPY-Reaction of (2S)-2-Amino-3-(4-(prop-2-ynyloxy)phenyl)propionamide with [Leu$^{37}$]GLP-1(7-37)alanine A mixture (0.100 ml final volume) of [Leu$^{37}$]GLP-1(7-37) ylalanine (1 mM final concentration) and the trifluoroacetate salt of (2S)-2-amino-3-(4-(prop-2-ynyloxy)phenyl)propionamide (100 mM final concentration) and hydroxypropyl-beta-cyclodextrin (4 mg) in a buffer, consisting of 250 mM HEPES and 5 mM EDTA, was adjusted to pH 8, using a 1 N aqueous solution of sodium hydroxide. A solution of carboxypeptidase Y (CPY, 200 U/ml, 0.005 ml, 1 U) was added to obtain the desired final volume and concentrations. The mixture was left for 3 h at room temperature.

MALDI-TOF (Matrix assisted laser desorption/ionization time of flight mass spectroscopy): m/z=3612 ((S)-2-([Leu37] GLP-1(7-37)ylamino)3-(4-(prop-2-ynyl)phenyl)propionamide) along with 3412 ([Leu$^{37}$]GLP-1 peptide).

MS (electrospray): 1205 (M)$^{3+}$.

Example 10

(2S)-2-([Glu³, Leu¹⁰]GLP-2ylleucinylamino)-3-(4-(prop-2-ynyloxy)phenyl)propionamide

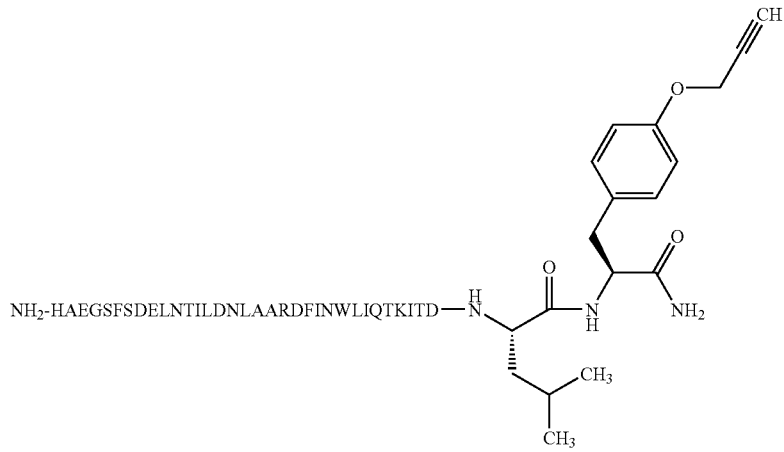

Step 1:

[Glu³, Leu¹⁰]GLP-2ylleuccinylalanine

[Glu³, Leu¹⁰]GLP-2ylleuccinylalanine was prepared on an Applied Biosystems 433A Peptide Synthesizer by standard Fmoc-strategy starting with a commercially available Fmoc-Ala-Wang resin. Following amino acid derivatives were used:

| coupling no. | amino acid derivative |
| --- | --- |
| 1 | Fmoc-Leu-OH |
| 2 | Fmoc-Asp(OtBu)-OH |
| 3 | Fmoc-Thr(tBu)-OH |
| 4 | Fmoc-Ile-OH |
| 5 | Fmoc-Lys(Boc)-OH |
| 6 | Fmoc-Thr(tBu)-OH |
| 7 | Fmoc-Gln(Trt)-OH |
| 8 | Fmoc-Ile-OH |
| 9 | Fmoc-Leu-OH |
| 10 | Fmoc-Trp(Boc)-OH |
| 11 | Fmoc-Asn(Trt)-OH |
| 12 | Fmoc-Ile-OH |
| 13 | Fmoc-Phe-OH |
| 14 | Fmoc-Asp(OtBu)-OH |
| 15 | Fmoc-Arg(Pmc)-OH |
| 16 | Fmoc-Ala-OH |
| 17 | Fmoc-Ala-OH |
| 18 | Fmoc-Leu-OH |
| 19 | Fmoc-Asn(Trt)-OH |
| 20 | Fmoc-Asp(OtBu)-OH |
| 21 | Fmoc-Leu-OH |
| 22 | Fmoc-Ile-OH |
| 23 | Fmoc-Thr(tBu)-OH |
| 24 | Fmoc-Asn(Trt)-OH |
| 25 | Fmoc-Leu-OH |
| 26 | Fmoc-Glu(OtBu)-OH |
| 27 | Fmoc-Asp(OtBu)-OH |
| 28 | Fmoc-Ser(tBu)-OH |
| 29 | Fmoc-Phe-OH |
| 30 | Fmoc-Ser(tBu)-OH |
| 31 | Fmoc-Gly-OH |
| 32 | Fmoc-Glu(OtBu)-OH |
| 33 | Fmoc-Ala-OH |
| 34 | Fmoc-His(Trt)-OH |

A mixture of trifluoroacetic acid (10 ml), water (0.265 ml) and triisopropylsilane (0.265 ml) was added to the resin. It was shaken for 1.5 h. The liquid was collected. The resin was washed with trifluoroacetic acid (1 ml). The liquids were combined. The solution was concentrated under a stream of nitrogen. Ether (40 ml) was added. The precipitation was isolated by centrifugation. The crude product was purified on a reversed phase $C_{18}$-column on a HPLC, using a gradient of 37-65% acetonitrile in water in a buffer of 0.1% trifluoroacetic acid, as eluent.

HPLC: 8.81 min (method 02-B4-4).

MALDI-TOF: m/z=3946

MS: m/z=1317. 988, 790.

Step 2:

CPY-Reaction of (2S)-2-Amino-3-(4-(prop-2-ynyloxy)phenyl)propionamide with ((([Glu³, Leu¹⁰]GLP-2yl)leucinyl)alanine A mixture (1.5 ml final volume) of ((([Glu³, Leu¹⁰]GLP-2yl)leucinyl)alanine (1 mM final concentration) and the trifluoroacetate salt of (2S)-2-amino-3-(4-(prop-2-ynyloxy)phenyl)propionamide (6 mg, 150 mM final concentration) and hydroxypropyl-beta-cyclodextrin (61 mg) in a buffer, consisting of 250 mM HEPES and 5 mM EDTA, was adjusted to pH 8, using a 1 N aqueous solution of sodium hydroxide. A solution of carboxypeptidase Y (CPY, 800 U/ml, 0.019 ml, 15 U) was added to obtain the desired final volume and concentrations. The mixture was left for 3.5 h at room temperature. The mixture was diluted with water to a volume of 10 ml. The product was isolated by HPLC-purification, using a $C_{18}$-column and a gradient of 39-67% acetonitrile in water, which was acidified with 0.1% trifluoroacetic acid, to give (2S)-2-([Glu³, Leu¹⁰]GLP-2ylleucinylamino)-3-(4-(prop-2-ynyloxy)phenyl)propionamide. Using an absorption coefficient of 1500000 at 214 nm, a yield of 2.5 mg was determined.

MALDI-TOF: 4073.

HPLC (system 02-b4-4): 9.14 min.

MS (electrospray): m/z=815, 1120, 1359.

Example 11

(S)-3-(4((3-(3-Chlorophenyl)isoxazol-5-yl)methoxy)phenyl)-2-([Glu³, Leu¹⁰]GLP-2ylleucinylamino) propionic amide

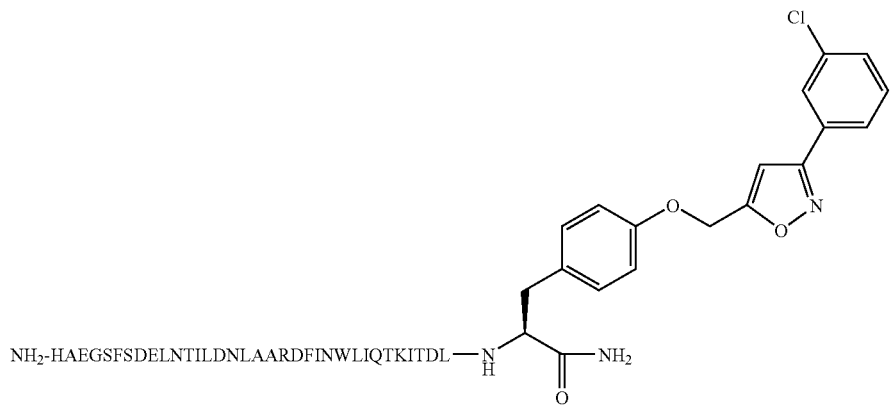

Step 1:

3-Chlorobenzaldehyde oxime

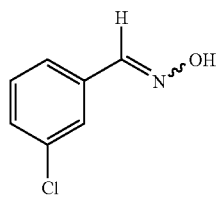

A solution of hydroxylamine hydrochloride (3.68 g, 53 mmol) in water (5 ml) was added to a solution of 3-chlorobenzaldehyde (5.00 ml, 44 mmol) in ethanol (20 ml). A solution of sodium hydroxide (2.64 g, 66 mmol) in water (5 ml) was added. The reaction mixture was stirred at room temperature for 48 h. The reaction mixture was given onto water/ice (150 ml). The formed precipitation was isolated by filtration and dissolved in dichloromethane (200 ml). This solution was dried over magnesium sulphate. The solvent was removed to give 3.88 g of 3-chlorobenzaldehyde oxime, which was used without further purification.

Step 2:

A 10% solution of sodium hypochlorite (0.008 ml) was added to a suspension of 3-chlorobenzaldehyde oxime (4.2 mg, 0.027 mmol) in water (0.5 ml). The solution was left for 10 min at room temperature. A solution of (2S)-2-([Glu³, Leu¹⁰]GLP-2ylleucinylamino)-3-(4-(prop-2ynyloxy)phenyl)propionamide (1.1 mg, 0.00027 mmol) and triethylamine (0.003 ml) in water (0.5 ml) was added. The reaction mixture was left at room temperature for 16 h. The crude product was purified on a reversed phase $C_{18}$—HPLC, using a gradient of 43-75% acetonitrile in water in a 0.1% buffer of TFA.

HPLC (method 02-b4-4): 9.56 min.

MS (EI): m/z=1410 ($M^{3+}$), 1054 ($M^{4+}$) and 844 ($M^{5+}$)

Example 12

(S)-2-Amino-3-[4-(2-oxopropoxy)phenyl]propionamide

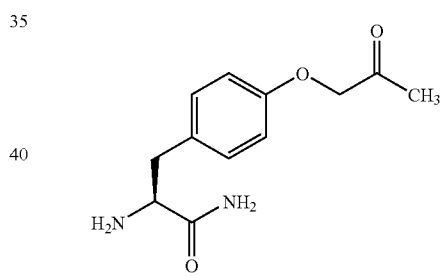

Step 1:

[(S)-1-Carbamoyl-2-(4-hydroxyphenyl)ethyl]-carbamic acid tert-butyl ester

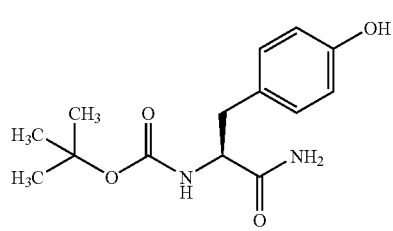

1-(3-Dimethylaminopropyl)-3-ethylcarbodiimide hydrochloride (6.82 g, 35.5 mmol) was added to a solution of BOC-protected tyrosine (10.0 g, 35,5 mmol) and 1-hydroxy-benzotriazole (5.44 g, 35.5 mmol) in a mixture of N,N-dimethylformamide (10 ml) and dihchloromethane (10 ml). The reaction mixture was stirred for 20 min. A 25% aqueous solution of ammonia in water was added. The reaction mixture was stirred at room temperature for 16 h. It was diluted with ethyl acetate (100 ml) and washed with water (3×100 ml) and subsequently with a saturated aqueous solution of sodium hydrogencarbonate (100 ml). It was dried over magnesium sulphate. The solvent was removed in vacuo to give 4.24 g of [(S)-1-carbamoyl-2-(4-hydroxyphenyl)ethyl]-carbamic acid tert-butyl ester.

$^1$H-NMR (DMSO-$d_6$): δ 1.31 (s 9H); 2.80 (dd, 1H); 2.83 (dd, 1H); 4.00 (m, 1H); 6.62 (d, 2H); 6.70 (d, 1H); 6.97 (br, 1H); 7.03 (d, 2H); 7.31 (br, 1H); 9.14 (s, 1H).

Step 2:

{(S)-1-Carbamoyl-2-[4-(2-oxopropoxy)phenyl]ethyl}carbamic acid tert-butyl ester

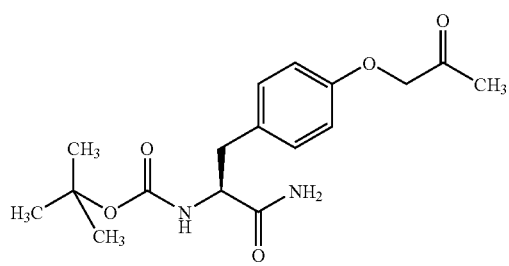

To a mixture of [(S)-1-carbamoyl-2-(4-hydroxyphenyl)ethyl]-carbamic acid tert-butyl ester (3.00 g, 10.7 mmol) and potassium carbonate (7.40 g, 53.5 mmol) in N,N-dimethylformamide (50 ml) were added subsequently chloroacetone (1.02 ml, 12.8 mmol) and tetrabutylammonium iodide (197 mg, 0.54 mmol). The reaction mixture was heated to 90° C. for 16 h and cooled to room temperature. It was diluted with water (100 ml) and acidified with a 10% solution of sodium hydrogensulphate to pH 2. Ethyl acetate (300 ml) was added. The phases were separated. The organic layer was washed with water (3×150 ml) and dried over magnesium sulphate. The solvent was removed in vacuo to give 2.65 g of {(S)-1-carbamoyl-2-[4-(2-oxopropoxy)phenyl]ethyl}carbamic acid tert-butyl ester.

MS: m/z=359 (M+Na$^+$)

$^1$H-NMR (DMSO-$d_6$) δ 1.30 (s, 9H); 2.10 (s, 3H); 2.70 (dd, 1H); 2.90 (dd, 1H); 3.95 (br, 1H); 4.00 (m, 1H); 4.75 (s, 2H); 6.80 (d, 2H); 7.00 (br, 1H); 7.20 (d, 2H); 7.35 (br, 1 H).

Step 3:

Trifluoroacetic acid (50 ml) was added to a solution of {(S)-1-carbamoyl-2-[4-(2-oxopropoxy)phenyl]ethyl}carbamic acid tert-butyl ester (2.65 g, 7.88 mmol) in dichloromethane (50 ml). The reaction mixture was stirred for 1 h at room temperature. The solvent was removed in vacuo. The residue was dissolved in dichloromethane (50 ml) and the solvent was removed in vacuo. The latter procedure was repeated once. The crude product was purified by C-18 reversed phase chromatography on a HPLC, using a gradient of 13-33% acetonitrile in water in a buffer of trifluoroacetic acid (0.1%) to give 460 mg of (S)-2-amino-3-[4-(2-oxopropoxy)phenyl]propionamide.

MS: m/z=237 (M$^+$)

$^1$H-NMR (DMSO-$d_6$, TFA-salt) δ 2.20 (s, 3H); 2.80-3.10 (m, 2H); 3.90 (m, 1H); 4.80 (s, 2H); 6.90 (d, 2H); 7.20 (d, 2H); 7.55 (br, 1H); 7.90 (br, 1H); 8.10+(br, 3 H).

Example 13

(S)-2-([Glu$^3$, Leu$^{10}$]GLP-2ylleucinylamino)-3-(4-(2-oxopropoxy)phenyl)propionic amide

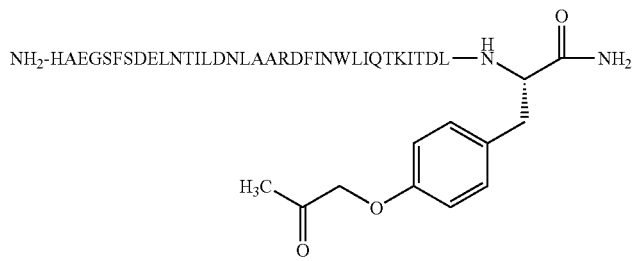

A solution of ((([Glu$^3$, Leu$^{10}$]GLP-2yl)leucinyl)alanine (0.50 mg, 127 pmol) in water (0.040 ml) and an 1 N aqueous solution of sodium hydroxide (0.003 ml) was added to a solution of the trifluoroacetate salt of (S)-2-amino-3-[4-(2-oxopropoxy)phenyl]propionamide (13.3 mg, 0.038 mmol) in an aqueous buffer containing 250 mM HEPES and 5 mM EDTA, which had been adjusted to pH 8 with sodium hydroxide. The solution was adjusted to pH 8 with a 1 N aqueous solution of sodium hydroxide. The solution was diluted to a final volume of 0.127 ml with an aqueous buffer containing 250 mM HEPES and 5 mM EDTA, which had been adjusted to pH 8 with sodium hydroxide. A solution of CPY in water (0.005 ml, 1 U) was added. The reaction mixture was left at room temperature for 16 h. The MS analysis showed the formation of the product with the desired mass.

MALDI-TOF: m/z=4090.321
MS: m/z=1365, 1024
HPLC (Method 03-b6-1): 30.69 min.

Example 14

(2S)-2-([Glu³]GLP-2ylleucinylamino)-3-(4-(prop-2-ynyloxy)phenyl)propionamide

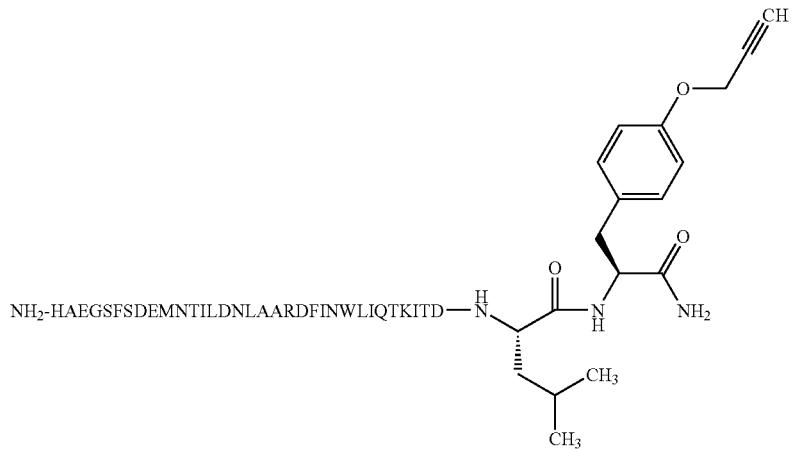

Step 1:

(([Glu³]GLP-2yl)leucinyl)alanine (([Glu³]GLP-2yl)leucinyl)alanine was prepared as described for (([Glu³, Leu¹⁰]GLP-2yl)leucinyl)alanine from commercially available Fmoc-Ala-Wang resin. Following amino acid derivatives were used:

| coupling no. | amino acid derivative |
|---|---|
| 1 | Fmoc-Leu-OH |
| 2 | Fmoc-Asp(OtBu)-OH |
| 3 | Fmoc-Thr(tBu)-OH |
| 4 | Fmoc-Ile-OH |
| 5 | Fmoc-Lys(Boc)-OH |
| 6 | Fmoc-Thr(tBu)-OH |
| 7 | Fmoc-Gln(Trt)-OH |
| 8 | Fmoc-Ile-OH |
| 9 | Fmoc-Leu-OH |
| 10 | Fmoc-Trp(Boc)-OH |
| 11 | Fmoc-Asn(Trt)-OH |
| 12 | Fmoc-Ile-OH |
| 13 | Fmoc-Phe-OH |
| 14 | Fmoc-Asp(OtBu)-OH |
| 15 | Fmoc-Arg(Pmc)-OH |
| 16 | Fmoc-Ala-OH |
| 17 | Fmoc-Ala-OH |
| 18 | Fmoc-Leu-OH |
| 19 | Fmoc-Asn(Trt)-OH |
| 20 | Fmoc-Asp(OtBu)-OH |
| 21 | Fmoc-Leu-OH |
| 22 | Fmoc-Ile-OH |
| 23 | Fmoc-Thr(tBu)-OH |
| 24 | Fmoc-Asn(Trt)-OH |
| 25 | Fmoc-Met-OH |
| 26 | Fmoc-Glu(OtBu)-OH |
| 27 | Fmoc-Asp(OtBu)-OH |
| 28 | Fmoc-Ser(tBu)-OH |
| 29 | Fmoc-Phe-OH |
| 30 | Fmoc-Ser(tBu)-OH |
| 31 | Fmoc-Gly-OH |
| 32 | Fmoc-Glu(OtBu)-OH |
| 33 | Fmoc-Ala-OH |
| 34 | Fmoc-His(Trt)-OH |

HPLC: 8.60 min (method 02-B4-4).

MALDI-TOF: m/z=3964.17.

Step 2:

CPY-Reaction of (2S)-2-Amino-3-(4-(prop-2-ynyloxy)phenyl)propionamide with (([Glu³]GLP-2yl)leucinyl)alanine:

(([Glu³]GLP-2yl)leucinyl)alanine was prepared by standard solid phase peptide synthesis on an ABI-433A Peptide Synthesizer using a FMOC-strategy, known to a person skilled in the art. A mixture (7 ml final volume) of (([Glu³]GLP-2yl)leucinyl)alanine (1 mM final concentration) and the trifluoroacetate salt of (2S)-2-amino-3-(4-(prop-2-ynyloxy)phenyl)propionamide (28 mg, 150 mM final concentration) and hydroxypropyl-beta-cyclodextrin (284 mg) in a buffer, consisting of 250 mM HEPES and 5 mM EDTA, was adjusted to pH 8, using a 1 N aqueous solution of sodium hydroxide. A solution of carboxypeptidase Y (CPY, 800 U/ml, 0.088 ml, 70 U) was added to obtain the desired final volume and concentrations. The mixture was left for 100 min at room temperature. The mixture was diluted with water to a volume of 10 ml. The product was isolated by HPLC-purification, using a $C_{18}$-column and a gradient of 36-75% acetonitrile in water, which was acidified with 0.1% trifluoroacetic acid, to give (2S)-2-([Glu³]GLP-2ylleucinylamino)-3-(4-(prop-2-ynyloxy)phenyl)propionamide. Using an absorption coefficient of 1500000 at 214 nm, a yield of 9.9 mg was determined.

MALDI-TOF: 4096 ($M^+$)

HPLC (system 02-b4-4): 8.97 min

MS (electrospray): m/z=1366 ($M^{3+}$), 1024 ($M^{4+}$), and 819 ($M^{5+}$).

Example 15

(S)-3-(4-((3-(3-Chlorophenyl)isoxazol-5-yl)methoxy)phenyl)-2-([Glu³]GLP-2ylleucinylamino)propionic amide

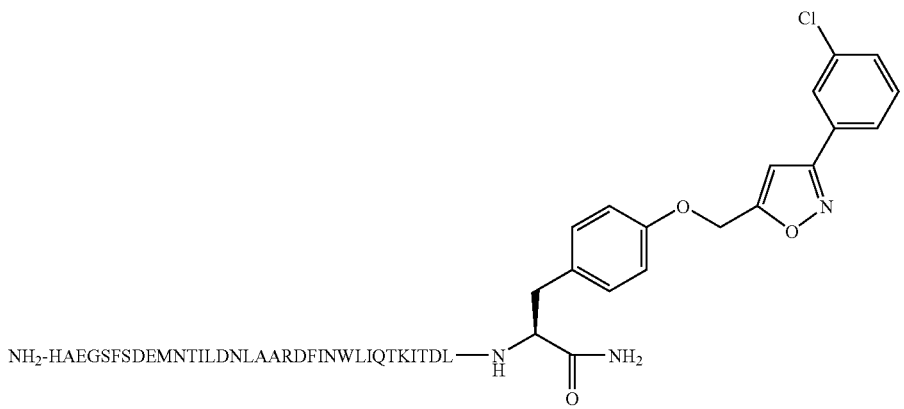

A 10% solution of sodium hypochlorite (0.062 ml) was added to a suspension of 3-chlorobenzaldehyde oxime (32 mg, 0.205 mmol) in water (4.2 ml). The mixture was left for 10 min at room temperature and added to a solution of (2S)-2-([Glu³]GLP-2ylleucinylamino)-3-(4-(prop-2-ynyloxy)phenyl)propionamide (8.4 mg, 0.0021 mmol) and triethylamine (0.025 ml) in water (4.7 ml). The reaction mixture was left at room temperature for 16 h. The crude product was purified on a reversed phase $C_{18}$-HPLC, using a gradient of 40-80% acetonitrile in water in a 0.1% buffer of TFA. Using an absorption coefficient of 1500000 at 214 nm, a yield of 0.132 mg was determined.

MALDI-TOF: 4244 (M⁺) and 4228 (M-O⁺)
HPLC (method 02-b4-4): 9.41 min.
MS (EI): m/z=1417 (M³⁺) and 1062 (M⁴⁺).

Example 16

3-(3-(3-((4((S)-2-Carbamoyl-3-([Glu³, Leu¹⁰]GLP-2ylleucinylamino)ethyl)phenoxyl)methyl)-isoxazol-3-yl)benzylcarbamoyl)propionic acid Step 1:

(3-Hydroxymethylbenzyl)carbamic acid tert butylester

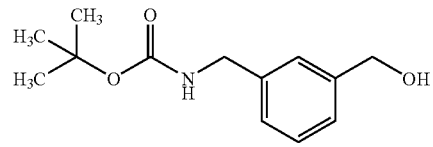

At 0° C., ethyl chloroformate (1.93 ml, 20 mmol) was added to a solution of 3-(tert-butoxycarbonylaminomethyl)benzoic acid (5.0 g, 20 mmol) and triethylamine (3.33 ml, 24 mmol) in tetrahydrofuran (30 ml). The reaction mixture was stirred for 40 min at 0° C., and the formed precipitation was filtered off. The filtrate was cooled to 0° C. A 2.0 M solution of lithium borohydride in THF (25 ml, 50 mmol) was added.

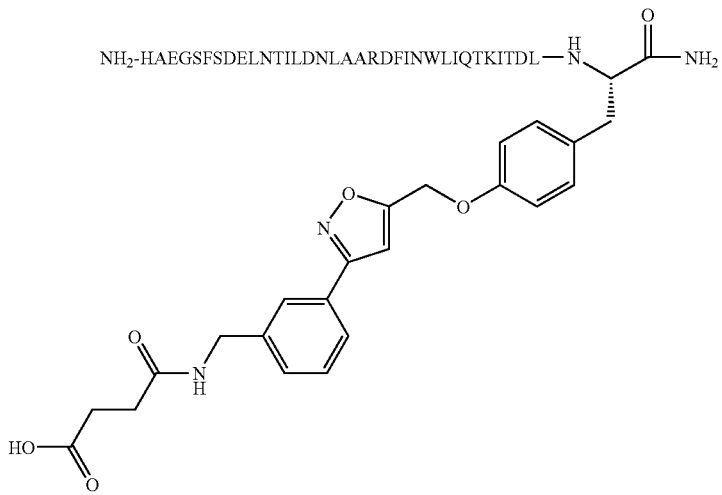

The reaction mixture was stirred for 16 h, while warming up to room temperature. Water was added carefully, until no gas was formed. A 10% solution of sodium hydrogensulphate (10 ml) was added. A saturated solution of sodium hydrogen carbonate (200 ml) was added. The mixture was extracted with ethyl acetate (200 and 100 ml). The combined organic layers were dried over magnesium sulphate. The solvent was removed in vacuo. The crude product was purified by flash chromatography on silica (80 g), using ethyl acetate/heptane 1:1 as eluent, to give 3.73 g of (3-hydroxymethylbenzyl) carbamic acid tert butylester.

MS: m/z=260 (M+23$^+$)

$^1$H-NMR (CDCl$_3$): δ 1.48 (s, 9H); 4.30 (br, 2H); 4.70 (s, 2H); 4.85 (br, 1H); 7.15-7.35 (m, 5 H).

Step 2:

(3-(Aminomethyl)phenyl)methanol

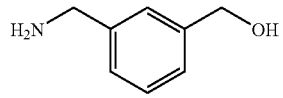

Trifluoroacetic acid (5 ml) was added to a solution of (3-hydroxymethylbenzyl)carbamic acid tert butylester (1.70 g, 7.17 mmol) in dichloromethane (5 ml). The reaction mixture was stirred for 40 min. The solvent was removed in vacuo. The residue was dissolved in dichloromethane (40 ml). The solvent was removed in vacuo. The latter procedure was repeated twice. The residue was dissolved in water (50 ml) and an 1 N aqueous solution of sodium hydroxide (100 ml). It was washed with tert-butyl methyl ether (3×100 ml). It was saturated with sodium chloride and extracted with dichloromethane (3×75 ml). The combined dichloromethane-phases were dried over magnesium sulphate. The solvent was removed in vacuo to give 328 mg of crude (3-(aminomethyl)phenyl)methanol, which was used for the further steps without purification.

$^1$H-NMR (DMSO-d$_6$): δ 3.30 (br, 2H); 3.70 (s, 2H); 4.45 (s, 2H); 5.15 (br, 1H); 7.10-7.30 (m, 4 H).

Step 3:

N-(3-(Hydroxymethyl)benzyl)succinamic acid tert-butyl ester

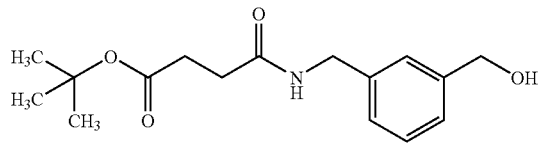

At 0° C., 1-(3-dimethylaminopropyl)-3-ethylcarbodiimide hydrochloride (451 mg, 2.35 mmol) was added to a solution of mono-tert-butyl succinate (410 mg, 2.35 mmol) and 3,4-dihydro-3-hydroxy-4-oxo-1,2,3-benzotriazin (384 mg, 2.35 mmol) in a mixture of N,N-dimethylformamide (5 ml) and dichloromethane (5 ml). The reaction mixture was stirred for 25 min at 0° C. A solution of crude (3-(aminomethyl)phenyl) methanol (340 mg, 2.48 mmol) in N,N-dimethylformamide (5 ml) and ethyldiisopropylamine(0.40 ml, 2.48 mmol) were added successively. The reaction mixture was stirred for 16 h, while it was slowly warming up to room temperature. It was diluted with ethyl acetate (150 ml) and washed with a 10% aqueous solution of sodium hydrogensulphate (100 ml). The aqueous phase was extracted with ethyl acetate (50 ml). The combined organic layers were washed with a saturated aqueous solution of sodium hydrogencarbonate (150 ml) and dried over magnesium sulphate. The solvent was removed in vacuo. The crude product was purified by flash chromatograpy on silica (60 g), using a mixture of ethyl acetate and heptane (2:1) as eluent to give 372 mg of N-(3-(hydroxymethyl)benzyl) succinamic acid tert-butyl ester.

MS: m/z=316 (M+23$^+$)

$^1$H-NMR (CDCl$_3$): δ 1.45 (s, 9H); 2.45 (t, 2H); 2.60 (t, 2H); 4.45 (d, 2H); (d, 2 H); 4.70 (s, 2 H); 6.15 (br, 1H); 7.15-7.35 (m, 5H).

Step 4:

N-(3-Formylbenzyl)succinamic acid tert-butyl ester

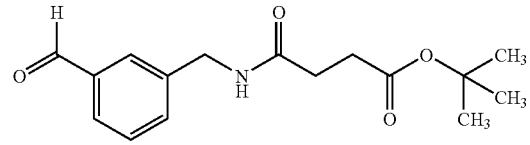

At −78° C., oxalyl chloride (0.142 ml, 1.63 mmol) was added dropwise to a solution of dimethyl sulphoxide (0.232 ml. 3.26 mmol) in dichloromethane (5 ml). The reaction mixture was stirred for 10 min at −78° C. A solution of N-(3-(hydroxymethyl)benzyl)succinamic acid tert-butyl ester (372 mg, 1.55 mmol) in dichloromethane (5 ml) was added. The reaction mixture was stirred at −78° C. for 10 min. Triethylamine (1.08 ml, 7.77 mmol) was added. The reaction mixture was stirred at −78° C. for 5 min and then warmed to room temperature. It was stirred at room temperature for 40 min and diluted with ethyl acetate (100 ml). It was washed with a 10% aqueous solution of sodium hydrogensulphate (100 ml). The aqueous phase was extracted with ethyl acetate (2×50 ml). The combined organic layers were washed with a saturated aqueous solution of sodium hydrogencarbonate (150 ml) and dried over magnesium sulphate. The solvent was removed to give 312 mg of crude N-(3-formylbenzyl)succinamic acid tert-butyl ester, which was used for the next step without further purification.

MS: m/z=314 (M+23$^+$)

$^1$H-NMR (CDCl$_3$): δ 1.35 (s, 9H); 2.45 (t, 2H); 2.55 (t, 2H); 4.45 (d, 2H); (d, 2 H); 6.20 (br, 1 H); 7.44 (t, 1H); 7.50 (d, 1H); 7.75 (m, 2H); 9.95 (s, 1H).

Step 5:

N-[3-((Hydroxyimino)methyl)benzyl]succinamic acid tert-butyl ester

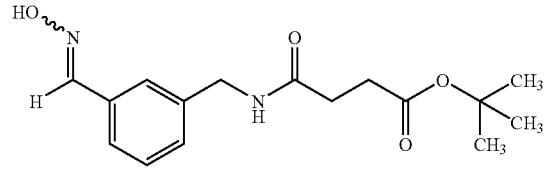

A 3.2 M aqueous solution of sodium hydroxide (0.5 ml, 1.60 mmol) was added to a solution of N-(3-formylbenzyl) succinamic acid tert-butyl ester (312 mg, 1.07 mmol) and hydroxylamine hydrochloride (89 mg, 1.29 mmol) in ethanol (2.5 ml) and water (0.5 ml). The reaction mixture was stirred at room temperature for 3 days. A 10% aqueous solution of sodium hydrogensulphate (20 ml) and water (50 ml) were added. The mixture was extracted with ethyl acetate (3×50 ml). The combined organic layers were dried over magnesium sulphate. The solvent was removed in vacuo to give 249 mg of crude N-[3-((hydroxyimino)methyl)benzyl]succinamic acid tert-butyl ester, which was used without further purification in the next step.

MS: m/z=329 (M+23⁺), 307 (M+1⁺)

¹H-NMR (DMSO-d₆): δ 1.35 (s, 9H); 2.40 (m, 4H); 4.30 (d, 2H); 7.25 (d, 1H); 7.35 (t, 1 H); 7.50 (m, 2H); 8.10 (s, 1H); 8.40 (t, 1H); 11.20 (s, 1H).

Step 6:

N-[3-(Hydroxyiminomethyl)benzyl]succinamic acid

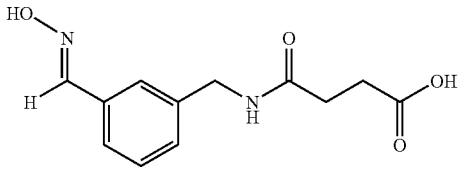

Trifluoroacetic acid (7 ml) was added to a solution of crude N-[3-((hydroxyimino)methyl)benzyl]succinamic acid tert-butyl ester (249 mg, 0.81 mmol) in dichloromethane (7 ml). The reaction mixture was stirred for 55 min at room temperature. The solvent was removed in vacuo. The residue was redissolved in dichloromethane (50 ml). The solvent was removed in vacuo. The latter procedure was repeated twice to give 294 mg of crude N-[3-(hydroxyiminomethyl)benzyl] succinamic acid, which was used in the next step without further purification.

MS: m/z=273 (M+23⁺), 251 (M+1⁺)

¹H-NMR (DMSO-d₆): δ 2.45 (A₂B₂, 4H); 4.30 (d, 2H); 7.20-7.50 (m, 4H); 8.10 (s, 1 H); 8.40 (t, 1H); 11.20 (br, 1H).

Step 7:

A 10% aqueous solution of sodium hypochlorite (0.0015 ml, 2600 pmol) was added to a solution of crude N-[3-(hydroxyiminomethyl)benzyl]succinamic acid (1.29 mg, 5150 pmol) in a mixture of water (0.11 ml) and a saturated aqueous solution of sodium hydrogencarbonate (0.01 ml). The reaction mixture was left for 10 min at room temperature. A solution of (2S)-2-([Glu³, Leu¹⁰]GLP-2ylleucinylamino)-3-(4-(prop-2ynyloxy)phenyl)propionamide (0.210 mg, 51 pmol) and triethylamine (0.0006 ml) in water (0.11 ml) was added. The reaction mixture was shaken at room temperature. After 1 h, the MALDI-TOF showed small amounts of m/z=4323, corresponding to the mass of 3-(3-(3-((4-((S)-2-carbamoyl-3-([Glu³, Leu¹⁰]GLP-2ylleucinylamino)ethyl)phenoxyl)methyl)isoxazol-3-yl)benzylcarbamoyl)propionic acid, along with major amounts of m/z=4076, corresponding to the mass of (2S)-2-([Glu³, Leu¹⁰]GLP-2ylleucinylamino)-3-(4-(prop-2ynyloxy)phenyl)propionamide. After 2 h, the LC-MS electrospray showed masses of m/z=1442, 1082, and 866, corresponding to (M³⁺), (M⁴⁺) and (M⁵⁺) respectively of 3-(3-(3-((4-((S)-2-carbamoyl-3-([Glu³, Leu¹⁰]GLP-2ylleucinylamino)ethyl)phenoxyl)methyl)isoxazol-3-yl) benzylcarbamoyl)propionic acid along with masses of m/z=1359, 1020, and 816, corresponding to (M³⁺), (M⁴⁺) and (M⁵⁺) respectively of (2S)-2-([Glu³, Leu¹⁰]GLP-2ylleucinylamino)-3-(4-(prop-2ynyloxy)phenyl)propionamide. After 8 h, the LC-MS electrospray showed small amounts of masses of m/z=1442 and 1082, corresponding to (M³⁺) and (M⁴⁺) respectively of 3-(3-(3-((4-((S)-2-carbamoyl-3-([Glu³, Leu¹⁰]GLP-2ylleucinylamino)ethyl)phenoxyl)methyl)isoxazol-3-yl)benzylcarbamoyl)propionic acid along with major amounts of masses of m/z=1360 and 1020, corresponding to (M³⁺) and (M⁴⁺) respectively of (2S)-2-([Glu³, Leu¹⁰]GLP-2ylleucinylamino)-3-(4-(prop-2ynyloxy)phenyl)propionamide.

Example 17

11-(4(4((2S)-2-Carbamoyl-2-(([Glu³, Leu¹⁰]GLP-2ylleucinylamino)ethyl)pheoxymethyl)-1,2,3-triazolyl)undecanoic acid and 11-(5-(4-((2S)-2-Carbamoyl-2-(([Glu³, Leu¹⁰]GLP-2ylleucinylamino)ethyl)pheoxymethyl)-1,2,3-triazolyl)undecanoic acid

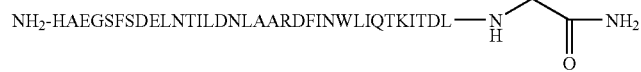

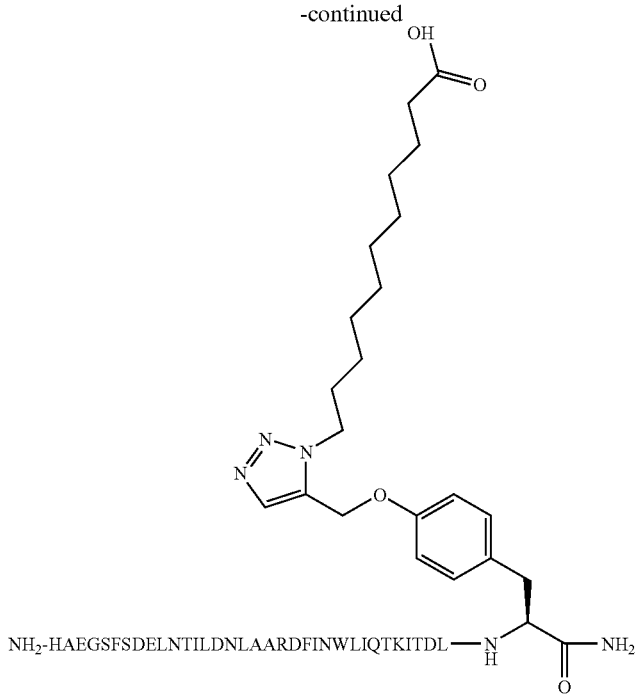

Step 1:

Methyl 11-azidoundecanoate

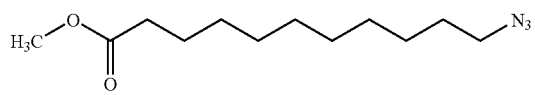

Sodium azide (4.66 g, 72 mmol) and tetrabutylammonium iodide (66 mg, 0.18 mmol) were successively added to a solution of methyl 11-bromoundecanoate (commercially available at Aldrich, 5.00 g, 17.9 mmol) in N,N-dimethylformamide (50 ml). The reaction mixture was heated to 60° C. for 16 h and cooled to room temperature. It was diluted with water (200 ml) and extracted with ethyl acetate (200 ml). The aqueous phase was washed with water (2×200 ml). The organic phase was dried over sodium sulphate. The solvent was removed in vacuo to give 4.28 g of methyl 11-azidoundecanoate.

MS: m/z=264 (M+23$^+$), 214 (M−N$_2^+$)

Step 2:

11-Azidoundecanoic acid

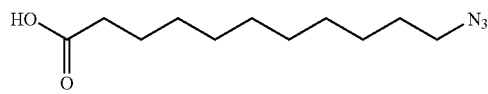

Crunched sodium hydroxide (709 mg, 17.7 mmol) was added to a solution of methyl 11-azidoundecanoate (4.03 g, 17.7 mmol) in methanol (75 ml). The reaction mixture was stirred for 16 h at room temperature. Water (50 ml) was added. The mixture was acidified to pH 2 by addition of a 10% aqueous solution of sodium hydrogensulphate and was extracted with ethyl acetate (3×50 ml). The combined organic layers were dried over sodium sulphate. The solvent was removed in vacuo. The residue was dissolved in methanol (50 ml). Crunched sodium hydroxide (1.42 g, 35.4 mmol) was added. The reaction mixture was stirred at room temperature for 16 h. Water (50 ml) was added. The mixture was acidified to pH 2 by addition of a 10% aqueous solution of sodium hydrogensulphate and was extracted with ethyl acetate (3×50 ml). The combined organic layers were dried over sodium sulphate. The solvent was removed in vacuo to give 3.13 g of 11-azidoundecanoic acid.

MS: m/z=250 (M+23$^+$), 200 (M−N$_2^+$).

$^1$H-NMR (CDCl$_3$): δ 1.30 (m, 12H); 1.65 (m, 4H); 2.40 (t, 2H); 3.20 (t, 2H); 9.00-10.80 (br, 1 H).

Step 3:

A solution of 11-azidoundecanoic acid (0.116 mg, 510 nmol) in acetonitrile (0.055 ml) was added to a solution of (2S)-2-([Glu$^3$, Leu$^{10}$]GLP-2ylleucinylamino)-3-(4-(prop-2ynyloxy)phenyl)propionamide (0.210 mg, 51 nmol) and 2,6-lutidine (0.0012 ml, 10200 nmol) in water (0.105 ml). A solution of copper(I) iodide (0.001 mg, 5 nmol) in acetonitrile (0.050 ml) was added. The reaction mixture was kept at room temeperature. After 4 h, a solution of copper(I) iodide (0.098 mg, 500 nmol) in acetonitrile was added. The reaction mixture was kept at room temperature for 16 h. A 2.5% solution of ammonia in water (0.200 ml) was added. The reaction mixture was kept at room temperature and room atmosphere for 4 h. The masses found by MS and MALDI-TOF were in correspondence with the expectations for the mass found for 11-(4-(4-((2S)-2-Carbamoyl-2-(([Glu$^3$, Leu$^{10}$]GLP-2ylleucinylamino)ethyl)pheoxymethyl)-1,2,3-triazolyl)undecanoic acid and 11-(5-(4-((2S)-2-Carbamoyl-2-(([Glu$^3$, Leu$^{10}$]GLP-2ylleucinylamino)ethyl)pheoxymethyl)-1,2,3-triazolyl)undecanoic acid.

HPLC: 9.43 min (method 02-B4-4).

MS: m/z=1435, 1077.

MALDI-TOF: 4303.

Example 18

11-(4-(4-((S)-2-carbamoyl-2-([Glu³]GLP-2ylleucinylamino))phenoxymethyl)-1H-1,2,3-triazol-1-yl)undecanoic acid and 1-(5-(4-((S)-2-carbamoyl-2-([Glu³]GLP-2ylleucinylamino))phenoxymethyl)-1H-1,2,3-triazol-1-yl)undecanoic acid

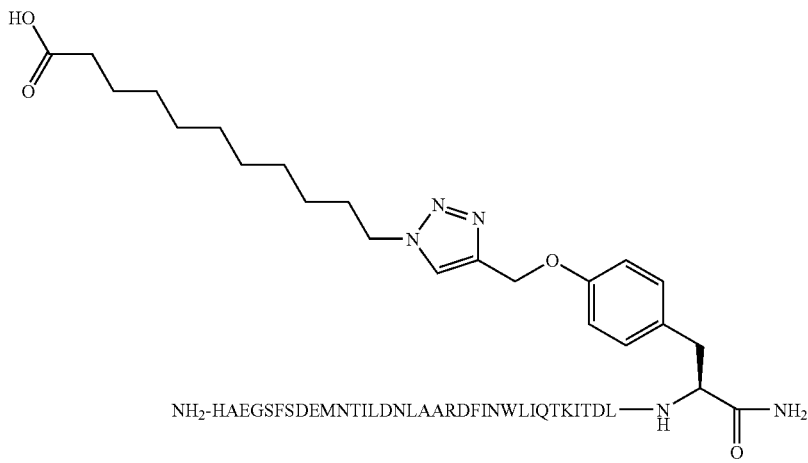

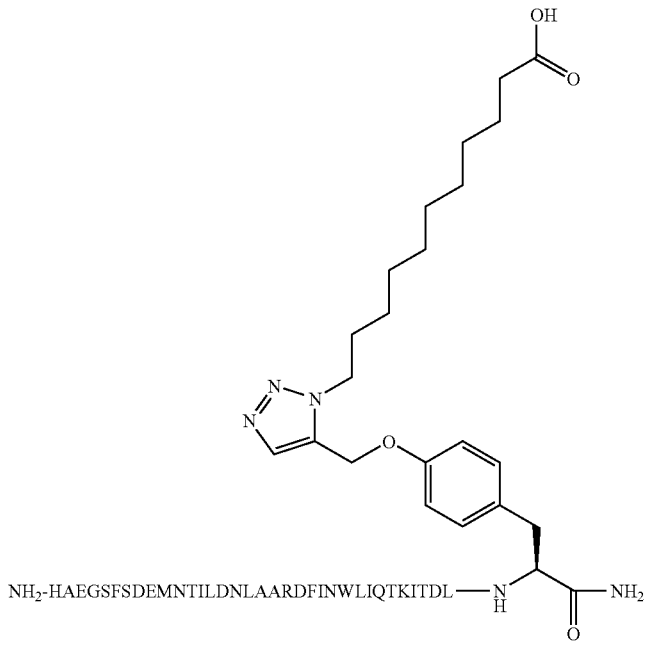

2,6-Lutidine was added to a mixture of (2S)-2-([Glu³]GLP-2ylleucinylamino)-3-(4-(prop-2-ynyloxy)phenyl)propionamide (1.0 mg, 244 pmol) in water (0.5 ml) to give a clear solution. A solution of 11-azidoundecanoic acid (0.554 mg, 0.0025 mmol) in acetonitrile (0.25 ml) and a solution of copper(I) iodide (0.467 mg, 0.0025 mmol) in acetonitrile (0.25 ml) were added successively. The reaction mixture was left for 16 h at room temperature. It was fractionated on a reversed phase $C_{18}$ column on a HPLC, using a gradient of 35-75% acetonitrile in water in a buffer of 0.1% trifluoroacetic acid to give approx. 0.3 mg of 11-(4-(4((S)-2-carbamoyl-2-([Glu³]GLP-2ylleucinylamino))phenoxymethyl)-1,2,3-triazolyl)undecanoic acid or 11-(5-(4-((S)-2-carbamoyl-2-([Glu³]GLP-2ylleucinylamino))phenoxymethyl)-1H-1,2,3-triazol-1-yl)undecanoic acid or a mixture thereof.

HPLC: 9.27 min (method 02-B4-4).
MS: m/z=1441.8, 1081.3, 865.2, 721.2, 618.9.
MALDI-TOF: m/z=4317

Example 19

2-([Glu³]GLP-2ylleucinyl)-3-(4-((1-((N-(mPeg20kDayl)carbamoyl)decanyl)-1H-1,2,3-tetrazol-4-yl)methoxy)phenyl)propionamide and 2-([Glu³]GLP-2ylleucinyl)-3-(4((1-((N-(mPeg20kDayl)carbamoyl)decanyl)-1H-1,2,3-tetrazol-5-yl)methoxy)phenyl)propionamide

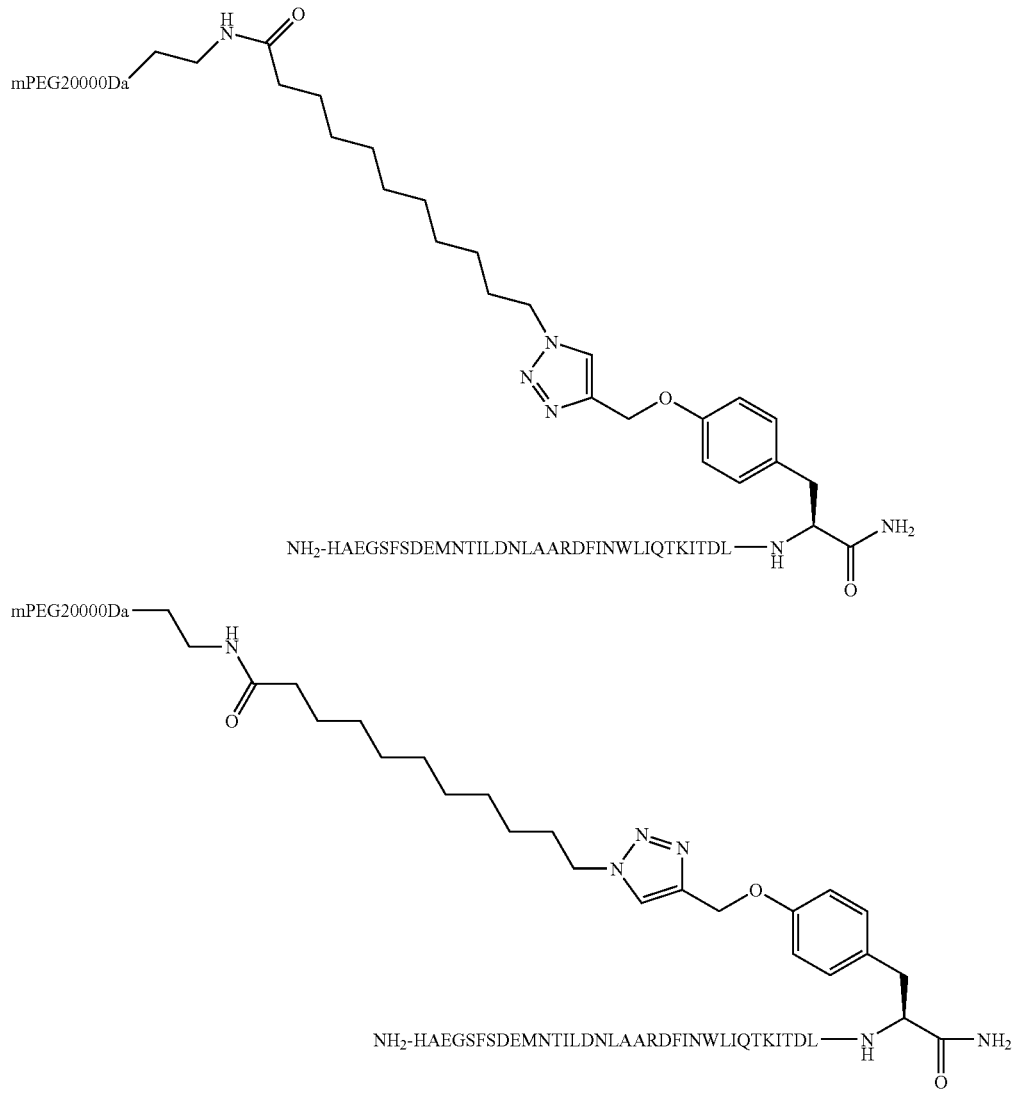

Step 1:

11-Azidoundecanoic acid 2,5-dioxopyrroldin-1-yl ester

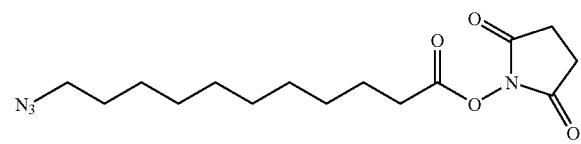

N,N,N',N'-Tetramethyl-O-(N-succinimidyl)uranium tetrafluoroborate (1.32 g, 4.40 mmol) was added to a solution of 11-azidoundecanoic acid (1.00 g, 4.40 mmol) and triethylamine (0.61 ml, 4.40 mmol) in N,N-dimethylformamide (10 ml). The reaction mixture was stirred for 2 h at room temperature. It was diluted with ethyl acetate (50 ml) and washed with water (3×50 ml). The organic phase was dried over sodium sulphate. The solvent was removed in vacuo to give 1.40 g of crude 11-azidoundecanoic acid 2,5-dioxopyrroldin-1-yl ester, which was used in the next steps without further purification.

MS: m/z=347 [M+Na⁺]

¹H-NMR (CDCl₃): δ 1.35 (m, 12H); 1.60 (quintett, 2H); 1.75 (quintett, 2H); 2.60 (t, 2 H); 1.85 (m, 4H); 3.25 (t, 2H).

Step 2:

11-AzidoundecanoylaminomPEG20 kDa

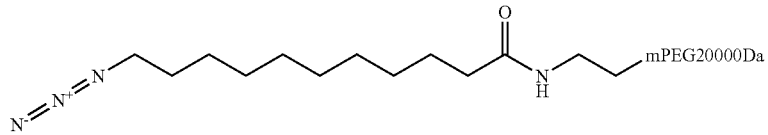

A solution of 11-azidoundecanoic acid 2,5-dioxopyrrolidin-1-yl ester (227 mg, 0.7 mmol) was added to a solution of commercially available mPEG20000DA-amine (Nektar 2M2U0P01, 5.00 g, 0.25 mmol) and triethylamine (0.174 ml, 1.25 mmol) in dichloromethane (50 ml). The reaction mixture was stirred at room temperature for 16 h. Ether (800 ml) was added. The formed precipitation was isolated by filtration and washed with ether (2×100 ml). It was dried in vacuo to give 4.58 g of 11-azidoundecanoylaminomPEG20kDa.

Step 3:

A solution of ascorbic acid (1.72 mg, 9766 nmol) and 2,6-lutidine (0.0024 ml) in water (0.10 ml) was added to a solution of copper(II) sulphate pentahydrate (0.49 mg, 1954 nmol) in water (0.1 ml). This solution was kept for 5 min at room temperature. A part of the resulting mixture (0.025 ml) was added to a solution of (S)-2-([Glu$^3$]GLP-2ylleucinyl)-3-(4-propargyloxyphenyl)propionamide (0.1 mg, 24 nmol), 2,6-lutidine (0.0012 ml) and 11-azidoundecanoylaminomPEG20kDa (0.049 mg, 240 nmol) in water (0.075 ml). The reaction mixture was kept at room temperature. After 24 h, a SDS-gel electrophoreses applying a 10% Bis-Tirs Gel of NuPAGE (Invitrogen) and a SilverXpress® silver staining method, showed the formation of high-molecular peptide, in accordance with the expectations for 2-([Glu$^3$]GLP-2ylleucinyl)-3-(4-((1-((N-(mPeg20kDayl)carbamoyl)decanyl)-1H-1,2,3-tetrazol-4-yl)methoxy)phenyl)propionamide and 2-([Glu$^3$]GLP-2ylleucinyl)-3-(4-((1-((N-(mPeg20kDayl)carbamoyl)decanyl)-1H-1,2,3-tetrazol-5-yl)methoxy)phenyl)propionamide.

Example 20

N—((S)-5-([Leu$^{37}$]GLP-1 (7-37)ylamino)-5-carbamoylpentyl)-4-acetyl benzamide Step 1:

[Leu$^{37}$]GLP-1(7-37)ylalanine was prepared as in example 9

Step 2:

CPY-Catalyzed Transpeptidation of 4-acetyl-N-((5S)-5-amino-5-carbamoylpentyl)benzamide with [Leu$^{37}$]GLP-1(7-37)ylalanine To a mixture of 4-acetyl-N-((5S)-5-amino-5-carbamoylpentyl)benzamide (final concentration 100 mM) and hydroxypropyl-β-cyclodextrin (4% w/v final concentration) in solution in HEPES buffer 250 mM pH8 containing 5 mM EDTA was added [Leu$^{37}$]GLP-1(7-37)ylalanine (1 mM final concentration) in solution in HEPES buffer 250 mM pH8 containing 5 mM EDTA. The pH was adjusted to 8.1 by addition of diisopropylethylamine. The reaction was started by addition of the enzyme in solution in water (10 U/ml final concentration). The reaction is monitored by HPLC.

HPLC method:

Column: Vydac C18 (218TP53) 250×4.6

A: (NH4)$_2$SO$_4$ 50 mM, 0.5% CH$_3$CN, pH2.5 B: CH$_3$CN/TFA 0.1%

1.5 ml/min 5 to 45% B over 20 min detection at 214 nm

40 C

After 6 h30 at 30° C., the reaction mixture content was about 22% of the remaining starting compound [Leu$^{37}$]GLP-1(7-37)ylalanine (retention time: 18.1 min), 70% of the transpeptidation product (retention time: 18.3 min) and 8% of the hydrolysis product [Leu$^{37}$]GLP-1(7-37) (retention time: 18.4 min).

MALDI-TOF: m/z=3684 (S)-5-[Leu$^{37}$]GLP-1(7-37)ylamino)5-carbamoylpentyl)4-acetyl benzamide), 3482 ([Leu$^{37}$]GLP-1(7-37)ylalanine), 3411 ([Leu$^{37}$]GLP-1(7-37)) and 1162 and 1742 ([Leu$^{37}$]GLP-1(7-37)ylalanine).

MS (electrospray): m/z=1844 and 1229 ((S)-5-[Leu37]GLP-1(7-37)ylamino)5-carbamoylpentyl) 4-acetyl benzamide), 1139 ad 1702 ([Leu$^{37}$]GLP-1(7-37)) and 1162 and 1742 ([Leu$^{37}$]GLP-1(7-37)ylalanine).

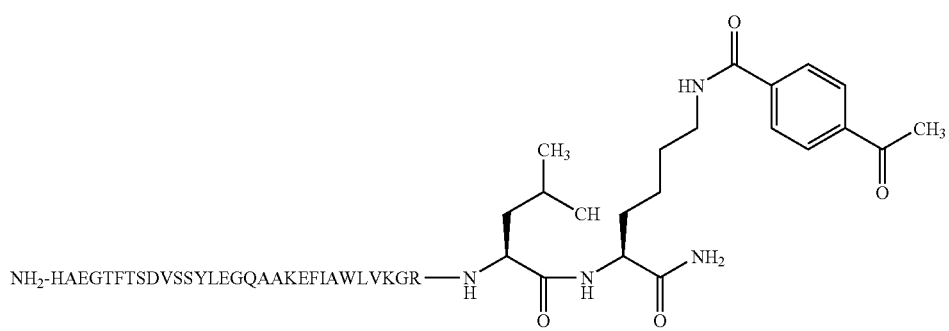

Example 21

N—((S)-5-([Leu³⁷]GLP-1(7-37)ylamino)-5-carbamoylpentyl)-4-[1-[2-(1-(hexadecanoyl)piperidin-4-yl))ethoxyimino]ethyl]benzamide

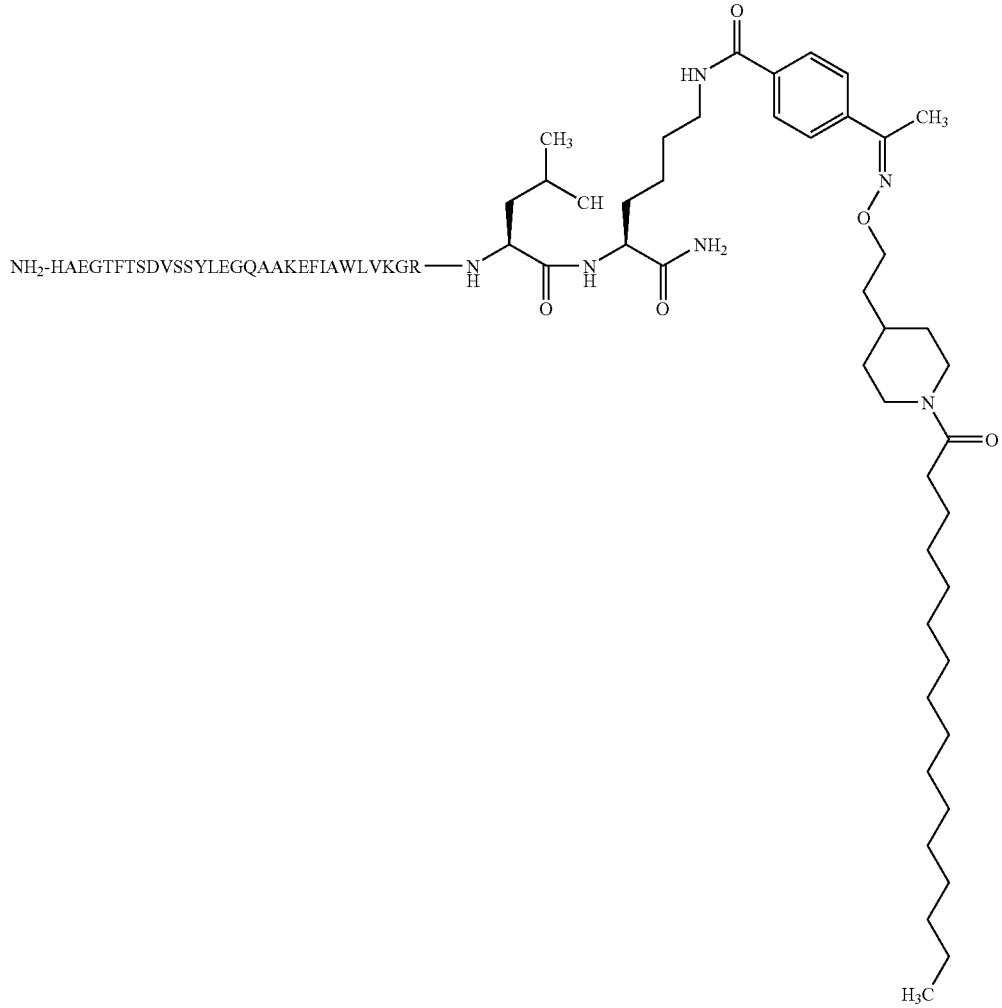

To a solution of N—((S)-5-([Leu³⁷]GLP-1(7-37)ylamino)-5-carbamoylpentyl)-4-acetyl benzamide in acetate buffer 50 mM pH4 (final concentration 0.3 mM) was added 1-[4-(2-(aminooxy)ethyl)piperidin-1-yl]hexadecan-1-one (final concentration 3 mM) in solution in acetonitrile (final acetonitrile concentration: 18% v/v). The reaction was run at 30° C. and followed by HPLC.

HPLC method:

Column: Vydac C18 (218TP53) 250×4.6

A: H₂O/TFA 0.1%

B: CH₃CN/TFA 0.1%

10% B for 5 min, then 10 to 91% B over 27 min 1 ml/min

40 C

Detection at 214 and 280 nm

Retention time of N—((S)-5-([Leu³⁷]GLP-1(7-37)ylamino) 5-carbamoylpentyl)-4-acetyl benzamide: 18.4 min, retention times of products: 26.5 and 27.1 min.

More than 90% yield was obtained after 4 h reaction time.
MS (electrospray): m/z=1351.4 (calc: 1350.9)
MALDI-TOF: m/z=4048 (calc: 4049.8).

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A conjugated peptide obtainable by a method comprising the steps of
   i) reacting in one or more steps a peptide with a first compound bearing one or more functional groups, which are not accessible in any of the amino acids residues constituting said peptide, in the presence of an enzyme capable of catalyzing the incorporation of said first compound into the C-terminal of said peptide to form a transacylated peptide, and
   ii) reacting in one or more steps said transacylated peptide with a second compound comprising one or more functional groups, wherein said functional group(s) do not react with functional groups accessible in the amino acid residues constituting said peptide, and wherein said functional group(s) in said second compound is capable of reacting with said functional group(s) in said first compound so that one or more covalent bond between said transacylated peptide and said second compound is formed, and wherein said peptide P is reacted in one or more steps with a first compound, which is an α-amino acid amide represented by the formula

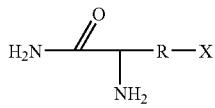

in the presence of carboxypeptidase to form a transacylated peptide of the formula

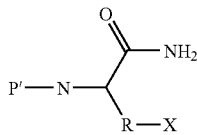

said transacylated peptide being further reacted in one or more steps with a second compound of the formula

Y-E-Z to form a conjugated peptide of the formula

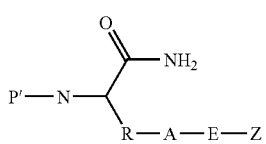

wherein R represents a linker or a bond;
P' represents a peptide formed by removing the C-terminal amino acid from the peptide P, P selected from the group consisting of: human insulin, GLP-1, GLP-2, human growth hormone (GH) and factor VII;
X is selected from amongst keto-, aldehyde-, —NH—NH$_2$, —O—C(O)—NH—NH$_2$, —NH—C(O)—NH—NH$_2$, —NH—C(S)—NH—NH$_2$, —NHC(O)—NH—NH—C(O)—NH—NH$_2$, —NH—NH—C(O)—NH—NH$_2$, —NH—NH—C(S)—NH—NH$_2$, —NH—C(O)—C$_6$H$_4$—NH—NH$_2$, —C(O)—NH—NH$_2$, —O—NH$_2$, —C(O)—O—NH$_2$, —NH—C(S)—O—NH$_2$, alkyne, nitril-oxide and azide;

Y is selected from amongst keto-, aldehyde-, —NH—NH$_2$, —O—C(O)—NH—NH$_2$, —NH—C(O)—NH—NH$_2$, —NH—C(S)—NH—NH$_2$, —NHC(O)—NH—NH—C(O)—NH—NH$_2$, —NH—NH—C(O)—NH—NH$_2$, —NH—NH—C(S)—NH—NH$_2$, —NH—C(O)—C$_6$H$_4$—NH—NH$_2$, —C(O)—NH—NH$_2$, —O—NH$_2$, —C(O)—O—NH$_2$, —NH—C(O)—O—NH, —NH—C(S)—O—NH$_2$, alkyne, nitril-oxide and azide;
E represents a linker or a bond;
A represents oxime, hydrazones, phenylhydrazone, semicarbazone or triazole moieties; and
Z comprises the moiety to be conjugated to the peptide where said moiety decreases the clearance of compound of the formula

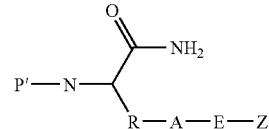

in comparison with the clearance of peptide P and where the moiety is selected from the group consisting of: PEG; mPEG; straight, branched and/or cyclic C$_{2-22}$alkyl, C$_{2-22}$alkenyl, C$_{2-22}$alkynyl, C$_{1-22}$heteroalkyl, C$_{2-22}$heteroalkenyl, C$_{2-22}$heteroalkynyl, wherein each may be optionally substituted with one or more substituents selected from hydroxyl, halogen, carboxyl, heteroaryl and aryl;
   steroid;
   lipids;
   polysaccharides;
   ethylene/maleic anhydride polymer; and
   peptides.

2. The conjugated peptide according to claim 1, wherein P is selected from the group consisting of:
   Lys$^z$(4-((2-(1-(mPEGcarbonyl)piperidin-4yl)ethoxy)imino)pentanoyl)192)hGH(1-192) amide, in which mPEG has a molecular weight of 20 kDa;
   (Lys$^z$(4-((3-(palmitoylamino)propoxy)imino)pentanoyl)192)hGH(1-192) amide;
   (Lys$^z$(4-((3-((2S)-2,6-mPEGcarbonylamino)hexanoylamino)propoxy)imino)pentanoyl)34)GLP-2(1-34) amide, in which mPEG has a molecular weight of 20 kDa;
   (Lys$^z$(4-(1-(2-(3-(mPEG)propanoylamino)hydrazino)ethyl)benzoyl)192)hGH(1-92) amide, in which mPEG has a molecular weight of 10 kDa;
   (S)-3-(4((3-(3-Chlorophenyl)isoxazol-5-yl)methoxy)phenyl)-2-([Glu$^3$, Leu$^{10}$]GLP-2ylleucinylamino)propionic amide;
   (S)-3-(4((3-(3-Chlorophenyl)isoxazol-5-yl)methoxy)phenyl)-2-([Glu$^3$]GLP-2ylleucinylamino)propionic amide;
   3-(3-(3-((4-((S)-2-Carbamoyl-3-([Glu$^3$, Leu$^{10}$]GLP-2ylleucinylamino)ethyl)phenoxyl)methyl)isoxazol-3-yl)benzylcarbamoyl)propionic acid;
   11-(4-(4-((2S)-2-Carbamoyl-2-(([Glu$^3$, Leu$^{10}$]GLP-2ylleucinylamino)ethyl)pheoxymethyl)-1,2,3-triazolyl)undecanoic acid;
   11-(5-(4-((2S)-2-Carbamoyl-2-(([Glu$^3$, Leu$^{10}$]GLP-2ylleucinylamino)ethyl)pheoxymethyl)-1,2,3-triazolyl)undecanoic acid 11-(4-(4-((S)-2-carbamoyl-2-([Glu$^3$]GLP-2ylleucinylamino))phenoxymethyl)-1H-1,2,3-triazol-1-yl)undecanoic acid;

11-(5-(4-((S)-2-carbamoyl-2-([Glu³]GLP-2ylleuciny-lamino))phenoxymethyl)-1H-1,2,3-triazol-1-yl)unde-canoic acid;

2-([Glu³]GLP-2ylleucinyl)-3-(4-((1-((N-(mPeg20kDayl)carbamoyl)decanyl)-1H-1,2,3-tetrazol-4-yl)methoxy)phenyl)propionamide; and 2-([Glu³]GLP-2ylleucinyl)-3-(4-((1-((N-(mPeg20 kDayl)carbamoyl)decanyl)-1H-1,2,3-tetrazol-5-yl)methoxy)phenyl)propionamide.

3. A pharmaceutical composition comprising one or more of the conjugated peptides according to claim 2.

\* \* \* \* \*